US010006004B2

(12) United States Patent
Furcht et al.

(10) Patent No.: US 10,006,004 B2
(45) Date of Patent: *Jun. 26, 2018

(54) MULTIPOTENT ADULT STEM CELLS AND METHODS FOR ISOLATION

(75) Inventors: Leo T. Furcht, Golden Valley, MN (US); Catherine M. Verfaillie, Leuven (BE); Morayma Reyes, Sammamish, WA (US)

(73) Assignee: ABT Holding Company, Cleveland, OH (US)

( * ) Notice: Subject to any disclaimer, the term of this patent is extended or adjusted under 35 U.S.C. 154(b) by 1898 days.

This patent is subject to a terminal disclaimer.

(21) Appl. No.: 12/416,715

(22) Filed: Apr. 1, 2009

(65) Prior Publication Data
US 2009/0203130 A1 Aug. 13, 2009

Related U.S. Application Data

(63) Continuation of application No. 11/238,234, filed on Sep. 29, 2005, now Pat. No. 7,659,118, which is a continuation of application No. 10/048,757, filed as application No. PCT/US00/21387 on Aug. 4, 2000, now Pat. No. 7,015,037.

(60) Provisional application No. 60/147,324, filed on Aug. 5, 1999, provisional application No. 60/164,650, filed on Nov. 10, 1999.

(51) Int. Cl.
*C12N 5/06* (2006.01)
*C12N 5/074* (2010.01)
*A61K 48/00* (2006.01)
*A61K 35/12* (2015.01)
*A61K 39/00* (2006.01)

(52) U.S. Cl.
CPC ............ *C12N 5/0607* (2013.01); *A61K 48/00* (2013.01); *A61K 2035/124* (2013.01); *A61K 2039/5156* (2013.01); *C12N 2501/105* (2013.01); *C12N 2501/11* (2013.01); *C12N 2501/135* (2013.01); *C12N 2501/235* (2013.01); *C12N 2503/00* (2013.01); *C12N 2510/00* (2013.01)

(58) Field of Classification Search
None
See application file for complete search history.

(56) References Cited

U.S. PATENT DOCUMENTS

| 5,486,359 | A | 1/1996 | Caplan et al. |
| 5,827,735 | A | 10/1998 | Young et al. |
| 6,090,625 | A | 7/2000 | Abuljadayel |
| 6,653,134 | B2 | 11/2003 | Prockop et al. |
| 6,777,231 | B1 | 8/2004 | Katz et al. |
| 7,056,738 | B2 | 6/2006 | Prockop et al. |
| 7,229,827 | B2 | 6/2007 | Kim et al. |

| 2001/0033834 | A1 | 10/2001 | Wilkison et al. |
| 2001/0046489 | A1 | 11/2001 | Habener et al. |
| 2002/0061587 | A1 | 5/2002 | Anversa |
| 2002/0164794 | A1 | 11/2002 | Wernet |
| 2003/0003090 | A1 | 1/2003 | Prockop et al. |
| 2003/0059414 | A1 | 3/2003 | Ho et al. |
| 2004/0235165 | A1 | 11/2004 | Prockop et al. |
| 2005/0169896 | A1 | 8/2005 | Li et al. |
| 2006/0177925 | A1 | 8/2006 | Rosenberg et al. |

FOREIGN PATENT DOCUMENTS

| JP | 2001-521380 A | 6/2001 |
| WO | WO 96/23870 | 8/1996 |
| WO | 1998-43679 | 10/1998 |
| WO | WO 99/16863 | 4/1999 |
| WO | WO 99/35243 | 7/1999 |
| WO | WO 01/04268 | 1/2001 |
| WO | WO 01/08691 | 2/2001 |
| WO | WO 01/21766 | 3/2001 |
| WO | WO 01/21767 | 3/2001 |
| WO | WO 01/62901 | 8/2001 |
| WO | WO 02/08388 | 3/2002 |
| WO | WO 02/34890 | 5/2002 |

OTHER PUBLICATIONS

U.S. Patent and Trademark Office, Office Action dated Jun. 24, 2005 in related U.S. Appl. No. 10/040,757.
U.S. Patent and Trademark Office, Office Action and 892 dated Jun. 27, 2008 in related U.S. Appl. No. 10/467,963.
U.S. Patent and Trademark Office, Office Action dated Oct. 15, 2009 in related U.S. Appl. No. 10/467,963.
U.S. Patent and Trademark Office, Office Action dated Apr. 7, 2008 in related U.S. Appl. No. 11/151,689.
U.S. Patent and Trademark Office, Office Action dated Jan. 4, 2006 in related U.S. Appl. No. 11/238,234.
U.S. Patent and Trademark Office, Office Action dated Aug. 29, 2006 in related U.S. Appl. No. 11/238,234.
U.S. Patent and Trademark Office, Office Action dated Apr. 3, 2007 in related U.S. Appl. No. 11/238,234.
U.S. Patent and Trademark Office, Office Action dated Oct. 7, 2008 in related U.S. Appl. No. 11/238,234.
Information Disclosure Statement and 1449, filed Sep. 29, 2005 in related U.S. Appl. No. 11/238,234.
Information Disclosure Statement and 1449, filed Mar. 5, 2007 in related U.S. Appl. No. 11/238,234.
Information Disclosure Statement and 1449, filed Oct. 2, 2007 in related U.S. Appl. No. 11/238,234.
Communication and 1449, filed Oct. 2, 2007 in related U.S. Appl. No. 11/238,234, and supplemental 1449 submitted on Oct. 4, 2007.
Information Disclosure Statement and 1449, filed Oct. 4, 2007 in related U.S. Appl. No. 11/238,234
Information Disclosure Statement and 1449, filed Oct. 19, 2007 in related U.S. Appl. No. 11/238,234.
Information Disclosure Statement and PTO/SB/08b, filed Sep. 23, 2008 in related U.S. Appl. No. 11/238,234.

(Continued)

*Primary Examiner* — David W Berke-Schlessel
(74) *Attorney, Agent, or Firm* — Tarolli, Sundheim, Covell & Tummino LLP

(57) ABSTRACT

The invention provides isolated stem cells of non-embryonic origin that can be maintained in culture in the undifferentiated state or differentiated to form cells of multiple tissue types. Also provided are methods of isolation and culture, as well as therapeutic uses for the isolated cells.

10 Claims, 16 Drawing Sheets

(56) References Cited

OTHER PUBLICATIONS

Information Disclosure Statement, Second Communication and PTO/SB/08b, filed Dec. 24, 2008 in related U.S. Appl. No. 11/238,234.
Information Disclosure Statement and PTO/SB/08b, filed Apr. 21, 2009 in related U.S. Appl. No. 11/238,234.
Cambrex specimens, "Poietics Human Mesenchymal Stem Cell Systems," Cambrex BioScience Walkersville, Inc. (2005).
Prockop, D., "Marrow stromal cells as stem cells for nonhematopoietic tissues" Science; 276:71-74 (1997).
Bjornson et al., "Turning brain into blood: a hematopoietic fate adopted by adult neural stem cells in vivo" Science; 283:534-537 (1999).
Reyes et al., "Purification and ex vivo expansion of postnatal human marrow mesodermal progenitor cells" Blood; 98:2615-25 (2001).
Bouwens, L., "Transdifferentiation versus stem cell hypothesis for the regeneration of islet beta-cells in the pancreas" Microscopy Research and Technique; 43:332-336 (1998).
Reyes et al., "Origin of endothelial progenitors in human postnatal bone marrow" J. Clin. Invest.; 109:1-10 (2002).
Reyes et al., "Characterization of multilineage mesodermal progenitor cells in adult marrow" Abstract No. 124, American Society for Hematology (2001).
Reyes et al., "Turning marrow into brain: generation of glial and neuronal cells from adult bone marrow mesenchymal stem cells" Abstract No. 1676, American Society for Hematology (2001).
Reyes et al., "Skeletal smooth and cardiac muscle differentiation from single adult marrow derived mesodermal progenitor cells" Abstract No. 2610, American Society for Hematology (2001).
Reyes et al., "In vitro and in vivo characterization of neural cells derived from mesenchymal stem cells" Abstract 2126, American Society for Hematology (2001).
Reyes et al., "Endothelial cells generated from human marrow derived mesenchymal stem cells (MSC)" Abstract No. 2276, American Society for Hematology (2001).
Zhao et al., "Immunohistochemical identification of multipotent adult progenitor cells from human bone marrow after transplantation into the rat brain" Brain Res Brain Res Protoc; 11:38-45 (2003).
Jiang et al., "Multipotent progenitor cells can be isolated from postnatal murine bone marrow, muscle, and brain" Exp. Hematol.; 30:896-904 (2002).
Jiang et al., "Pluripotency of mesenchymal stem cells derived from adult marrow" Nature; 418:41-49 (2002).
Schwartz, R., "Multipotent adult progenitor cells from bone marrow differentiate into hepatocyte-like cells" J Clin Invest.; 109:1291-1302 (2002).
Zhao et al., "Human bone marrow stem cells exhibit neural phenotypes and ameliorate neurological deficits after grafting into the ischemic brain of rats" Exp Neurol; 174:11-20.
Lamming et al., "Spontaneous circulation of myeloid-lymphoid-initiating cells and SCID-repopulating cells in sickle cell crisis" J. Clin. Invest.; 111:811-819 (2003).
Qi et al., "Identification of genes responsible for osteoblast differentiation from human mesodermal progenitor cells" Nat. Acad. Sci. USA; 100:3305-3310 (2003).
Verfaillie, C. "Investigator Profile" Journal of Hematotherapy and Stem Cell Research; 11:441-444 (2002).
Verfaillie et al., "Stem cells: hype and reality" Hematology (Am Soc Hematol Educ Program); 369-391 (2002).
Verfaille, C., "Optimizing hematopoietic stem cell engraftment: a novel role for thrombopoeitin" J. Clin. Invest.; 110:303-304 (2002).
Liu et al., "Myeloid-lymphoid-initiating cells (ML-IC) are highly enriched in the rhodamine-C-Kit(+) CD33(−)CD38(−) fraction of umbilical cord CD34(+)" Exp. Hematol.; 30:582-589 (2002).
Lewis et al., "Multi-lineage expansion potential of primitive hematopoietic progenitors: superiority of umbilical cord blood compared to mobilized peripheral blood" Exp. Hematol.; 28:1087-1095 (2002).

Verfaillie, C.M., "Meeting Report on an NHLBI Workshop on ex vivo expansion of stem cells, Jul. 29, 1999, Washington D.C. National Heart Lung and Blood Institute" Exp. Hematol.; 28:361-364 (2000).
Punzel et al., The myeloid-lymphoid initiating cell (ML-IC) assay assesses the fate of multipotent human progenitors in vitro' Blood; 93:3750-3756 (1999).
Roy et al., "Expression and function of cell adhesion molecules on fetal liver, cord blood and bone marrow hematopoietic progenitors: implications for anatomical localization and developmental stage specific regulation of hematopoiesis" Exp. Hematol.; 27:302-312 (1999).
Miller et al., "Ex vivo culture of CD34+/Lin-/DR-cells in stroma-derived soluble factors, interleukin-3, and macrophage inflammatory protein-1 alpha maintains not only myeloid but also lymphoid progenitors in a novel switch culture assay" Blood; 15:4516-4522 (1998).
Verfaillie, C., "Stem cells in chronic myelogenous Leukemia" Hematol. Oncol. Clin. North Am.; 11:1079-1114 (1997).
Prosper et al., "Phenotypic and functional characterization of long-term culture-initiating cells present in peripheral blood progenitor collections of normal donors treated with granulocyte colony-stimulating factor" Blood; 15:2033-2042 (1996).
Lodie et al., "Systematic analysis of reportedly distinct populations of multipotent bone marrow-derived stem cells reveals a lack of distinction" Tissue Engineering; 8:739-751 (2002).
Pagen Westphal, S., "Adult bone marrow eyed as source of stem cells" Boston Globe, Jan. 24, 2002.
Pagen Westphal, S., "Ultimate stem cell discovered" New Scientist, Jan. 23, 2002.
Wade et al., "Scientists herald a versatile adult cell" The New York Times on the Web, Jan. 25, 2002.
Associated Press, "Adult stem cells show versatility" New York Times on the web, Jan. 25, 2002.
Rosford et al., "The octamer motif present in the Rex-1 promoter binds Oct-1 and Oct-3 expressed by EC cells and ES cells" Biochem. Biophys. Res. Comm.; 203:1795-1802 (1994).
Rosner et al., "Oct-3 is a maternal factor required for the first mouse embryonic division" Cell; 64:1103-1110 (1991).
Pittenger et al., "Multilineage potential of adult human mesenchymal stem cells"; Science; 284:143-147 (1999).
Ben-Shushan et al., "Rex1, a gene encoding a transcription factor expressed in the early embryo, is regulated via Oct-3/4 and Oct-6 binding to and octamer site and a novel protein, R ox-1, binding to an adjacent site" Mol. Cell Biol.; 18:1866-1878.
Reyes et al., "Characterization of multipotent adult progenitor cells, a subpopulation of mesenchymal stem cells" Annals of the New York Academy of Science; 938:231-235.
Anjos-Afonso and Bonnet, "Nonhematopoietic/endothelial SSE-1+ cells define the most primitive progenitors in the adult murine bone marrow mesenchymal compartment" Blood; 109:1298-1306 (2007).
Bertani et al., "Neurogenic potential of human mesenchymal stem cells revisited: analysis by immunostaining, time-lapse video and microarray" J Cell Sci.; 118:3925-36 (2005).
Bodnar et al., "Extension of life-span by introduction of telomerase into normal human cells" Science; 279:349-352 (1998).
Horwitz et al., "Clarification of the nomenclature for MSC: the international society for cellular therapy position paper" Cytotherapy; 7:393-395 (2005).
Lu et al., "Induction of bone marrow stromal cells to neurons: differentiation, transdifferentiation, or artifact" J Neurosci Res; 77:174-91 (2004).
Neuhuber et al., "Reevaluation of in vitro differentiation protocols for bone marrow stromal cells: disruption of actin cytoskeleton induces rapid morphological changes and mimics neuronal phenotype" J Neurosci Res; 77:192-204 (2004).
Simonsen et al., "Telomerase expression extends the proliferative life-span and maintains the osteogenic potential of human bone marrow stromal cells" Nature Biotechnology; 2.

(56) References Cited

OTHER PUBLICATIONS

Zimmerman et al., "Lack of telomerase activity in human mesenchymal stem cells" Leukemia; 17:1146-1149 (2003).

Izadpanah et al., "Biologic properties of mesenchymal stem cells derived from bone marrow and adipose tissue" Journal of Cellular Biochemistry; 99:1285-1297 (2006).

Long et al., "Neural cell differentiation in vitro from adult human bone marrow mesenchymal stem cells" Stem Cells and Development; 14:65-69 (2005).

Moriscot et al., "Human bone marrow mesenchymal stem cell can express insulin and key transcription factors of the endocrine pancreas developmental pathway upon genetic and/or microenvironmental manipulation in vitro" Stem Cells; 23:594-604 (2005).

Sanchez-Ramos et al., "Adult bone m arrow stromal cells differentiate into neural cells in vitro" Exp. Neurol.; 164:247-56 (2000).

Eglitis et al., "Hematopoietic cells differentiate into both microglia and macroglia in the brain of adult mice" Proc. Natl. Acad. Sci. USA; 94:4080-85 (1997).

Kopen et al., "Marrow stromal cells migrate throughout forebrain and cerebellum, and they differentiate into astrocytes after injection into neonatal mouse brains" Proc. Natl. Acad. Sci. USA; 96:10711-16 (1999).

Lagasse et al., "Purified hematopoietic stem cells can differentiate into hepatocytes in vivo" Nature Medicine; 6:1229-1234 (2000).

Wang, X. et al., "Cell fusion is the principal source of bone-marrow-derived hepatocytes" Nature; 422:897-901 (2003).

Giles, J., "The trouble with replication" Nature, 422:344-347 (2006).

Verfaillie, C.M., Multipotent adult progenitor cells: an update: Novartis Found Symp., 254:55-65 (2005).

Aldhous et al., "Fresh questions on stem cell findings" New Scientist, Mar. 21, 2007.

Brazelton et al., "From marrow to brain: expression of neuronal phenotypes in adult mice" Science; 290:1775-9 (2000).

Clarke et al., "Generalized potential of adult neural stem cells" Science; 288: 1660-3 (2000).

Johansson et al., "Neural stem cells in the adult human brain" Exp. Cell. Res.; 253:733-6 (1999).

Mezey et al., "Turning blood into brain: cells bearing neuronal antigens generated in vivo from bone marrow" Science; 290:1779-82 (2000).

Morshead et al., "Hematopoietic competence is a rare property of neural stem cells that may depend on genetic and epigenetic alterations" Nat. Med.; 8:268-73 (2002).

Petersen et al., "Bone marrow as a potential source of hepatic oval cells" Science; 284:1168-70 (1999).

Scintu et al., "Differentiation of human bone marrow stem cells into cells with a neural phenotype: diverse effects of two specific treatments" BMC Neurosci.; 7:14 (2006).

Decision on Motions; Patent Interference No. 105,953 SGL, Tech Center 1600; filed Sep. 26, 2014.

Kraft, H.J., et al. Oct-4 Regulates Alternative Platelet-derived Growth Factor α Receptor Gene Promoter in Human Embryonal Carcinoma Cells. J Biol Chem; 1996; vol. 271, No. 22; pp. 12873-12878.

Gabr, et al., "Insulin-Producing Cells From Adult Human Bone Marrow Mesenchymal Stem Cells Control Streptozotocin-Induced Diabetes in Nude Mice", Cell Transplantation, vol. 22, pp. 133-145, 2013.

Zuk PA, "The intracellular distribution of the ES cell totipotent markers OCT4 and Sox2 in adult stem cells differs dramatically according to commercial antibody used", J Cell Biochem., 106(5):867-77, Apr. 1, 2009.

Gimble, et al., "In vitro Differentiation Potential of Mesenchymal Stem Cells", vol. 35, pp. 228-238, Jun. 2008.

Lee, et al., "In Vitro Hepatic Differentiation of Human Mesenchymal Stem Cells", vol. 40, Issue 6, pp. 1275-1284, Dec. 2004.

Pittenger, et al., "Human Mesenchymal Stem Cells: Progenitor Cells for Cartilage, Bone, Fat and Stroma", Lymphoid Organogenesis, vol. 251, pp. 3-11, 2001.

Shetty, et al., "Comparison of proliferative and multilineage differentiation potentials of cord matrix, cord blood, and bone marrow mesenchymal stem cells", Asian Journal of Transfusion Science, vol. 4, Issue 1, pp. 14-24, 2010.

Roche et al., Oct-4, Rex-1, and Gata-4 Expresion in Human MSC Increase the Differentiation Efficiency But Not hTERT Expression, of Cellular Biochemistry 101 : 271-280 (2007).

Wu et al., Generation of Pancreatic β Cells From Mesenchymal Stem Cells to Treat Type 1 Diabetes, OA Stem Cells, Mar. 22, 2014 : 2 (1) : 5.

Guo et al., Differential of Mesenchymal Stem Cells Into Dopaminergic Neuron-like Cells In Vito, Biomedical and Environmental Sciences, 18, 36-42 (2005).

Piccinato et al., High OCT4 and Low p16INK4A Expressions Determine In Vitro Lifespan of Mesenchymal Stem Cells. Stem Cells International, vol. 2015, Article ID 369828, 11 pages.

MESENCHYMAL DIFFERENTIATION

*Bone Sialoprotein*

Day 0   7   12   15

*Toluidin blue*   *Collagen-II*

Day 0   7   12   15

*Oil Red*   *PPAR-γ*

Day 0   15

MYOTUBE FORMATION

MYOTUBES WERE LABELED WITH THE MEMBRANE DYE, PKH26 (RED). MYOBLASTS WERE DERIVED FROM eGFP TRANSDUCED MPC (GREEN). CELLS WERE COCULTURED FOR 2 DAYS AND THEN EXAMINED BY FLUORESCENCE MICROSCOPY

MULTIPOTENT ADULT STEM CELLS AND METHODS FOR ISOLATION

Portions of the present invention were made with support of the United States Government via a grant from the National Institutes of Health/National Institute of Allergy and Infectious Diseases to Morayama Reyes under grant number 1F31AI-Gn10291. The U.S. Government may therefore have certain rights in the invention.

FIELD OF THE INVENTION

The invention relates generally to methods for isolation of stem cells, cells isolated by the methods, and therapeutic uses for those cells. More specifically, the invention relates to isolated marrow-derived progenitor cells which have the potential to differentiate to form cells of a variety of cell lineages, as well as methods for isolating the cells and for inducing specific differentiation of the cells isolated by the method, and specific markers that are present in these cells such as proteins and transcription factors.

BACKGROUND OF THE INVENTION

Organ and tissue generation from stem cells and their subsequent transplantation provide promising treatments for a number of pathologies, making stem cells a central focus of research in many fields. Using stem cells for generation of organs and tissues for transplantation provides a promising alternative therapy for diabetes, Parkinson's disease, liver disease, heart disease, and autoimmune disorders, to name a few. However, there are at least two major problems associated with organ and tissue transplantation. First, there is a shortage of donor organs and tissues. As few as 5 percent of the organs needed for transplant in the United States along ever become available to a recipient. (Evans, et al., *J. Am. Med. Assoc.* (1992) 267: 239-246.) According to the American Heart Association, only 2,300 of the 40,000 Americans who needed a new heart in 1997 received one, and the American Liver Foundation reports that there are fewer than 3,000 donors for the nearly 30,000 patients who die each year from liver failure. The second major problem is the potential incompatibility of the transplanted tissue with the immune system of the recipient. Because the donated organ or tissue is recognized by the host immune system as foreign, anti-rejection medications must be provided to the patient at a significant cost—both financially and physically.

Xenotransplantation, or transplantation of tissue or organs from another species, could provide an alternative means to overcome the shortage of human organs and tissues. Xenotransplantation would offer the advantage of advanced planning of the transplant, allowing the organ to be harvested while still healthy and allowing the patient to undergo any beneficial pretreatment prior to transplant surgery. Unfortunately, xenotransplantation does not overcome the problem of tissue incompatibility, but instead exacerbates it. Furthermore, according to the Centers for Disease Control, there is evidence that damaging viruses cross species barriers. Pigs have become likely candidates as organ and tissue donors, yet cross-species transmission of more than one virus from pigs to humans has been documented. For example, over a million pigs were recently slaughtered in Malaysia in an effort to contain an outbreak of Hendra virus, a disease that was transmitted to more than 70 humans with deadly results. (Butler, D., *Nature* (1999) 398: 549.)

Stem Cells: Definition and Use

The most promising source of organs and tissues for transplantation therefore lies in the development of stem cell technology. Theoretically, stem cells can undergo self-renewing cell division to give rise to phenotypically and genotypically identical daughters for an indefinite time and ultimately can differentiate into at least one final cell type. By generating tissues or organs from a patient's own stem cells, or by genetically altering heterologous cells so that the recipient immune system does not recognize them as foreign, transplant tissues can be generated to provide the advantages associated with xenotransplantation without the associated risk of infection or tissue rejection.

Stem cells also provide promise for improving the results of gene therapy. A patient's own stem cells could be genetically altered in vitro, then reintroduced in vivo to produce a desired gene product. These genetically altered stem cells would have the potential to be induced to differentiate to form a multitude of cell types for implantation at specific sites in the body, or for systemic application. Alternately, heterologous stem cells could be genetically altered to express the recipient's major histocompatibility complex (MHC) antigen, or no MHC, to allow transplant of those cells from donor to recipient without the associated risk of rejection.

Stem cells are defined as cells that have extensive, some would say indefinite, proliferation potential that differentiate into several cell lineages, and that can repopulate tissues upon transplantation. The quintessential stem cell is the embryonal stem (ES) cell, as it has unlimited self-renewal and multipotent differentiation potential. These cells are derived from the inner cell mass of the blastocyst, or can be derived from the primordial germ cells from a post-implantation embryo (embryonal germ cells or EG cells). ES and EG cells have been derived from mouse, and more recently also from non-human primates and humans. When introduced into mouse blastocysts or blastocysts of other animals, ES cells can contribute to all tissues of the mouse (animal). When transplanted in post-natal animals, ES and EG cells generate teratomas, which again demonstrates their multipotency. ES (and EG) cells can be identified by positive staining with the antibodies SSEA1 and SSEA4.

At the molecular level, ES and EG cells express a number of transcription factors highly specific for these undifferentiated cells. These include oct-4 and Rex-1. Also found are the LIF-R and the transcription factors sox-2 and Rox-1, even though the latter two are also expressed in non-ES cells. oct-4 is a transcription factor expressed in the pregastrulation embryo, early cleavage stage embryo, cells of the inner cell mass of the blastocyst, and in embryonic carcinoma (EC) cells. oct-4 is down-regulated when cells are induced to differentiate in vitro and in the adult animal oct-4 is only found in germ cells. Several studies have shown that oct-4 is required for maintaining the undifferentiated phenotype of ES cells, and plays a major role in determining early steps in embryogenesis and differentiation. oct-4, in combination with Rox-1, causes transcriptional activation of the Zn-finger protein Rex-1, and is also required for maintaining ES in an undifferentiated state. Likewise, sox-2, is needed together with oct-4 to retain the undifferentiated state of ES/EC and to maintain murine (but not human) ES cells. Human or murine primordial germ cells require presence of LIF. Another hallmark of ES cells is presence of telomerase, which provides these cells with an unlimited self-renewal potential in vitro.

Stem cells have been identified in most organ tissues. The best characterized is the hematopoietic stem cell. This is a mesoderm-derived cell that has been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages (see Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 759,793; DiGuisto, et al., U.S. Pat. No. 5,681,599; Tsukamoto, et al., U.S. Pat. No. 5,716,827; Hill, B., et al., Exp. Hematol. (1996) 24 (8): 936-943). When transplanted into lethally irradiated animals or humans, hematopoietic stem cells can repopulate the erythroid, neutrophil-macrophage, megakaryocyte and lymphoid hemopoietic cell pool. In vitro, hemopoietic stem cells can be induced to undergo at least some self-renewing cell divisions and can be induced to differentiate to the same lineages as is seen in vivo. Therefore, this cell fulfills the criteria of a stem cell. Stem cells which differentiate only to form cells of hematopoietic lineage, however, are unable to provide a source of cells for repair of other damaged tissues, for example, heart or lung tissue damaged by high-dose chemotherapeutic agents.

A second stem cell that has been studied extensively is the neural stem cell (Gage F H: Science 287:1433-1438, 2000; Svendsen C N et al, Brain Path 9:499-513, 1999; Okabe S et al, Mech Dev 59:89-102, 1996). Neural stem cells were initially identified in the subventricular zone and the olfactory bulb of fetal brain. Until recently, it was believed that the adult brain no longer contained cells with stem cell potential. However, several studies in rodents, and more recently also non-human primates and humans, have shown that stem cells continue to be present in adult brain. These stem cells can proliferate in vivo and continuously regenerate at least some neuronal cells in vivo. When cultured ex vivo, neural stem cells can be induced to proliferate, as well as to differentiate into different types of neurons and glial cells. When transplanted into the brain, neural stem cells can engraft and generate neural cells and glial cells. Therefore, this cell too fulfills the definition of a stem cell.

Mesenchymal stem cells (MSC), originally derived from the embryonal mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. A third tissue specific cell that has been named a stem cell is the mesenchymal stem cell, initially described by Fridenshtein (Fridenshtein, Arkh. Patol., 44:3-11, 1982). A number of mesenchymal stem cells have been isolated (see, for example, Caplan, A., et al., U.S. Pat. No. 5,486,359; Young, H., et al., U.S. Pat. No. 5,827,735; Caplan, A., et al., U.S. Pat. No. 5,811,094; Bruder, S., et al., U.S. Pat. No. 5,736,396; Caplan, A., et al., U.S. Pat. No. 5,837,539; Masinovsky, B., U.S. Pat. No. 5,837,670; Pittenger, M., U.S. Pat. No. 5,827,740; Jaiswal, N., et al., *J. Cell Biochem.* (1997) 64(2): 295-312; Cassiede P., et al., *J. Bone Miner. Res.* (1996) 11(9): 1264-1273; Johnstone, B., et al., (1998) 238(1): 265-272; Yoo, et al., *J. Bone Joint Surg. Am.* (1998) 80(12): 1745-1757; Gronthos, S., *Blood* (1994) 84(12): 4164-4173; Makino, S., et al., *J. Clin. Invest.* (1999) 103(5): 697-705). Of the many mesenchymal stem cells that have been described, all have demonstrated limited differentiation to form only those differentiated cells generally considered to be of mesenchymal origin. To date, the most multipotent mesenchymal stem cell reported is the cell isolated by Pittenger, et al., which expresses the $SH2^+$ $SH4^+$ $CD29^+$ $CD44^+$ $CD71^+$ $CD90^+$ $CD106^+$ $CD120a^+$ $CD124^+$ $CD14^-$ $CD34^-$ $CD45^-$ phenotype. This cell is capable of differentiating to form a number of cell types of mesenchymal origin, but is apparently limited in differentiation potential to cells of the mesenchymal lineage, as the team who isolated it noted that hematopoietic cells were never identified in the expanded cultures. (Pittenger, et al., *Science* (1999) 284: 143-147.)

Other stem cells have been identified, including gastrointestinal stem cells, epidermal stem cells, and hepatic stem cells, also termed oval cells (Potten C, Philos Trans R Soc Lond B Biol Sci 353:821-30, 1998; Watt F, Philos. Trans R Soc Lond B Biol Sci 353:831, 1997; Alison M et al, Hepatol 29:678-83, 1998). Most of these are less well characterized.

Compared with ES cells, tissue specific stem cells have less self-renewal ability and, although they differentiate into multiple lineages, they are not multipotent. No studies have addressed whether tissue specific cells express markers described above of ES cells. In addition, the degree of telomerase activity in tissue specific stem cells has not been fully explored, in part because large numbers of highly enriched populations of these cells are difficult to obtain.

Until recently, it was thought that organ specific stem cells could only differentiate into cells of the same tissue. A number of recent publications have suggested that adult organ specific stem cells may be capable of differentiating into cells of different tissues. A number of studies have shown that cells transplanted at the time of a bone marrow transplant can differentiate into skeletal muscle (Ferrari Science 279:528-30, 1998; Gussoni Nature 401:390-4, 1999). This could be considered within the realm of possible differentiation potential of mesenchymal cells that are present in marrow. Jackson published that muscle satellite cells can differentiate into hemopoietic cells, again a switch in phenotype within the splanchnic mesoderm (Jackson PNAS USA 96:14482-6, 1999). Other studies have shown that stem cells from one embryonal layer (for instance splanchnic mesoderm) can differentiate into tissues thought to be derived during embryogenesis from a different embryonal layer. For instance, endothelial cells or their precursors detected in humans or animals that underwent marrow transplantation are at least in part derived from the marrow donor (Takahashi, Nat Med 5:434-8, 1999; Lin, Clin Invest 105:71-7, 2000). Thus, visceral mesoderm and not splanchnic mesoderm, such as MSC, derived progeny are transferred with the infused marrow. Even more surprising are the reports demonstrating both in rodents and humans that hepatic epithelial cells and biliary duct epithelial cells are derived from the donor marrow (Petersen, Science 284: 1168-1170, 1999; Theise, Hepatology 31:235-40, 2000; Theise, Hepatology 32:11-6, 2000). Likewise, three groups have shown that neural stem cells can differentiate into hemopoietic cells. Finally, Clarke et al. reported that neural stem cells injected into blastocysts can contribute to all tissues of the chimeric mouse (Clarke, Science 288:1660-3, 2000).

It is necessary to point out that most of these studies have not conclusively demonstrated that a single cell can differentiate into tissues of different organs. Indeed most investigators did not identify the phenotype of the initiating cell. An exception is the study by Weissman and Grompe, who showed that cells that repopulated the liver were present in Lin⁻Thy₁LowSca₁+ marrow cells, which are highly enriched in hematopoietic stem cells. Likewise, the Mulligan group showed that marrow Sp cells, highly enriched for HSC, can differentiate into muscle and endothelium, and Jackson et al. showed that muscle Sp cells are responsible for hemopoietic reconstitution (Gussoni et al., Nature 401: 390-4, 1999).

Transplantation of tissues and organs generated from heterologous embryonic stem cells requires either that the cells be further genetically modified to inhibit expression of certain cell surface markers, or that the use of chemotherapeutic immune suppressors continue in order to protect against transplant rejection. Thus, although embryonic stem cell research provides a promising alternative solution to the problem of a limited supply of organs for transplantation, the problems and risks associated with the need for immunosuppression to sustain transplantation of heterologous cells or tissue would remain. An estimated 20 immunologically different lines of embryonic stem cells would need to be established in order to provide immunocompatible cells for therapies directed to the majority of the population (Wadman, M., Nature (1999) 398: 551).

Using cells from the developed individual, rather than an embryo, as a source of autologous or allogeneic stem cells would overcome the problem of tissue incompatibility associated with the use of transplanted embryonic stem cells, as well as solve the ethical dilemma associated with embryonic stem cell research. The greatest disadvantage associated with the use of autologous stem cells for tissue transplant thus far lies in their limited differentiation potential. A number of stem cells have been isolated from fully-developed organisms, particularly humans, but these cells, although reported to be multipotent, have demonstrated limited potential to differentiate to multiple cell types.

Thus, even though stem cells with multiple differentiation potential have been isolated previously by others and by the present inventors, a progenitor cell with the potential to differentiate into a wide variety of cell types of different lineages, including fibroblasts, osteoblasts, chondrocytes, adipocytes, skeletal muscle, endothelium, stroma, smooth muscle, cardiac muscle and hemopoietic cells, has not been described. If cell and tissue transplant and gene therapy are to provide the therapeutic advances expected, a stem cell or progenitor cell with the greatest or most extensive differentiation potential is needed. What is needed is the adult equivalent of an embryonic stem cell.

SUMMARY OF THE INVENTION

The present invention provides an isolated multipotent mammalian stem cell that is surface antigen negative for CD44, CD45, and HLA Class I and II. The cell may also be surface antigen negative for CD34, Muc18, Stro-1, HLA-class-I and may be positive for oct3/4 mRNA, and may be positive for hTRT mRNA. In particular, the cell may be surface antigen negative for CD31, CD34, CD36, CD38, CD45, CD50, CD62E and CD62P, HLA-DR, Muc18, STRO-1, cKit, Tie/Tek, CD44, HLA-class I and 2-microglobulin and is positive for CD10, CD13, CD49b, CD49e, CDw90, Flk1, EGF-R, TGF-R1 and TGF-R2, BMP-R1A, PDGF-R1a and PDGF-R1b. The present invention provides an isolated multipotent non-embryonic, non-germ cell line cell that expresses transcription factors oct3/4, REX-1 and ROX-1. It also provides an isolated multipotent cell derived from a post-natal mammal that responds to growth factor LIF and has receptors for LIF.

The cells of the present invention described above may have the capacity to be induced to differentiate to form at least one differentiated cell type of mesodermal, ectodermal and endodermal origin. For example, the cells may have the capacity to be induced to differentiate to form cells of at least osteoblast, chondrocyte, adipocyte, fibroblast, marrow stroma, skeletal muscle, smooth muscle, cardiac muscle, endothelial, epithelial, hematopoietic, glial, neuronal or oligodendrocyte cell type. The cell may be a human cell or a mouse cell. The cell may be from a fetus, newborn, child, or adult. The cell may be derived from an organ, such as from marrow, liver or brain.

The present invention further provides differentiated cells obtained from the multipotent adult stem cell described above, wherein the progeny cell may be a bone, cartilage, adipocyte, fibroblast, marrow stroma, skeletal muscle, smooth muscle, cardiac muscle, endothelial, epithelial, endocrine, exocrine, hematopoietic, glial, neuronal or oligodendrocyte cell. The differentiated progeny cell may be a skin epithelial cell, liver epithelial cell, pancreas epithelial cell, pancreas endocrine cell or islet cell, pancreas exocrine cell, gut epithelium cell, kidney epithelium cell, or an epidermal associated structure (such as a hair follicle). The differentiated progeny cell may form soft tissues surrounding teeth or may form teeth.

The present invention provides an isolated transgenic multipotent mammalian stem cell as described above, wherein genome of the cell has been altered by insertion of preselected isolated DNA, by substitution of a segment of the cellular genome with preselected isolated DNA, or by deletion of or inactivation of at least a portion of the cellular genome. This alteration may be by viral transduction, such as by insertion of DNA by viral vector integration, or by using a DNA virus, RNA virus or retroviral vector. Alternatively, a portion of the cellular genome of the isolated transgenic cell may be inactivated using an antisense nucleic acid molecule whose sequence is complementary to the sequence of the portion of the cellular genome to be inactivated. Further, a portion of the cellular genome may be inactivated using a ribozyme sequence directed to the sequence of the portion of the cellular genome to be inactivated. The altered genome may contain the genetic sequence of a selectable or screenable marker gene that is expressed so that the progenitor cell with altered genome, or its progeny, can be differentiated from progenitor cells having an unaltered genome. For example, the marker may be a green, red, yellow fluorescent protein, Beta-gal, Neo, DHFR$^m$, or hygromycin. The cell may express a gene that can be regulated by an inducible promoter or other control mechanism to regulate the expression of a protein, enzyme or other cell product.

The present invention provides a cell that may express high levels of telomerase and may maintain long telomeres after extended in vitro culture, as compared to the telomeres from lymphocytes from the same donors. The telomeres may be about 11-16 KB in length after extended in vitro culture.

The present invention provides a cell differentiation solution comprising factors that modulate the level of oct3/4 expression for promoting continued growth or differentiation of undifferentiated multipotent stem cells.

The present invention provides a method for isolating multipotent adult stem cells (MASC). The method involves depleting bone marrow mononuclear cells of CD45⁺ glycophorin A⁺ cells, recovering CD45– glycophorin A– cells, plating the recovered CD45– glycophorin A– cells onto a matrix coating, and culturing the plated cells in media supplemented with growth factors. The step of depleting may involved negative selection using monoclonal or polyclonal antibodies. The growth factors may be chosen from PDGF-BB, EGF, IGF, and LIF. The last step may further involve culturing in media supplemented with dexamethasone, linoleic acid, and/or ascorbic acid.

The present invention provides a culture method for isolating multipotent adult stem cells involving adding the cells to serum-free or low-serum medium containing insulin, selenium, bovine serum albumin, linoleic acid, dexamethasone, and platelet-derived growth factor. The serum-free or low-serum medium may be low-glucose DMEM in admixture with MCDB. The insulin may be present at a concentration of from about 10 to about 50 µg/ml. The serum-free or low-serum medium may contain an effective amount of transferrin at a concentration of greater than 0 but less than about 10 µg/ml, the selenium may be present at a concentration of about 0.1 to about 5 µg/ml, the bovine serum albumin may be present at a concentration of about 0.1 to about 5 µg/ml, the linoleic acid may be present at a concentration of about 2 to about 10 µg/m, and the dexamethasone may be present at a concentration of about 0.005 to 0.15 µM. The serum-free medium or low-serum medium may contain about 0.05-0.2 mM L-ascorbic acid. The serum-free medium or low-serum medium may contain about 5 to about 15 ng/ml platelet-derived growth factor, 5 to about 15 ng/ml epidermal growth factor, 5 to about 15 ng/ml insulin-like growth factor, 10-10,000 IU leukemia inhibitory factor. The present invention further provides a cultured clonal population of mammalian multipotent adult stem cells isolated according to the above-described method.

The present invention provides a method to permanently and/or conditionally immortalize MASC derived cells and differentiated progeny by transferring telomerase into MASC or differentiated progeny.

The present invention provides a method to reconstitute the hematopoietic and immune system of a mammal by administering to the mammal fully allogenic multipotent stem cells (MASC), derived hematopoietic stem cells, or progenitor cells to induce tolerance in the mammal for subsequent multipotent stem cell derived tissue transplants or other organ transplants.

The present invention provides a method of expanding undifferentiated multipotent stem cells into differentiated hair follicles by administering appropriate growth factors, and growing the cells.

The present invention provide numerous uses for the above-described cells. For example, the invention provides a method of using the isolated cells by performing an in utero transplantation of a population of the cells to form chimerism of cells or tissues, thereby producing human cells in prenatal or post-natal humans or animals following transplantation, wherein the cells produce therapeutic enzymes, proteins, or other products in the human or animal so that genetic defects are corrected. The present invention also provides a method of using the cells for gene therapy in a subject in need of therapeutic treatment, involving genetically altering the cells by introducing into the cell an isolated pre-selected DNA encoding a desired gene product, expanding the cells in culture, and introducing the cells into the body of the subject to produce the desired gene product.

The present invention provides a method of repairing damaged tissue in a human subject in need of such repair by expanding the isolated multipotent adult stem cells in culture, and contacting an effective amount of the expanded cells with the damaged tissue of said subject. The cells may be introduced into the body of the subject by localized injection, or by systemic injection. The cells may be introduced into the body of the subject in conjunction with a suitable matrix implant. The matrix implant may provide additional genetic material, cytokines, growth factors, or other factors to promote growth and differentiation of the cells. The cells may be encapsulated prior to introduction into the body of the subject, such as within a polymer capsule.

The present invention provides a method for inducing an immune response to an infectious agent in a human subject involving genetically altering an expanded clonal population of multipotent adult stem cells in culture express one or more pre-selected antigenic molecules that elicit a protective immune response against an infectious agent, and introducing into the subject an amount of the genetically altered cells effective to induce the immune response. The present method may further involve, prior to the second step, the step of differentiating the multipotent adult stem cells to form dendritic cells.

The present invention provides a method of using MASCs to identify genetic polymorphisms associated with physiologic abnormalities, involving isolating the MASCs from a statistically significant population of individuals from whom phenotypic data can be obtained, culture expanding the MASCs from the statistically significant population of individuals to establish MASC cultures, identifying at least one genetic polymorphism in the cultured MASCs, inducing the cultured MASCs to differentiate, and characterizing aberrant metabolic processes associated with said at least one genetic polymorphism by comparing the differentiation pattern exhibited by an MASC having a normal genotype with the differentiation pattern exhibited by an MASC having an identified genetic polymorphism.

The present invention further provides a method for treating cancer in a mammalian subject involving genetically altering multipotent adult stem cells to express a tumoricidal protein, an anti-angiogenic protein, or a protein that is expressed on the surface of a tumor cell in conjunction with a protein associated with stimulation of an immune response to antigen, and introducing an effective anti-cancer amount of the genetically altered multipotent adult stem cells into the mammalian subject.

The present invention provides a method of using MASCs to characterize cellular responses to biologic or pharmacologic agents involving isolating MASCs from a statistically significant population of individuals, culture expanding the MASCs from the statistically significant population of individuals to establish a plurality of MASC cultures, contacting the MASC cultures with one or more biologic or pharmacologic agents, identifying one or more cellular responses to the one or more biologic or pharmacologic agents, and comparing the one or more cellular responses of the MASC cultures from individuals in the statistically significant population.

The present invention also provides a method of using specifically differentiated cells for therapy comprising administering the specifically differentiated cells to a patient in need thereof. It further provides for the use of genetically engineered multipotent stem cells to selectively express an endogenous gene or a transgene, and for the use of MASCs grown in vivo for transplantation/administration into an animal to treat a disease. For example, neuroretinal cells derived from multipotent stem or MASCs can be used to treat blindness caused by among other things but not limited to neuroretinal disease caused by among other things macular degeneration, diabetic retinopathy, glaucoma, retinitis pigmentosa. The cells can be used to engraft a cell into a mammal comprising administering autologous, allogenic or xenogenic cells, to restore or correct tissue specific metabolic, enzymatic, coagulation, structural or other function to the mammal. The cells can be used to engraft a cell into a mammal, causing the differentiation in vivo of cell types, and for administering the differentiated stem cells into the mammal. The cells, or their in vitro or in vivo differentiated progeny, can be used to correct a genetic disease, degenerative disease, cardiovascular disease, metabolic storage disease, neural, or cancer disease process. They can be used to produce gingiva-like material for treatment of periodontal disease. They can be used to develop skin epithelial tissue derived from multipotent stem cells that can be utilized for skin grafting and plastic surgery. They could be used to enhance muscle such as in the penis or heart. The can be used to produce blood ex vivo for therapeutic use, or to produce human hematopoietic cells and/or blood in prenatal or post natal animals for human use. They can be used as a therapeutic to aid for example in the recovery of a patient from chemotherapy or radiation therapy in treatment of cancer, in the treatment of autoimmune disease, to induce tolerance in the recipient. They can be used to treat AIDS or other infectious diseases.

The cardiomyocytes or MASC can be used to treat cardiac diseases including among others but not limited to myocarditis, cardiomyopathy, heart failure, damage caused by heart attacks, hypertension, atherosclerosis, heart valve dysfunction. A genetically engineered multipotent mammalian derived stem cell, or its differentiated progeny, can be used to treat a disease with CNS deficits or damage. Further the multipotent mammalian derived stem cell, or its neuronally related differentiated cell, can be used to treat a disease with neural deficits or degeneration including among but not limited to stroke, Alzhemier's, Parkinson's disease, Huntington's disease, AIDS associated dementia, spinal cord injury, metabolic diseases effecting the brain or other nerves.

A multipotent mammalian derived stem cell or their differentiated progeny such as stromal cells can be used to support the growth and differentiation of other cell types in vivo or in vitro, including but not limited to hematopoietic cells, pancreatic islet or beta cells, hepatocytes, etc. The stem cell, or cartilage differentiated progeny, can be used to treat a disease of the joints or cartilage including but not limited to cartilage tears, cartilage thinning, osteoarthritis. Moreover, the stem cells or their osteoblast differentiated progeny can be used to ameliorate a process having deleterious effects on bone including among but not limited to bone fractures, non-healing fractures, osteoarthritis, "holes" in bones cause by tumors spreading to bone such as prostate, breast, multiple myloma etc.

The present invention also provides a kit for providing immunization to induce a protective immune response in a human subject. The kit may contain, separately packaged, media and antibodies for isolation of multipotent adult stem cells from a bone marrow aspirate; media and cellular factors for culture of the isolated multipotent adult stem cells; and genetic elements for genetically altering the multipotent adult stem cells to produce antigenic molecules. The kit may further contain media and cellular factors effective to differentiate the multipotent adult stem cells to form tissue-specific cell types. The genetic elements may be viral vectors, and the viral vectors may contain the nucleotide sequence encoding one or more antigens of bacterial or viral origin. The genetic elements may be plasmids containing a nucleotide sequence encoding a bacterial, viral, or parasite antigen. The plasmids may be packaged with components for calcium phosphate transfection. The genetic elements may be vectors comprising nucleotide sequences encoding antigens common to cancer cells, or the genetic elements may be vectors containing nucleotide sequences encoding antigens of parasitic organisms.

The present invention further provides a method of gene profiling of a multipotent derived stem cell as described above, and the use of this gene profiling in a data bank. It also provides for the use of gene profiled multipotent stem cells as described above in data bases to aid in drug discovery.

BRIEF DESCRIPTION OF THE DRAWINGS

(FIG. 1b).

Figure 1B:
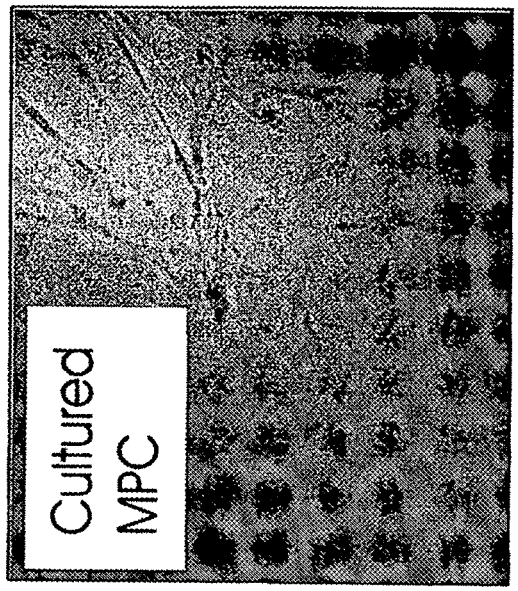
FIG. 1a and FIG. 1b are photographs of undifferentiated MASCs of the present invention. Cells lacking CD45 expression, as well as glycophorin-A expression were selected by immunomagnetic bead depletion and FACS. Cells recovered after sorting are small blasts (FIG. 1a). 5000 cells were plated in fibronectin coated wells of 96 well plates in defined medium consisting of DMEM, 10 ng/ml IGF, 10 ng/ml EGF and 10 ng/ml PDGF-BB as well as transferrin, selenium, bovine serum albumin, dexamethasone, linoleic acid, insulin and ascorbic acid. After 7-21 days, small colonies of adherent cells develop.

In panel C, confluent MASCS were exposed to retinoic acid and then cultured in serum-free medium with 100 ng/mL bFGF. Cells were then analyzed by Western blot. Gata4 and Gata6 were expressed as early as day 2 and persisted till day 15. Cardiac troponin-T was expressed after day 4 and cardiac troponin-I from day 6 on, while we could detect ANP after day 11 (not shown). These cardiac proteins were detected in >70% of cells by immuno-histochemistry on day 15 (not shown). We found the transcription factor Myf6 from day 2 on. Expression of desmin started on day 6 and myogenin on day 2. We also found skeletal actin. When the cultures were maintained for >3 weeks, cells formed syncithia. We also saw infrequent spontaneous contractions occurring in the cultures, which were propagated over several mm distance.

Figure 8:
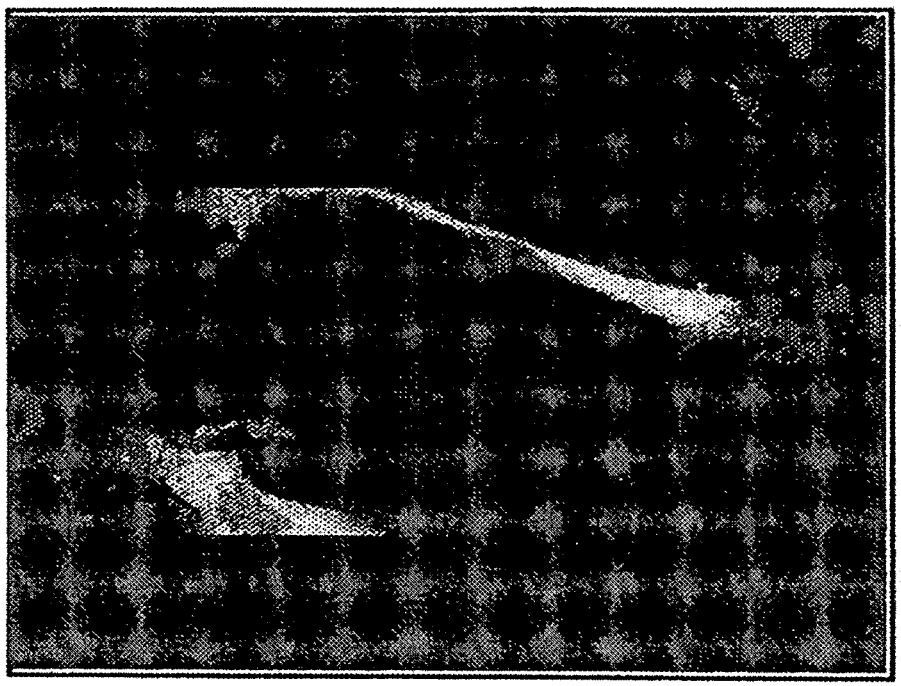

FIG. 8 is a photomicrograph showing fusion of myoblasts and myotubes to form multinucleated myotubes. Myoblasts from an eGFP transduced population of MASC subsequently induced with 5-azacytidin for 24 and maintained in MASC expansion medium were cocultured with myoblasts generated from non e-GFP transduced MASCS from the same donor. To induce myotubes, MASC derived myoblasts 9 obtained after induction of non-transduced MASC with 5-azacytidin for 24 h after which they were maintained in MASC expansion medium for 14 days) were cultured with 10% horse serum in DMEM. Once multinucleated cells were formed, myotubes were incubated with PKH26 (a red membrane dye), washed and cocultured with eGFP transduced myotubes generated as described above in the presence of 10% horse serum. After 2 days, cells were examined under an fluorescence microscope. The photomicrograph shows that the eGFP positive myoblast has fused with the PKH26 labeled myotube.

Figure 9:
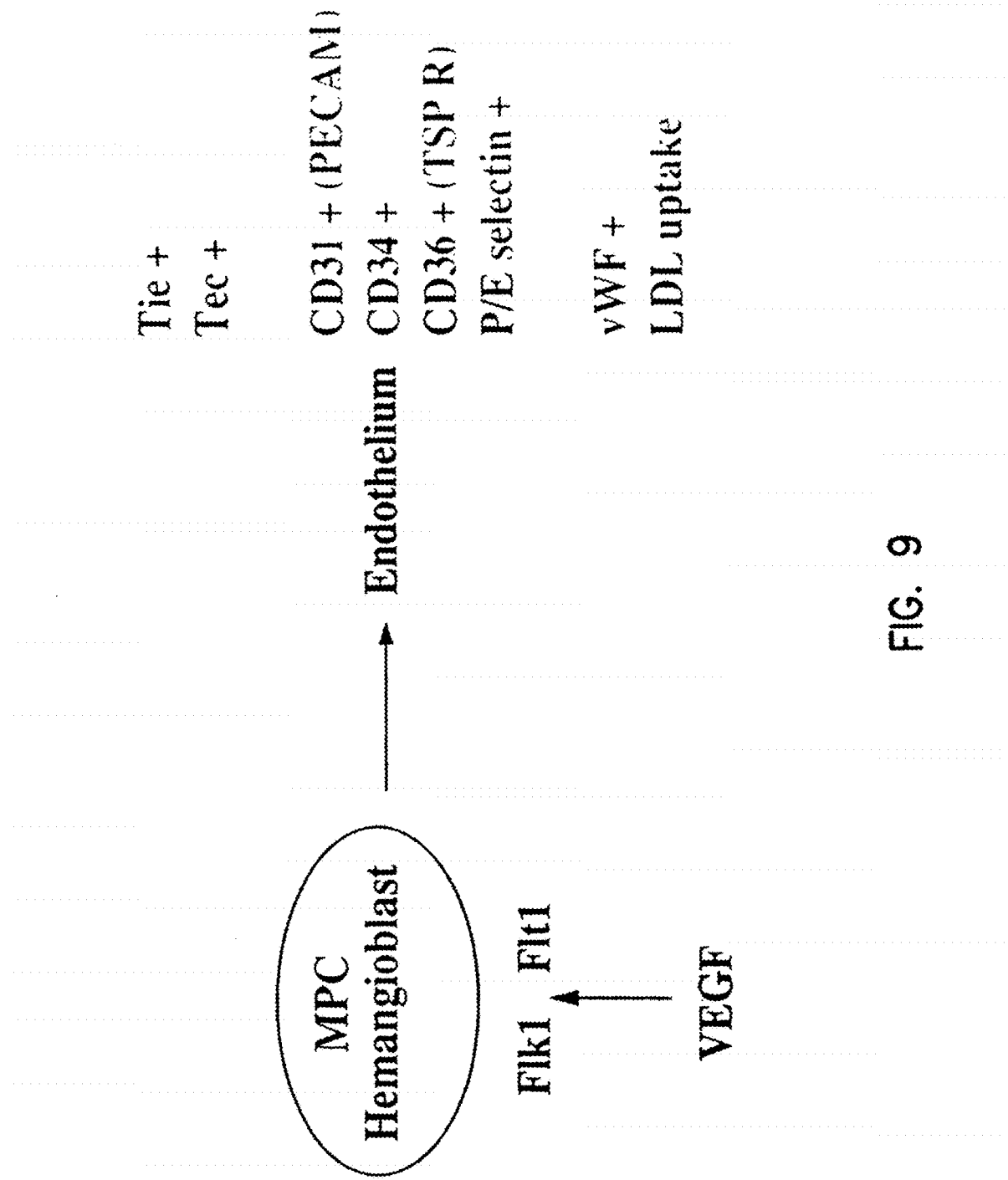

FIG. 9 is a cartoon depicting methods used by the inventors to induce endothelium differentiation from MASCs of the present invention and markers used to detect endothelium differentiation.

Figure 10:
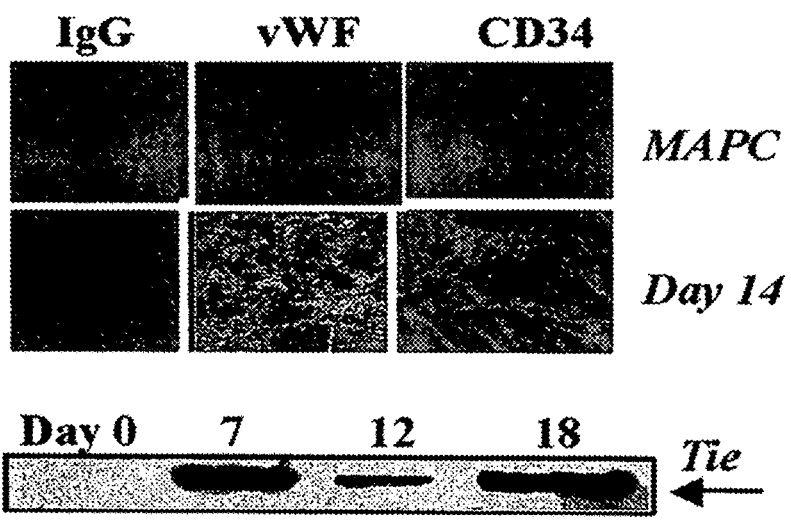

FIG. 10 is a series of photographs of immunofluorescence staining for von Willebrand factor and CD34 markers as well as a Western blot analysis for the endothelial cell surface receptor Tie/Tek to confirm endothelial cell differentiation. MASCs express Flk1 but not CD34, PECAM, E- and P-selectin, CD36, Tie/Tek or Flt1. When MASCs were cultured serum-free MASCs medium with 20 ng/mL VEGF we saw the appearance of CD34 on the cell surface and cells expressed vWF by day 14 (immuno-fluorescence). In addition, cells expressed Tie/Tek, as shown on Western blot analysis on days 7, 11 and 14. When VEGF induced cells were cultured on matrigel or collagen type IV, vascular tube formation was seen.

Figure 11:
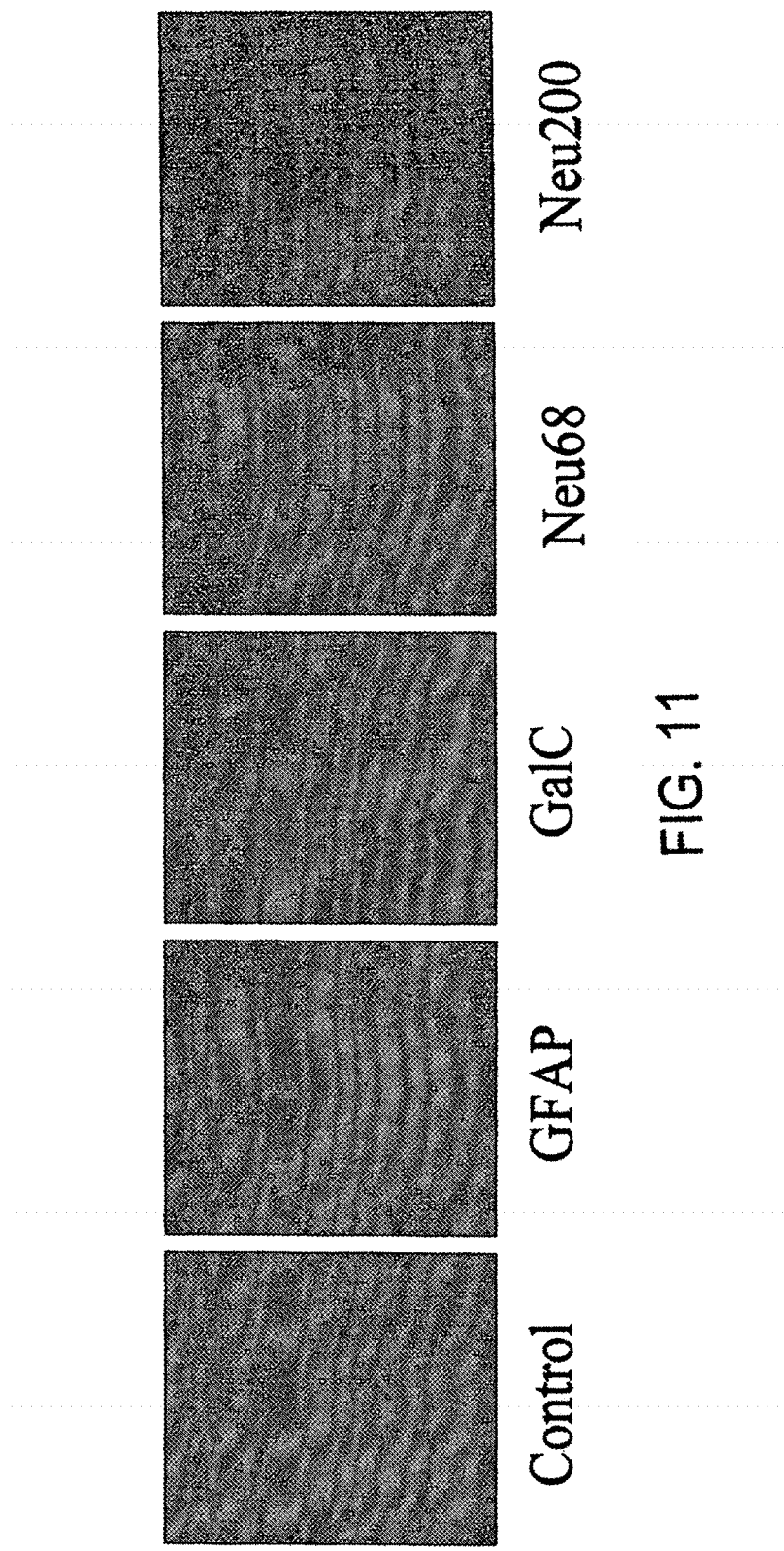

FIG. 11 is a series of photomicrographs showing that MASCs differentiate to astrocytes, oligodendrocytes and neural cells when cultured with SCF, Flt3-L, Tpo and Epo for 14 days after which they were cultured in SCF and EGF containing MASC medium by the hematopoietic supportive feeder AFT024. Cells were labeled with antibodies against glial-fibrilar-acidic-protein (GFAP) (astrocytes), galactocerebroside (GalC) (oligodendrocytes) and neurofilament-68 and 200 (neurons).

Figure 12:
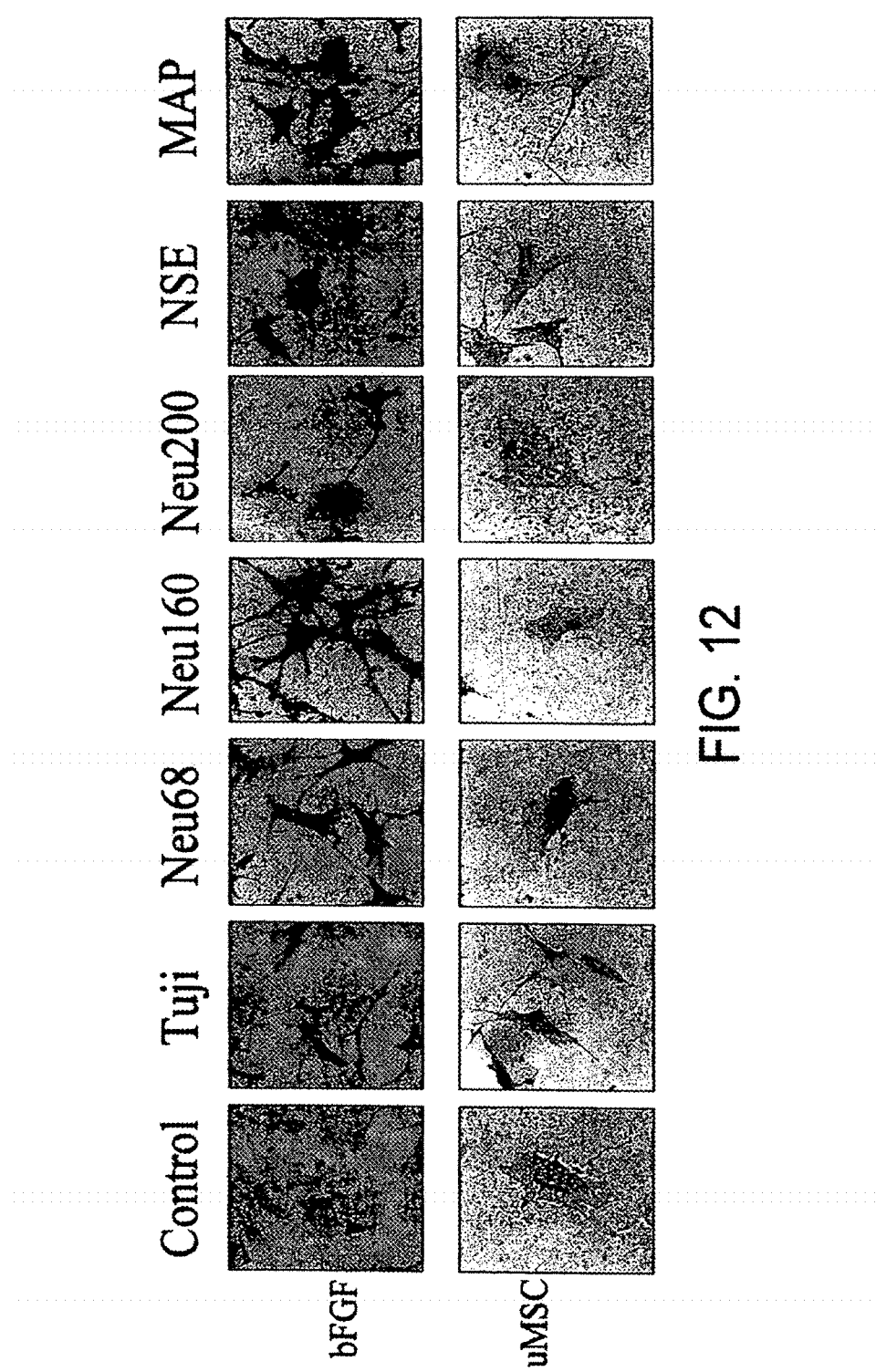

FIG. 12 is a series of photomicrographs showing that when low density MASCs are cultured in fibronectin coated wells with 100 ng/mL bFGF, neurons develop. 20±2% cells stained positive for β-tubulin-III, 22±3% for neurofilament-68, 50±3% for neurofilament-160, 20±2% for neurofilament-200, 82±5% for neuron-specific-enolase (NSE) and 80±2% for microtubule-assocaited-protein-2 (MAP2). The number of neurites per neuron increased from 3±1, to 5±1 and 7±2 from 2, 3 to 4 weeks after differentiation. Not shown, after 2 weeks in culture, 26±4% of cells were GFAP positive, 28±3% GalC positive, whereas fewer cells were GFAP or GalC positive after 4 weeks.

Figure 13:
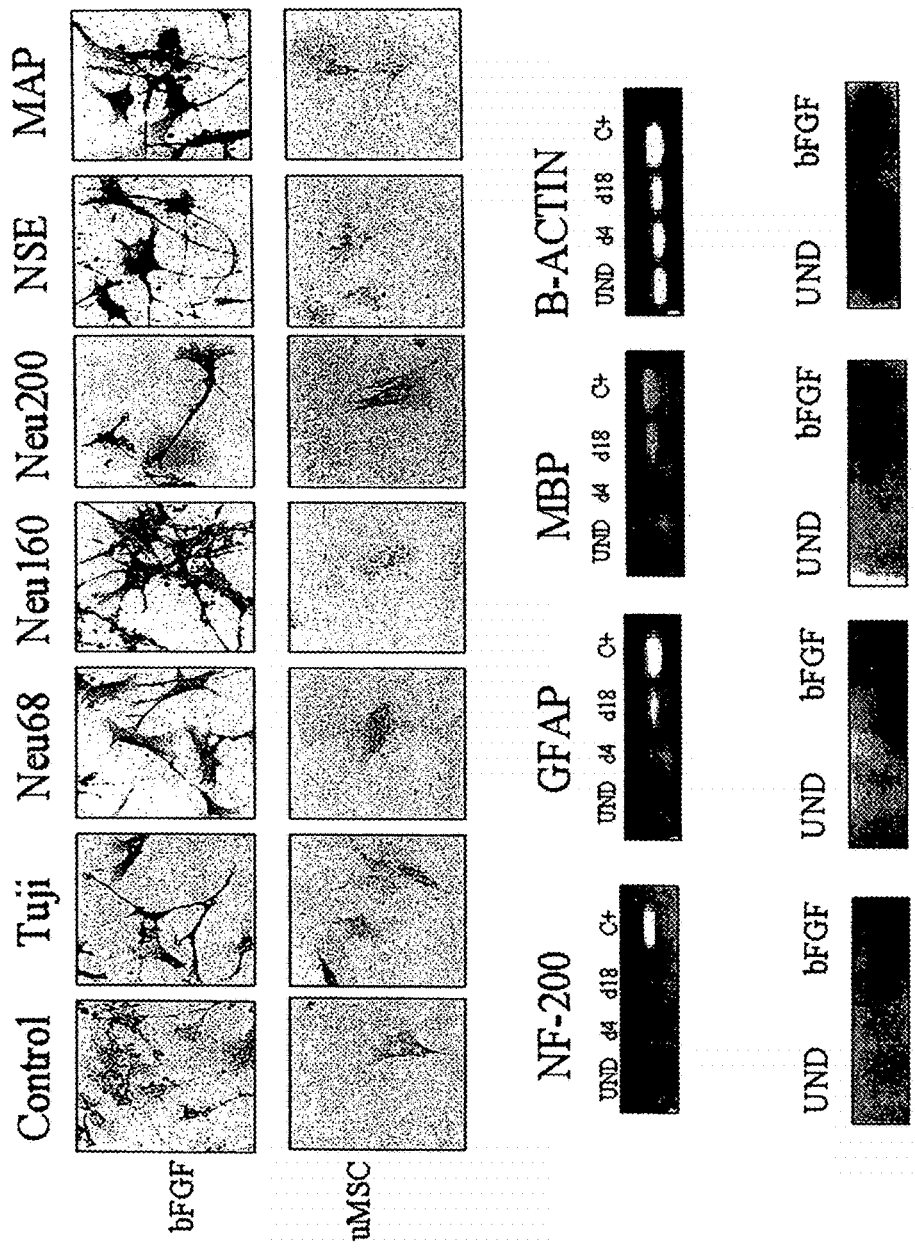

FIG. 13 shows RT-PCR results and Western blot analysis for GFAP, myelin basic protein (MBP) and neurofilament-200x, x and days after induction of MASCs with bFGF.

Figure 14:
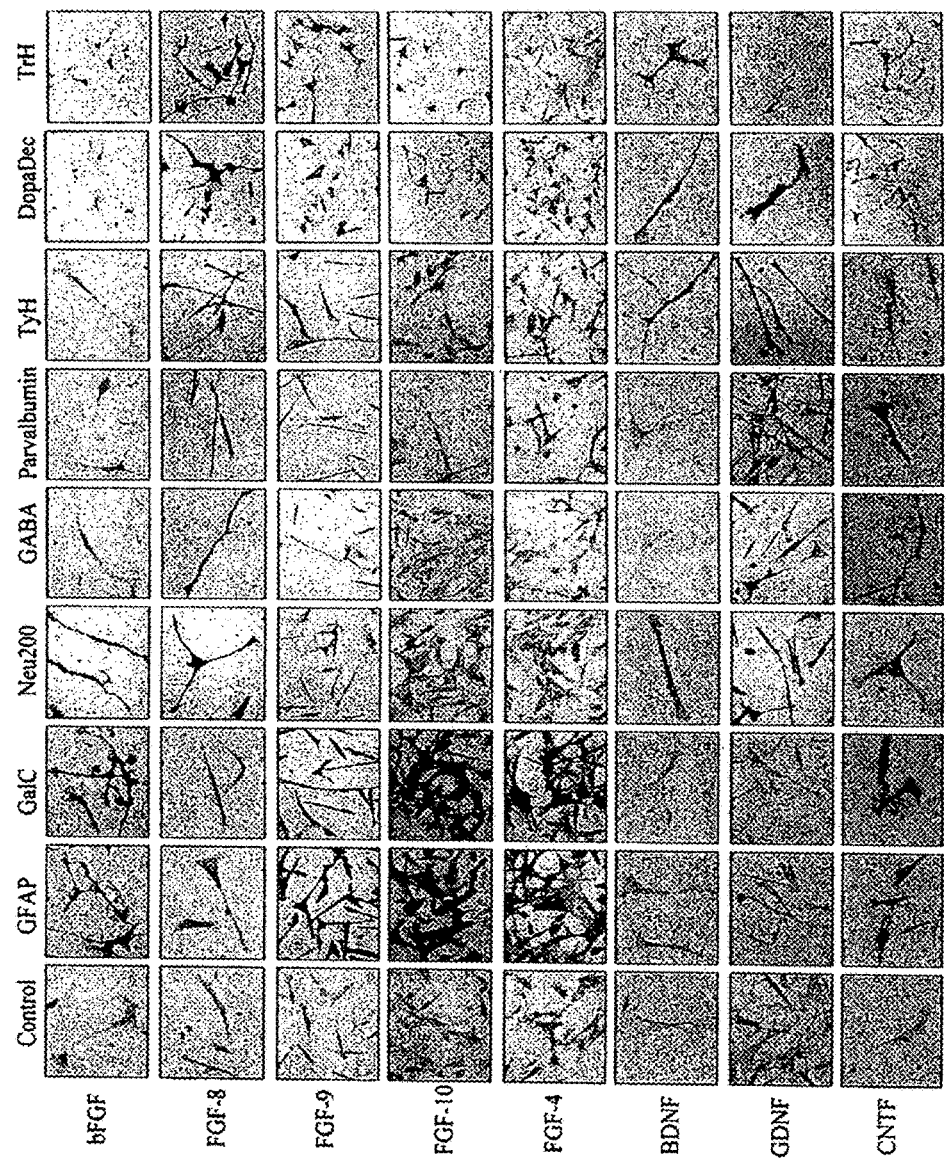

FIG. 14 shows effect of 100 ng/mL bFGF, or 10 ng/mL of either FGF-9, FGF-8, FGF-10, FGF-4, BDNF, GDNF, or CNTF on neural development from MASCs. The nature of the differentiated cells was identified by immunohistochemistry using antibodies agiants GFAP, GalC, neurofilament 200, tyrosine hydroxylase (TH), GABA and parvalbumine, and acetylcholine (CAT). When cultured for 3 weeks with bFGF, MASC differentiated into neurons, astrocuytes and oligodendrocytes. We did not detect GABA, parvalbumin, tyrosine hydroxylase, DOPA-decarboxylase, or tryptophan hydroxylase. When cultured for 3 weeks with long/mL FGF-9 and EGF MASCs generated astrocytes, oligodendrocytes and GABAergic and dopaminergic. When MASCs were cultured with 10 ng/mL FGF-8 and EGF for 3 weeks both dopaminergic and GABAergic neurons were produced. Culture of MASCs in 10 ng/mL FGF-10 and EGF for three weeks generated astrocytes and oligodendrocytes, but not neurons. When treated with 10 ng/mL FGF-4 and EGF for 3 weeks MASCs differentiated into astrocytes and oligodendrocytes but not neurons. When MASCs were treated with 10 ng/mL BDNF and EGF exclusive differentiation into tyrosine hydroxylase positive neurons was seen. When cultured with GDNF MASCs differentiated into GABAergic and dopaminergic neurons. When cultured with exclusive differentiation into GABAergic neurons was seen after three weeks.

Figure 15:
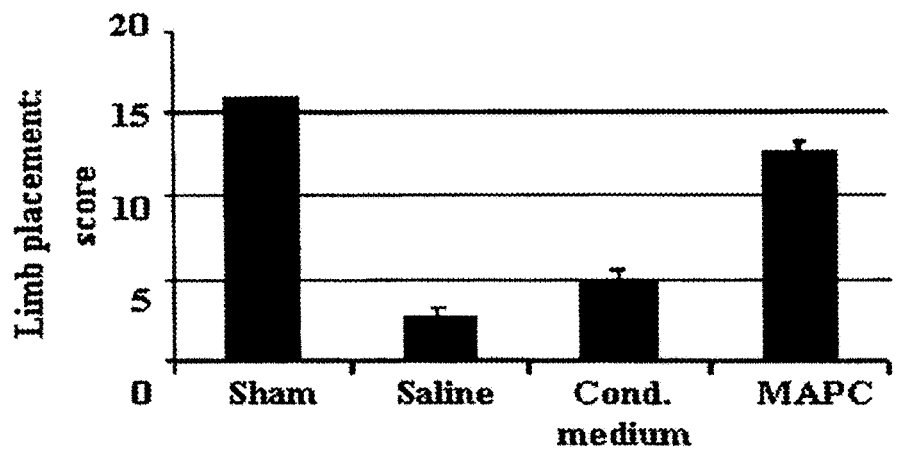

FIG. 15. Undifferentiated MASCs were implanted around a parietal infarct caused by ligation of middle cerebral artery in the brain of Wistar rats. Rats were maintained on cyclosporin and function of the paralyzed limbs examined 6 weeks after injection of the MASCs. As control, animals received saline injections or media conditioned by MASCs. Results are shown for limb placement testing 6 weeks after transplantation of the MASCs or control solutions. Functional improvement to levels equivalent to that of sham animals was only seen in rats transplanted with MASCS.

Figure 16:
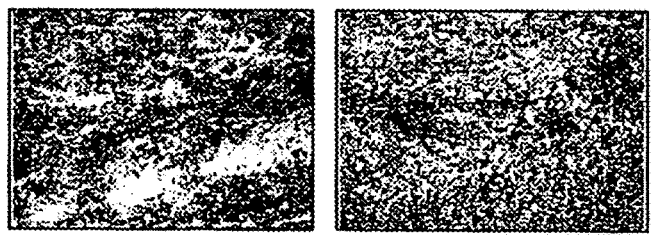

FIG. 16 Undifferentiated MASCs were implanted around a parietal infarct caused by ligation of middle cerebral artery in the brain of Wistar rats. Rats were maintained on cyclosporin and function of the paralyzed limbs examined 6 weeks after injection of the MASCs. After 2 and 6 weeks, animals were sacrificed to determine neural phenotype. Because of autofluorescence of the brain following transplantation with eGFP$^+$ cells, we had to resort to immunohistochemical analysis of the graft. The majority of eGFP$^+$ cells were detected in the grafted area itself at 2 weeks. After 6 weeks, eGFP$^+$ cells migrated outside the graft. At 2 weeks, cells staining with an anti-eGFP antibody remained spherical in nature and ranged from 10-30 µm in diameter. After 6 weeks, eGFP$^+$ cells were significantly smaller and neurites could be seen in the grafted area, extending out to the normal brain tissue. Presence of human cells was confirmed by staining with a human specific nuclear antibody, NuMa (not shown). This antibody will in the future be used to identify human cells in the graft allowing double and triple staining with immunofluorescent antibodies. Using human specific anti-nestin antibodies, we detected small clusters of nestin-positive cells in the same location of the graft as the NuMa-positive cells and GFP$^+$ cells, suggestive of neuroectodermal differentiation. In addition, we found positive staining for β-tubulin III and Neurofilament-68 and -160, Oligo Marker and GFAP, suggesting differentiation to neuronal and glial cells.

Figure 17:
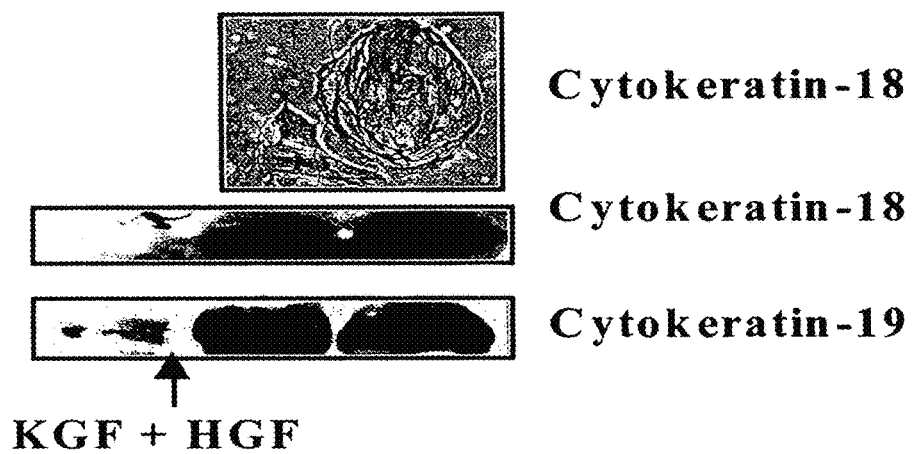

FIG. 17 shows immunohistochemical and Western blot analysis for cytokeratin 18 and 19 after MASCs were treated with HGF and KGF. After 14 days, large epithelioid cells could be seen that expressed cytokeratin 18 and 19.

DETAILED DESCRIPTION OF THE INVENTION

Whether stem cells that are committed to a certain lineage have the ability of undergoing a genetical re-programming similar to what occurs in the "cloning process" or "transdifferentiate" is not known. The present inventors have shown that multipotent stem cells persist even after birth in multiple organs (such as marrow, liver, brain) when purified from these organs and cultured in vitro can proliferate without obvious senescence and can differentiate into multiple cell types, different from the tissues they were derived from. The phenotype of stem cells derived from different organs with "plasticity" is similar (CD45$^-$CD44$^-$HLA-DR$^-$HLA-calss I$^-$oct3/4 mRNA$^+$ and hTRT$^+$). In addition, the characteristics of such stem cells are similar to that of, for instance, primordial germ cells from which they may be a direct descendant.

The present inventors have evidence that a small fraction of marrow cells, as well as cells in brain and liver, express genes commonly only found in ES or EG cells (oct-4, Rex-1). Furthermore, the present inventors have detected eGFP+ cells in marrow and brain of newborn mice transgenic for the oct-4/eGFP construct, further demonstrating that oct-4 expressing cells are present in tissues other than germ cells in post-embryonic life. Therefore, a small number of stem cells may persist throughout an adult, living in different organs that have multipotent characteristics. This explains the perceived plasticity of stem cells derived from multiple organs.

Selection and Phenotype of Multipotent Adult Stem Cells

The present invention provides multipotent adult stem cells (MASCs), isolated from human or mouse (and other species) adults, newborns, or fetuses, that can differentiate to form bone cells, cartilage, adipocytes, fibroblasts, bone marrow stromal cells, skeletal muscle, smooth muscle, cardiac muscle, endothelium, epithelial cells (keratinocytes), hemopoietic, glial, neuronal and oligodendrocyte progenitor cells. These cells exhibit differentiation phenotypes more akin to an embryonic stem cell than to any adult-derived stem cell described to date.

The multipotent adult stem cells described herein were isolated by the method developed by the inventors, who identified a number of specific cell surface markers that characterize the MASCs. The method of the present invention can be used to isolate multipotent adult stem cells from any adult, child, or fetus, of human, murine and other species origin. In addition, in mouse, these cells have been isolated from brain and liver. It is therefore now possible for one of skill in the art to obtain bone marrow aspirates, brain or liver biopsies, and possibly other organs, and isolate the cells using positive or negative selection techniques known to those of skill in the art, relying upon the surface markers expressed on these cells, as identified by the inventors, without undue experimentation.

Figure 1A:
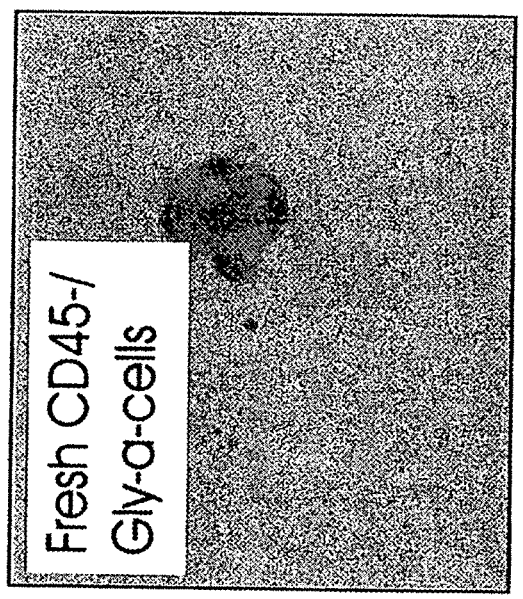

A. MASCs from Human Marrow:

To select the multipotent adult stem cells, bone marrow mononuclear cells are derived from bone marrow aspirates, which can be obtained by standard means known to those of skill in the art (see, for example, Muschler, G. F., et al., *J. Bone Joint Surg. Am.* (1997) 79(11): 1699-709, Batinic, D., et al., *Bone Marrow Transplant.* (1990) 6(2):103-7). The multipotent adult stem cells are present within the bone marrow (or other organs such as liver or brain) but do not express the common leukocyte antigen CD45 or erythroblast specific glycophorin-A (Gly-A). The mixed population of cells is subjected to a Ficoll Hypaque separation. Cells are then subjected to negative selection using anti-CD45 and anti-Gly-A antibodies, depleting the population of CD45$^+$ and Gly-A$^+$ cells, and recovering the remaining approximately 0.1% of marrow mononuclear cells. Cells can also be plated in fibronectin coated wells and cultured as described below for 2-4 weeks after which the cells are depleted of CD45$^+$ and Gly-A$^+$ cells. Alternatively, positive selection is used to isolate cells using a combination of cell-specific markers identified by the inventors and described herein, such as the leukemia inhibitory factor (LIF) receptor. Both positive and negative selection techniques are known to those of skill in the art, and numerous monoclonal and polyclonal antibodies suitable for negative selection purposes are also known in the art (see, for example, *Leukocyte Typing V*, Schlossman, et al., Eds. (1995) Oxford University Press) and are commercially available from a number of sources. Techniques for mammalian cell separation from a mixture of cell populations have also been described by Schwartz, et al., in U.S. Pat. No. 5,759,793 (magnetic separation), Basch, et al., *J. Immunol. Methods* (1983) 56: 269 (immunoaffinity chromatography), and Wysocki and Sato, *Proc. Natl. Acad. Sci. (USA)* (1978) 75: 2844 (fluorescence-activated cell sorting). (FIG. 1A) Recovered CD45$^-$/GlyA$^-$ cells are plated onto culture dishes coated with 5-115 ng/ml (preferably about 7-10 ng/ml) serum fibronectin or other appropriate matrix coating. Cells are maintained in Dulbecco Minimal Essential Medium (DMEM) or other appropriate cell culture medium, supplemented with 1-50 ng/ml (preferably about 5-15 ng/ml) platelet-derived growth factor-BB (PDGF-BB), 1-50 ng/ml (preferably about 5-15 ng/ml) epidermal growth factor (EGF), 1-50 ng/ml (preferably about 5-15 ng/ml) insulin-like growth factor (IGF), or 100-10,000 IU (preferably about 1,000 IU) LIF, with $10^{-10}$ to $10^{-8}$ M dexamethasone or other appropriate steroid, 2-10 µg/ml linoleic acid, and 0.05-0.15 µM ascorbic acid. Other appropriate media include, for example, MCDB, MEM, IMDM, and RPMI. Cells can either be maintained without serum, in the presence of 1-2% fetal calf serum, or, for example, in 1-2% human AB serum or autologous serum. (FIG. 1B)

The present inventors have shown that MASCs cultured at low density express the LIF-R, and these cells do not or minimally express CD44 whereas cells cultured at high density, that have characteristics of MSC, loose expression of LIF-R but express CD44. 1-2% CD45$^-$GlyA$^-$ cells are CD44$^-$ and <0.5% CD45$^-$GlyA$^-$ cells are LIF-R$^+$. FACS selected cells were subjected to quantitative RT-PCR (real time PCR) for oct-4 mRNA. oct-4 mRNA levels were 5 fold higher in CD45$^-$GlyA$^-$CD44$^-$ and 20-fold higher in CD45$^-$GlyA$^-$LIF-R$^+$ cells than in unsorted CD45$^-$GlyA$^-$ cells. Sorted cells were plated in MASC culture with 10 ng/mL EGF, PDGF-BB and LIF. The frequency with which MASC started growing was 30-fold higher in CD45$^-$GlyA$^-$LIF-R$^+$ cells and 3 fold higher in CD45$^-$GlyA$^-$CD44$^-$ cells than in unsorted CD45$^-$GlyA$^-$ cells.

Figure 2:
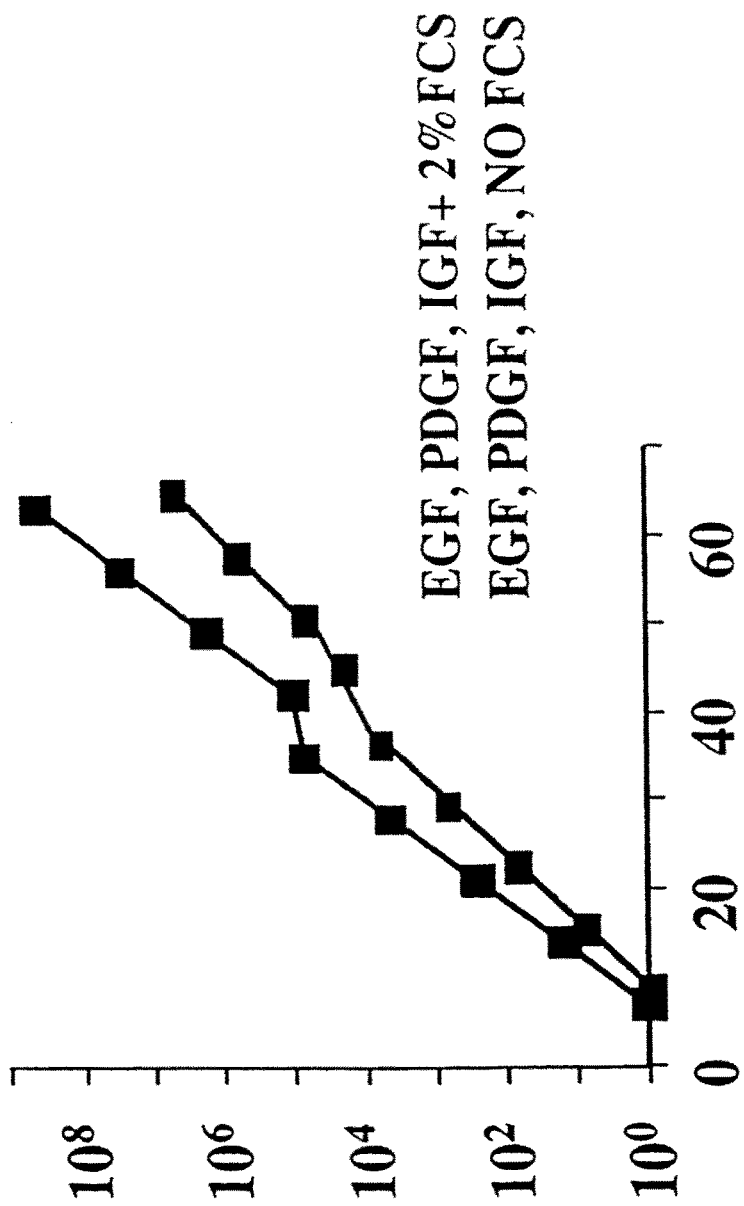
FIG. 2 is a graph illustrating expansion rates for MASCs in culture. CD45−/GlyA− cells were plated in fibronectin-coated wells of 96 well plates in defined medium consisting of DMEM, 10 ng/ml IGF, 10 ng/ml EGF and 10 ng/ml PDGF-BB as well as transferrin, selenium, bovine serum albumin, dexamethasone, linoleic acid, insulin and ascorbic acid with or without 2% FCS. When semi-confluent, cells were recovered by trypsinization and sub-cultured twice weekly at a 1:4 dilution under the same culture conditions.

When human cells are re-seeded at <0.5×10$^3$ cells/cm$^2$, cultures grow poorly and die. When re-seeded at >10×10$^3$ cells/cm$^2$ every 3 days, cells stop proliferating after <30 cell doublings and, as will be discussed below, this also causes loss of differentiation potential. When re-seeded at 2×10$^3$ cells/cm$^2$ every 3 days, >40 cell doublings can routinely be obtained, and some populations have undergone >70 cell doublings. Cell doubling time was 36-48 h for the initial 20-30 cell doublings. Afterwards cell-doubling time was extended to as much as 60-72 h. (FIG. 2)

Figure 3:
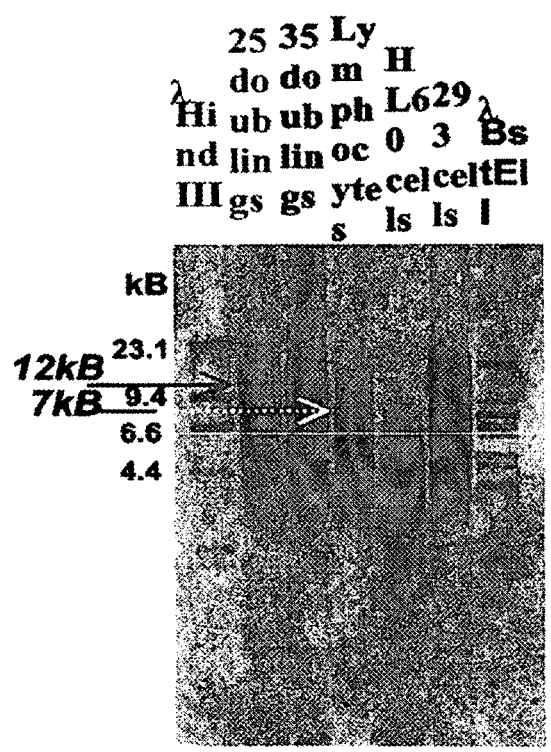
FIG. 3 Telomere length of MASCS from a donor, age 35, was cultured at reseeding densities of $2 \times 10^3$ cells/cm$^2$ for 23 and 35 cell doublings. Telomere length was determined using standard techniques. Telomere length was 9 kB. This was 3 kB longer than telomere length of blood lymphocytes obtained from the same donor. Telomere length evaluated after 10 and 25 cell doublings resp. and again after 35 cells doublings, was unchanged. As controls, we tested HL60 cells (short telomeres) and 293 cells (long telomeres).
Figure 4:
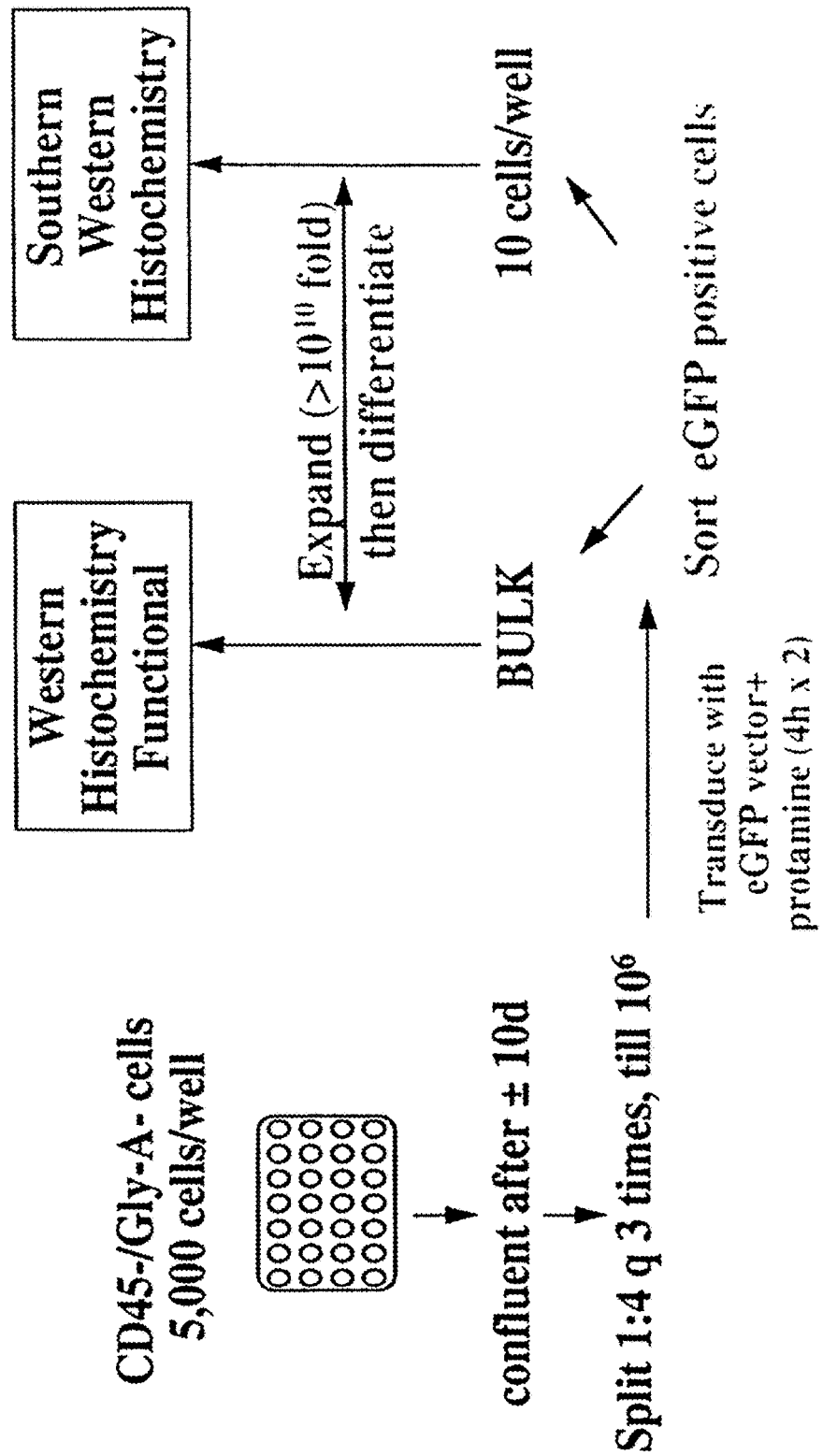
FIG. 4 illustrates the general protocol for culture, transduction, differentiation, and confirmation of differentiation used by the inventors for MASCs of the present invention. Transduction with an eGFP-containing retroviral vector was performed after culture as indicated. Half-confluent MASC were exposed for six hours on two sequential days to MFG-eGFP containing PA317 supernatant made in MASC medium (i.e., DMEM, 2% FCS, EGF, PDGF-BB, transferrin, selenium, bovine serum albumin, dexamethasone, linoleic acid, insulin and ascorbic acid) in the presence of 10 µg/mL protamine. Twenty-four hours after the last transduction, cells were trypsinized and subjected to FACS selection. Thirty to seventy percent of MASCs were eGFP positive. One to one hundred eGFP positive cells/well were sorted using the ACDU device on the FACS in FN coated wells of 96 well plates, in the same MASC medium. Of these wells, approximately 2/plate containing 10 cells/well produced MASC progeny. Clones were then culture expanded. Eight to 10 sub-populations of these expanded cells were induced to differentiate along different pathways, with differentiation being confirmed using the techniques indicated.

Telomere length of MASCs from 5 donors (age 2 years-55 years) cultured at reseeding densities of 2×10$^3$ cells/cm$^2$ for 23-26 cell doublings was between 11-13 kB. This was 3-5 kB longer than telomere length of blood lymphocytes obtained from the same donors. Telomere length of cells from 2 donors evaluated after 23 and 25 cell doublings resp. and again after 35 cells doublings, was unchanged. The karyotype of these MASCS was normal. (FIG. 3)

B. MASCs from Murine Tissues:

Marrow from C57/BL6 mice was obtained and mononuclear cells or cells depleted of CD45 and GlyA positive cells plated under the same culture conditions used for human MASCs (10 ng/mL human PDGF-BB and EGF). When marrow mononuclear cells were plated, we depleted CD45$^+$ cells 14 days after initiation of culture to remove hemopoietic cells. As for human MASCs, cultures were re-seeded at 2,000 cells/cm$^2$ every 2 cell doublings. In contrast to what we saw with human cells, when fresh murine marrow mononuclear cells depleted on day 0 of CD45$^+$ cells were plated in MASCs culture, no growth was seen. When murine marrow mononuclear cells were plated, and cultured cells 14 days later depleted of CD45$^+$ cells, cells with the morphology and phenotype similar to that of human MASCs appeared. When cultured with PDGF-BB and EFG alone, cell doubling was slow (>6 days) and cultures could not be maintained beyond 10 cell doublings. Addition of 100-10, 000 ng/mL (preferably 1,000 IU) LIF significantly improved cell growth and >70 cell doublings have been obtained.

Marrow, brain or liver mononuclear cells from 5-day old FVB/N mice were plated in MASCs cultures with EGF, PDGF-BB and LIF on fibronectin. 14 days later, CD45$^+$ cells were removed and cells maintained in MASCs culture conditions as described above. Cells with morphology and phenotype similar to that of human MASCs and murine marrow C57/B16 MASCs grew in cultures initiated with marrow, brain or liver cells from FVB/N mice.

C. Phenotype of MASCs.

1. Human MASCs.

Immunophenotypic analysis by FACS of human MASCs obtained after 22-25 cell doublings showed that cells do not express CD31, CD34, CD36, CD38, CD45, CD50, CD62E and -P, HLA-DR, Muc18, STRO-1, cKit, Tie/Tek; and express low levels of CD44, HLA-class I, and β2-microglobulin, but express CD10, CD13, CD49b, CD49e, CDw90, Flk1 (N>10).

Once cells undergo >40 doublings in cultures re-seeded at 2×10$^3$/cm$^2$, the phenotype becomes more homogenous and no cell expressed HLA-class-I or CD44 (n=6). When cells were grown at higher confluence, they expressed high levels of Muc18, CD44, HLA-class I and β2-microglobulin, which is similar to the phenotype described for MSC (N=8) (Pittenger, Science (1999) 284: 143-147).

Immunhistochemistry showed that human MASCs grown at 2×10$^3$/cm$^2$ seeding density express EGF-R, TGF-R1 and -2, BMP-R1A, PDGF-R1a and -B, and that a small subpopulation (between 1 and 10%) of MASCs stain with anti-SSEA4 antibodies (Kannagi R, EMBO J 2:2355-61, 1983).

Using Clontech cDNA arrays we evaluated the expressed gene profile of human MASCs cultured at seeding densities of 2×10$^3$/cm$^2$ for 22 and 26 cell doublings and found the following profiles:

A. MASCS do not express CD31, CD36, CD62E, CD62P, CD44-H, cKit, Tie, receptors for IL1, IL3, IL6, IL11, G-CSF, GM-CSF, Epo, Flt3-L, or CNTF, and low levels of HLA-class-I, CD44-E and Muc-18 mRNA.

B. MASCs express mRNA for the cytokines BMP1, BMP5, VEGF, HGF, KGF, MCP1; the cytokine receptors Flk1, EGF-R, PDGF-R1α, gp130, LIF-R, activin-R1 and -R2, TGFR-2, BMP-R1A; the adhesion receptors CD49c, CD49d, CD29; and CD10.

C. MASCs express mRNA for hTRT and TRF1; the POU-domain transcription factor oct-4 c sox-2 (required with oct-4 to maintain undifferentiated state of ES/EC, Uwanogho D, Mech Dev 49:23-36, 1995), sox-11 (neural development), sox-9 (chondrogenesis, Lefebvre V, Matrix Biol 16:529-40, 1998); homeodeomain transcription factors: Hoxa4 and -a5 (cervical and thoracic skeleton specification; organogenesis of respiratory tract, Packer A I, Dev Dyn 17:62-74, 2000), Hox-a9 (myelopoiesis, Lawrence H, Blood 89:1922, 1997), Dlx4 (specification of forebrain and peripheral structures of head, Akimenko M A, J Neurosci 14:3475-86, 1994), MSX1 (embryonic mesoderm, adult heart and muscle, chondro- and osteogenesis, Foerst-Potts L, Dev Dyn 209:70-84, 1997), PDX1 (pancreas, Offield M F, Development 122:983-95, 1996)

D. Presence of oct-4, LIF-R, and hTRT mRNA has been confirmed by RT-PCR.

E. In addition RT-PCR showed that Rex-1 mRNA (required with oct-4 to maintain ES in an undifferentiated state, Rosfjord E, Biochem Biophys Res Commun 203:1795-802, 1997) and Rox-1 mRNA (required with oct-4 for transcription of Rex-1, Ben-Shushan E, Cell Biol 18:1866-78, 1998) are expressed in MASCs.

oct-4 is a transcription factor expressed in the pregastrulation embryo, early cleavage stage embryo, cells of the inner cell mass of the blastocyst, and in embryonic carcinoma (EC) cells (Nichols J, et al Cell 95:379-91, 1998), and is down-regulated when cells are induced to differentiate. Expression of oct-4 plays an important role in determining early steps in embryogenesis and differentiation. oct-4, in combination with Rox-1, causes transcriptional activation of the Zn-finger protein Rex-1, also required for maintaining ES undiffereniated (Rosfjord E, Rizzino A. Biochem Biophys Res Commun 203:1795-802, 1997; Ben-Shushan E, et al, Mol Cell Biol 18:1866-78, 1998. In addition, sox-2, expressed in ES/EC, but also in other more differentiated cells, is needed together with oct-4 to retain the undifferentiated state of ES/EC (Uwanogho D, Rex M, Cartwright E J, Pearl G, Healy C, Scotting P J, Sharpe P T: Embryonic expression of the chicken Sox2, Sox3 and Sox11 genes suggests an interactive role in neuronal development. Mech Dev 49:23-36, 1995). Maintenance of murine ES cells and primordial germ cells requires presence of LIF whereas this requirement is not so clear for human and non-human primate ES cells.

The present inventors observed that oct-4, Rex-1 and Rox-1 are expressed in MASCs derived from human and murine marrow and from murine liver and brain. Human MASCs express the LIF-R and stain positive with SSEA-4. Initial experiments show that human MASCs are enriched by selection of LIF-R$^+$ cells even though it is not yet clear if their growth is affected by LIF. In contrast, LIF aids in the growth of murine MASCs. Finally, oct-4, LIF-R, Rex-1 and Rox-1 mRNA levels increase in human MASCs cultures beyond 30 cell doublings, which results in phenotypically more homogenous cells. In contrast, MASCs cultured at high-density lose expression of these markers. This is associated with senescence before 40 cell doublings and loss of differentiation to cells other than chondroblasts, osteoblasts and adipocytes. Thus, the presence of oct-4, combined with Rex-1, Rox-1, sox-2, and the LIF-R are markers that correlate with presence of the most primitive cells in MASCs cultures.

The present inventors have examined mice transgenic for an oct-4 promoter-eGFP gene. In these animals, eGFP expression is seen in primordial germ cells as well as in germ cells after birth. As MASCs express oct-4, the present inventors tested whether eGFP positive cells could be found in marrow, brain, and liver of these animals after birth. eGFP$^+$ cells (1% brightest population) were sorted from marrow, brain and liver from 5 day-old mice. When evaluated by fluorescence microscopy, <1% of sorted cells from brain and marrow were eGFP$^+$. oct-4 mRNA could be detected by Q-RT-PCR in the sorted population. Sorted cells have been plated under conditions that support murine MASCs (fibronectin coated wells with EGF, PDGF, LIF). Cells survived but did not expand. When transferred to murine embryonic fibroblasts, cell growth was seen. When replated again under MASC conditions, cells with morphology and phenotype of MASCs were detected.

2. Murine MASCs.

As for human cells, C57/BL6 MASCs cultured with EGF, PDGF-BB and LIF are CD44 and HLA-class-I negative, stain positive with SSEA-4, and express transcripts for oct-4, LIF-R, Rox-1 and sox-2. Likewise, MASCs from FVB/N marrow, brain and liver express oct3/4 mRNA.

Culturing Multipotent Adult Stem Cells

Multipotent adult stem cells (MASCs) isolated as described herein can be cultured using methods of the invention. Briefly, culture in low-serum or serum-free medium is preferred to maintain the cells in the undifferentiated state. Serum-free medium used to culture the cells, as described herein, is supplemented as described in Table I.

TABLE I

| | |
|---|---|
| Insulin | 10-50 µg/ml (10 µg/ml)* |
| Transferrin | 0-10 µg/ml (5.5 µg/ml) |
| Selenium | 2-10 ng/ml (5 ng/ml) |
| Bovine serum albumin (BSA) | 0.1-5 µg/ml (0.5 µg/ml) |
| Linoleic acid | 2-10 µg/ml (4.7 µg/ml) |
| Dexamethasone | 0.005-0.15 µM (.01 µM) |
| L-ascorbic acid 2-phosphate | 0.1 mM |
| Low-glucose DMEM (DMEM-LG) | 40-60% (60%) |
| MCDB-201 | 40-60% (40%) |
| Fetal calf serum | 0-2% |
| Platelet-derived growth | 5-15 ng/ml (10 ng/ml) |
| Epidermal growth factor | 5-15 ng/ml (10 ng/ml) |
| Insulin like growth factor | 5-15 ng/ml (10 ng/ml) |
| Leukemia inhibitory factor | 10-10,000 IU (1,000 IU) |

*Preferred concentrations are shown in parentheses.

Because MASCs express the LIF-R and some cells express oct-4, it was tested whether addition of LIF would improve culture. Addition of 10 ng/mL LIF to human MASCs did not affect short-term cell growth (same cell doubling time till 25 cell doublings, level of oct-4 expression). In contrast to what was seen with human cells, when fresh murine marrow mononuclear cells depleted on day 0 of CD45$^+$ cells were plated in MASCs culture, no growth was seen. When murine marrow mononuclear cells were plated, and cultured cells 14 days later depleted of CD45$^+$ cells, cells with the morphology and phenotype similar to that of human MASCs appeared. This suggests that factors secreted by hemopoietic cells may be needed to support initial growth of murine MASCs. When cultured with PDGF-BB and EFG alone, cell doubling was slow (>6 days) and cultures could not be maintained beyond 10 cell doublings. Addition of 10 ng/mL LIF significantly enhanced cell growth.

Once established in culture, cells can be frozen and stored as frozen stocks, using DMEM with 40% FCS and 10% DMSO. Other methods for preparing frozen stocks for cultured cells are also known to those of skill in the art.

Inducing MASCs to Differentiate to Form Committed Progenitors and Tissue-Specific Cell Types Using appropriate growth factors, chemokines, and cytokines, MASCs of the present invention can be induced to differentiate to form a number of cell lineages, including, for example, a variety of cells of mesodermal origin as well as cell from neuroectodermal origin (glial cells, oligodendrocytes, and neurons) as well as endodermal origin.

A. Splanchnic Mesoderm

Figure 5:
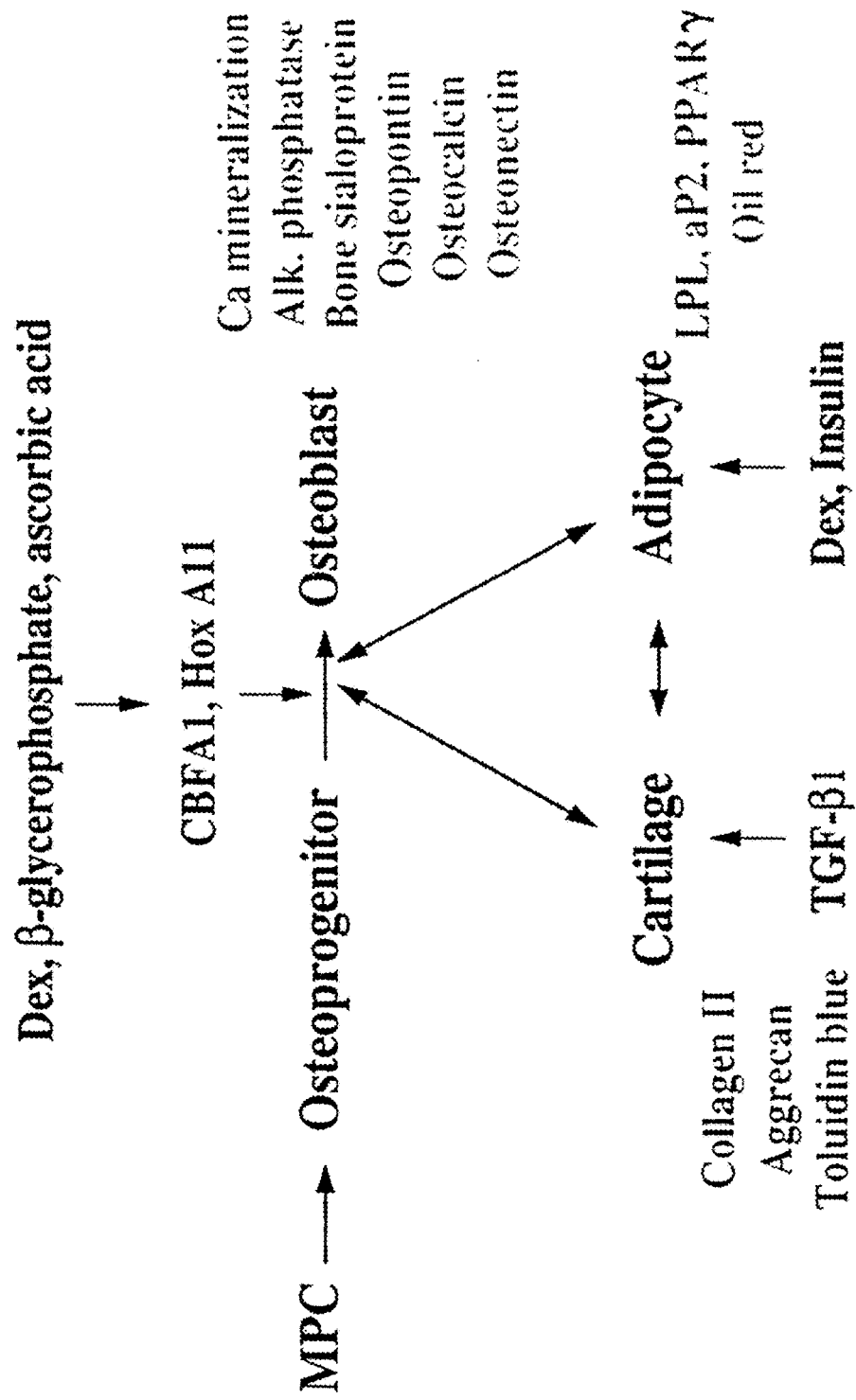
FIG. 5 illustrates the differentiation protocol used by the inventors to induce the MASCs of the present invention to differentiate to form osteoblasts, chondroblasts and adipocytes as indicated. Depicted are the cytokines needed and the appropriate tests to demonstrate induction of terminal differentiation.
Figure 6:
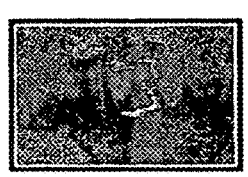
FIG. 6. illustrates results of immunohistochemistry staining for bone sialoprotein on day 15 as well as Western blot analysis for bone sialoprotein on days 7, 11 and 14 after culture after induction of MASCs with $10^{-7}$M dexamethasone, β-glycerophosphate and 10 mM ascorbic acid. In the middle panel, results of toluidin blue staining for cartilage as well as Western blot analysis for collagen type II on days 7, 11 and 14 shows differentiation to chondrocytes following culture of MASCs in micromass in serum free medium with 100 ng./mL TGF-β1. In the lower panel, oil-red staining on day 14 and Western blot analysis for PPARg shows differentiation following treatment of MASCs with 10% horse serum.
Figure 6:
Figure 6:
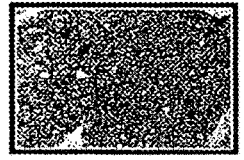
Figure 6:
Figure 6:
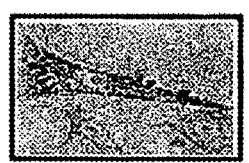
Figure 6:

1. Osteoblasts: Confluent MASCs were cultured with about $10^{-6}$-$10^{-8}$M (preferably about $10^{-7}$M) dexamethasone, β-glycerophosphate and 5-20 mM (preferably 10 mM) ascorbic acid. To demonstrate presence of osteoblasts, we used Von Kossa staining (silver reduction of CaPo4), or antibodies against bone sialoprotein, osteonectin, osteopontin and osteocalcin (immunohistochemistry/Western). After 14-21 days of culture, >80% of cells stained positive with these antibodies. (FIG. 5, 6)

2. Chondroblasts: MASCs were trypsinized, and cultured in serum-free DMEM supplemented with 50-1.00 ng/mL (preferably 100 ng/mL) TGF-β1 in micromass suspension culture. Small aggregates of cartilage formed in the bottom of the tubes that stained positive with toluidin blue. Collagen type I was detected initially throughout the micromass (day 5) but after 14 days was only detected in the outer layer of fibrillous cartilage. Collagen type II became detectable after 5 days and strongly stained the micromass by day 14. Staining for bone sialoprotein was negative or minimally positive in the outer fibrillous cartilage layer. Variable staining was found for osteonectin, osteocalcin and osteopontin. Presence of collagen type II was confirmed by Western blot and RT-PCR. In addition, RT-PCR on cells recovered after 5 days showed presence of the cartilage specific transcription factors CART1 and CD-RAP1. (FIG. 5, 6)

3. Adipocyte: To induce adipocyte differentiation, about $10^{-7}$ to about $10^{-6}$ M (preferably about $10^{-7}$ M) dexamethasone, about 50 to about 200 μg/ml (preferably about 100 μg/ml) insulin or media supplemented with approximately 20% horse serum can be used. Adipocyte differentiation can be detected by examination with light microscopy, staining with oil-red, or detection of lipoprotein lipase (LPL), adipocyte lipid-binding protein (aP2), or peroxisome proliferator-activated receptor gamma (PPAR). Methods for detection of cellular markers and products are known to those of skill in the art, and can include detection using specific ligands, such as, for example, troglitazone (TRO) and rosiglitazone (RSG), which bind to PPARγ. (FIG. 5, 6)

4. Expressed gene profile of cartilage and bone. The present inventors examined genes expressed upon differentiation to osteoblasts and chondroblasts. In particular, they examined the expressed gene profile of MASCs (n=3) and MASCs switched to osteoblast or chondroblast culture conditions for two days to determine whether a relative homogenous switch to the two specific lineages is seen, using Clonetech and Invitrogen cDNA arrays. A partial list of changes detected is shown in table 2. This is by no means a conclusive evaluation of the expressed gene profile in MASCs, osteoblasts and chondroblasts. However, the results indicate that differentiation of MASCs to bone and cartilage induces significant and divergent changes in expressed gene profile, consistent with the observation that most cells within a culture can be induced to differentiate along a given pathway.

TABLE 2 differentially expressed genes in MASCS, osteoblasts and chondroblasts

| Family | Loss | Acquisition/increase | |
| --- | --- | --- | --- |
| | Osteoblast or chondroblast | osteoblast | chondroblast |
| Transcription factors | oct-4, sox-2, Hoxa4, 5, 9; Dlx4, PDX1, hTRT, TRF1 | Hox7, hox11, sox22 | Sox-9, FREAC, hox-11, hox7, CART1, Notch3 |
| Cell cycle | Cyclins, cdk's | Cdki's | Cdki's |
| Adhesion receptors and ECM | syndecan-4; dystroglycan integrin α2, α3, β1, | syndecan-4, decorin, lumican, fibronectin, bone sialoprotein, TIMP-1, CD44, β8, β5 integrin | collagen-II, fibronectin, decorin, cartilage glycoprotein, cartilage oligomeric matrix protein, MMPs and TIMPs, N-cadherin, CD44, α1 and α6 integrin |
| Cytokine-R/cytokines | FLK1, LIF-R, RAR-α, RARγ, EGF-R, PDGF-R1a and -B, TGF-R1 and -2, BMP-R1A, BMP 1 and 4, HGF, KGF, MCP1 | PTHr-P, Leptin-R, VitD3-R, FGF-R3, FGF-R2, Estrogen-R, wnt-7a, VEGF-C, BMP2 | VitD3-R, BMP2, BMP7 |

5. Expressed gene profile of bone by subtractive hybridization: The present inventors used a subtraction approach to identify genetic differences between undifferentiated MASCs and committed progeny. Poly-A mRNA was extracted from undifferentiated MASCs and cells induced to differentiate to the osteoblast lineage for 2 days. Subtraction and amplification of the differentially expressed cDNAs was done using the PCR-Select kit from Clonetech, as per manufacturer's recommendation without modification. We started to analyze gene sequences expressed in day 2 osteoblast cultures but not in undifferentiated MASCs.

1) The present inventors sequenced 86 differentially expressed cDNA-sequences. We confirmed by Northern that the mRNAs are indeed specifically expressed in day 2 osteoblast progenitors and not MASCs. The sequences were compared (using the BLAST algorithm) to the following databases: SwissProt, GenBank protein and nucleotide collections, ESTs, murine and human EST contigs.

2) Sequences were categorized by homology: 8 are transcription factors, 20 are involved in cell metabolism; 5 in chromatin repair; 4 in the apoptosis pathway; 8 in mitochondrial function; 14 are adhesion receptors/ECM components; 19 are published EST sequences with unknown function and 8 are novel.

3) For 2 of the novel sequences, the present inventors started to perform Q-RT-PCR on MASCs induced to differentiate to bone for 12 h, 24 h, 2 d, 4 d, 7 d and 14 d from 3 individual donors. Genes are expressed during the initial 2 and 4 days of differentiation respectively, and down regulated afterwards.

4) The present inventors have also started to analyze genes present in undifferentiated MASCs but not day 2 osteoblasts. Thirty differentially expressed genes have been sequenced and 5 of them are EST sequences or unknown sequences.

B. Muscle

Differentiation to any muscle phenotype required that MASCs be allowed to become confluent prior to induction of differentiation.

1. Skeletal muscle: To induce skeletal muscle cell differentiation, confluent MASCs cells were treated with about 1 to about 3 µM (preferably about 3 µM) 5-azacytidine in MASC expansion medium for 24 hours. Cultures were then maintained in MASCs medium. Differentiation was evaluated by Western blot and immunohistochemistry. Skeletal muscle differentiation in vitro can be demonstrated by detecting sequential activation of Myf-5, Myo-D, Myf-6, myogenin, desmin, skeletal actin and skeletal myosin, either by immunohistochemistry or Western blot analysis using standard techniques known to those of skill in the art and commercially available antibodies. Five days after induction with either 5-azacytidine the Myf5, Myo-D and Myf6 transcription factors could be detected in approximately 50% of cells. After 14-18 days, Myo-D was expressed at significantly lower levels, whereas Myf5 and Myf6 persisted. Desmin and skeletal actin were detected as early as four days after induction, and skeletal myosin at 14 days. By immunohistochemistry, 70-80% of cells expressed mature muscle proteins after 14 days. Treatment with 5-azacitidine resulted in expression of Gata4 and Gata6 during the first week of culture. In addition, low levels of troponin-T could be detected from day two onwards. Smooth muscle actin was detected at two days after induction and persisted for 14 days. When 20% horse serum was added, a fusion of myoblasts into myotubes that were multinucleated was seen. (FIG. 7) Using double fluorescent labeling we could show that transduced myoblasts could be caused to fuse with differentially lateral myocytes (FIG. 8).

Figure 7:
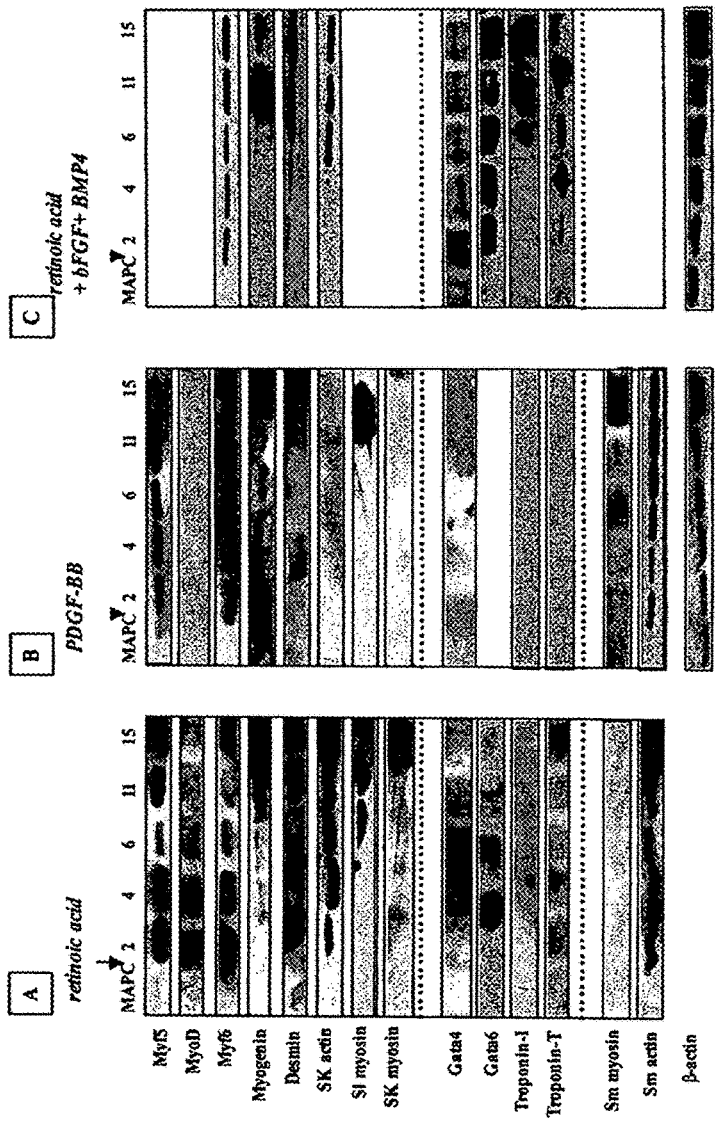
FIG. 7. shows Western blot analysis for muscle proteins. Panel A, shows results of culture of confluent MASCs with 3 μM 5-azacytidine for 24 h. Cultures were then maintained in MASC expansion medium (DMEM, 2% FCS, EGF, PDGF-BB, transferrin, selenium, bovine serum albumin, dexamethasone, linoleic acid, insulin and ascorbic acid). Differentiation was evaluated by Western blot. 5 days after induction with either 5-azacytidine, the Myf5, Myo-D and Myf6 transcription factors could be detected in approximately 50% of cells. After 14-18 days, Myo-D was expressed at significantly lower levels, whereas Myf5 and Myf6 persisted. We detected desmin and skeletal actin as early as 4 days after induction, and skeletal myosin at 14 days. By immunohistochemistry, 70-80% of cells expressed mature muscle proteins after 14 days (not shown). Treatment with either 5-azacytidine or retinoic acid resulted in expression of Gata4 and Gata6 during the first week of culture. In addition, low levels of troponin-T could be detected from day 2 on, which may suggest that fetal muscle generated as cardiac troponin-T is found in embryonal skeletal muscle. Smooth muscle actin was detected at 2 days after induction and persisted till 14 days. In panel B, we added 100 ng/mL PDGF as the sole cytokine to confluent MASCS maintained in serum-free medium for 14 days. Presence of smooth muscle markers was evaluated by Western blot. Smooth muscle actin was detected from day 2 on and smooth muscle myosin after 6 days. Approximately 70% of cells stained positive with anti-smooth muscle actin and myosin antibodies on day 15 by immunohistochemistry. We found presence of myogenin from day 4 on and desmin after 6 days. We also detected Myf5 and Myf6 proteins after 2-4 days, which persisted till day 15. No Myo-D was detected.

2. Smooth muscle: Smooth muscle cells can also be induced by culturing MASCs in serum-free medium, without growth factors, supplemented with high concentrations (about 50 to about 200 ng/ml, preferably about 100 ng/ml) of platelet-derived growth factor (PDGF). Cells should preferably be confluent at initiation of differentiation. Terminally differentiated smooth muscle cells can be identified by detecting expression of desmin, smooth muscle specific actin, and smooth muscle specific myosin by standard methods known to those of skill in the art. Smooth muscle actin was detected from day two onwards and smooth muscle myosin after 14 days. Approximately 70% of cells stained positive with anti-smooth muscle actin and myosin antibodies. A presence of myogenin was seen from day four onwards and desmin after 6 days. Myf5 and Myf6 proteins were also detected after 2-4 days, which persisted till day 15. No Myo-D was detected. (FIG. 7)

3. Cardiac muscle: Cardiac muscle differentiation can be accomplished by adding about 5 to about 200 ng/ml (preferably about 100 ng/ml) basic fibroblast growth factor (bFGF) to the standard serum-free culture media without growth factors, as previously described. Confluent MASCs were exposed to µM (preferably about 3 µM) 5-azacytidine and to $10^{-5}$-$10^{-7}$ M (preferably $10^{-6}$ M) retinoic acid, and then cultured in MASC expansion medium afterwards. Alternatively, MASCs were cultured with either of these inducers alone or a combination of both and then cultured in serum-free medium with 50-200 ng/mL (preferably 100 ng/mL FGF2 or a combination of 5-20 ng/mL (preferably 10 ng/mL) BMP-4 and 100 ng/mL FGF2. We found expression of proteins consistent with cardiomyocytes. Gata4 and Gata6 were expressed as early as day 2 and persisted till day 15. Cardiac troponin-T was expressed after day 4 and cardiac troponin-I from day 6 on, while we could detect ANP after day 11. These cardiac proteins were detected in >70% of cells by immuno-histochemistry on day 15. We found the transcription factor Myf6 from day 2 on. Expression of desmin started on day 6 and myogenin on day 2. We also found skeletal actin. When the cultures were maintained for >3 weeks, cells formed syncithia. We also saw infrequent spontaneous contractions occurring in the cultures, which were propagated over several mm distance. (FIG. 7)

C. Endothelial Cells MASCs express Flk1 but not CD34, PECAM, E-and P-selectin, CD36, Tie/Tek or Flt1. When MASCs were cultured serum-free MASCs medium with 20 ng/mL VEGF we saw the appearance of CD34 on the cell surface and cells expressed vWF by day 14 (immunofluorescence) (FIG. 9, 10). In addition, cells expressed Tie, Tek, Flk1 and Flt1, PECAM, P-selectin and E-selectin, and CD36. Results from the histochemical staining were confirmed by Western blot. When VEGF induced cells were cultured on matrigel or collagen type IV, vascular tube formation was seen. (FIG. 9, 10)

D. Hemopoietic Cells As MASCs differentiate into $CD34^+$ endothelial cells and recent studies show that $CD34^-$ $Flk1^+$ cells can be induced to differentiate into endothelial cells as well as hemopoietic cells, we tested whether MASCs could be induced to differentiate in hemopoietic precursors. MASCs were replated on collagen type IV in PDGF-BB- and EGF-containing MASCs medium with 5% FCS and 100 ng/mL SCF that was conditioned by the AFT024 feeder, a fetal liver derived mesenchymal line that supports murine and human repopulating stem cells ex vivo. Cells recovered from these cultures expressed cKit, cMyb, Gata2 and G-CSF-R but not CD34 (RT-PCR). Because hemopoiesis is induced by factors that are released by embryonal visceral endoderm, we co-cultured human MASCs with $\beta Gal^+$ murine EBs in the presence of human SCF, Flt3-L, Tpo and Epo. In 2 separate studies, we detected a small population of $\beta Gal^-$ cells that expressed human CD45.

E. Stromal cells: The inventors induced "stromal" differentiation by incubating MASCs with IL-1α, FCS, and horse serum. To demonstrate that these cells can support hemopoiesis, feeders were irradiated at 2,000 cGy and $CD34^+$ cord blood cells plated in contact with the feeder. After 1, 2 and 5 weeks, progeny was replated in methylcellulose assay to determine the number of colony forming cells (CFC). A 3-5-fold expansion of CFC was seen after 2 weeks and maintenance of CFC at 5 weeks, which was similar to cultures of $CD34^+$ cells in contact with the murine fetal liver derived feeder, AFT024.

F. Neuronal Cells Surprisingly, MASCs induced with VEGF, the hemopoietic cytokines SCF, Flt3-L, Tpo and Epo in MASCs medium containing EGF conditioned by the hematopoietic supportive feeder AFT024 differentiated into glial-fibrilar-acidic-protein (GFAP) positive astrocytes, galactocerebroside (GalC) positive oligodendrocytes and neurofilament positive neurons (FIG. 11) The inventors hypothesized that production of FGF2 by the AFT024 feeders and addition of EGF to the cultures might induce differentiation to neuronal cells in vitro.

They then examined the effect FGF2, known to play a key role in neural development and ex vivo culture of neural precursors, on MASCs derived neural development. When <50% confluent cultures of human marrow derived MASCs (n=7) that had been cultured with EGF and PDGF-BB were switched to medium containing 50-500 ng/mL (preferably 100 ng/mL) FGF2, differentiation to cells expressing of astrocytes, oligodendrocytes and neurons was seen after 2-4 weeks (FIG. 11) After two weeks in culture, 26±4% of cells were GFAP positive, 28±3% GalC positive and 46±5% neurofilament-200 positive. When reexamined after three weeks, fewer cells were GFAP or GalC positive, but 20±2% cells stained positive for β-tubulin-III, 22±3% for neurofilament-68, 50±3% for neurofilament-160, 20±2% for neurofilament-200, 82±5% for neuron-specific-enolase (NSE) and 80±2% for microtubule-associated-protein-2 (MAP2) (FIG. 11) GABA, parvalbumin, tyrosine hydroxylase, DOPA-decarboxylase, and tryptophan hydroxylase were not detected. The number of neurites per neuron increased from 3±1, to 5±1 and 7±2 from 2, 3 to 4 weeks after differentiation. Differentiation to cells with characteristics of astrocytes, oligodendrocytes and neurons was confirmed by demonstrating presence of GFAP, myelin basic protein (MBP) and neurofilament-200 by Western blot and RT-PCR analysis in FGF2 treated but not MASCs).

FGF-9, first isolated from a glioblastoma cell line, induces proliferation of glial cells in culture. FGF-9 is found in vivo in neurons of the cerebral cortex, hippocampus, substantia nigra, motor nuclei of the brainstem and Purkinje cell layer. When cultured for 3 weeks with 5-50 ng/mL (preferably 10 ng/mL) FGF-9 and EGF MASCs generated astrocytes, oligodendrocytes and GABAergic and dopaminergic. During CNS development, FGF-8, expressed at the mid/hindbrain boundary and by the rostral forebrain, in combination with Sonic hedgehog, induces differentiation of dopaminergic neurons in midbrain and forebrain. It was found that when MASCs were cultured with 5-50 ng/mL (preferably 10 ng/mL) FGF-8 and EGF for 3 weeks both dopaminergic and GABAergic neurons were produced. FGF-10 is found in the brain in very low amounts and its expression is restricted to the hippocampus, thalamus, midbrain and brainstem where it is preferentially expressed in neurons but not in glial cells. Culture of MASCs in 5-50 ng/mL (preferably 10 ng/mL) FGF-10 and EGF for three weeks generated astrocytes and oligodendrocytes, but not neurons. FGF-4 is expressed by the notochord and is required for the regionalisation of the midbrain. When treated with 5-50 ng/mL (preferably 10 ng/mL) FGF-4 and EGF for 3 weeks MASCs differentiated into astrocytes and oligodendrocytes but not neurons.

Other growth factors that are specifically expressed in the brain and that affect neural development in-vivo and in-vitro include brain derived neurotrophic factor (BDNF), glial derived neurotrophic factor (GDNF) and ciliary neurotrophic factor (CNTF). BDNF is a member of the nerve growth factor family that promotes in vitro differentiation of NSC, human subependymal cells, and neuronal precursors to neurons and promotes neurite outgrowth of hippocamal stem cells in vivo. Consistent with the known function of BDNF to support survival of dopaminergic neurons of the substantia nigra, when MASCs were treated with 5-50 ng/mL (preferably 10 ng/mL) BDNF and EGF exclusive differentiation into tyrosine hydroxylase positive neurons was seen. GDNF is a member of the TGF- superfamily. In early neurogenesis, GDNF is expressed in the anterior neuroectoderm suggesting that it may play a key role in neuronal development. GDNF promotes survival of motor neurons in peripheral nerve and muscle and has neurotrophic and differentiation abilities. It was found that 5-50 ng/mL (preferably 10 ng/mL) GDNF induced MASCs to differentiate into GABAergic and dopaminergic neurons. CNTF, first isolated from ciliary ganglion, is a member of the gp130 family of cytokines. CNTF promotes neuronal survival early in development. In embryonic rat hippocampal cultures CNTF increased the numbers of GABAergic and cholinergic neurons. In addition, it prevented cell death of GABAergic neurons and promoted GABA uptake. 5-50 ng/mL (preferably 10 ng/mL) CNTF exerted the same GABAergic induction on MASCs as they differentiated exclusively into GABAergic neurons after three weeks of exposure to CNTF.

The fate of MASCs transplanted into rat brain was also examined. 50,000 eGFP$^+$ MASCs were transplanted stereotactically around a parietal infarct induced in Wistar rats, maintained on cyclosporin. Limb-placement was tested six weeks after transplant of saline, MASCs conditioned medium, or MASCs. Functional improvement to levels equivalent to that of sham animals was only seen in rats transplanted with MASCs (FIG. 15).

After two and six weeks, animals were sacrificed to determine neural phenotype. Because of autofluorescence of the brain following transplantation with eGFP$^+$ cells, immunohistochemical analysis of the graft was performed. The majority of eGFP$^+$ cells were detected in the grafted area itself at two weeks (FIG. 16). After five weeks, eGFP$^+$ cells migrated outside the graft. At two weeks, cells staining with an anti-eGFP antibody remained spherical in nature and ranged from 10-30 μm in diameter. After six weeks, cells with an anti-eGFP antibody were significantly smaller and dendrites could be seen in the grafted area, extending out to the normal brain tissue. Presence of human cells was confirmed by staining with a human specific nuclear antibody, NuMa. This antibody can be used to identify human cells in the graft allowing double and triple staining with immunofluorescent antibodies.

Using human specific anti-nestin antibodies, the present inventors detected small clusters of nestin-positive cells in the same location of the graft as the NuMa-positive cells and GFP$^+$ cells, suggestive of neuroectodermal differentiation. In addition, they found positive staining for -tubulin III and Neurofilament-68 and -160, Oligo Marker and GFAP, suggesting differentiation to neuronal and glial cells (not shown).

G. Epithelial Cells The inventors treated confluent MASCs (N=4) with 10 ng/mL hepatocyte growth factor (HGF), alone or in combination with keratinocyte growth factor (KGF). After 14 days, large epithelioid cells could be seen that expressed the HGF receptor, cytokeratin 8, 18 and 19. Presence of cytokeratin-19 suggests possible differentiation to biliary epithelium. Changing the matrix from fibronectin to a collagen gel or matrigel improved generation of cytokeratin-18 expressing cells with morphology of epithelial cells. (FIG. 17)

Single Cell Origin of Differentiated Lineages.

To address if MASCs are clonal, the inventors have sorted by FACS 1 and 10 MFG-eGFP transduced eGFP$^+$ cells per well and cultured cells to generate $10^8$ cells. Transduction was done as follows: MASCs replated 24 h earlier were exposed for 6 h on 2 sequential days to MFG-eGFP or MSCV-eGFP packaged in the PG13 cell line and 10 μg/mL protamine. Between 40-70% of MASCS were transduced. Expression of eGFP persisted for at least 3 months ex vivo, and persisted in a large fraction of cells following differentiation. When a single cell was sorted, no growth was seen in >1,000 wells. However, when 10 cells were deposited/well, cell growth was seen in 3% of wells, extensive expansion to >$10^7$ cells was seen in only 0.3% of wells. These cells were then induced to differentiate into all mesodermal cell types (osteoblasts, chondroblasts, adipocytes, skeletal and smooth muscle cells, and endothelium). Differentiation was again shown by immunohistochemistry and Western blot. Cells were also subjected to inverse PCR to demonstrate that the sequences in the human DNA flanking the viral insert were similar. The inventors found that the retroviral gene was inserted in the same site in the human genome in MASCs and differentiate progeny in 3 independent clones.

MASC Engraftment

The inventors initiated studies to examine if MASCs engraft and persist in vivo.

1. The inventors injected eGFP+ MASCs intramuscularly into NOD-SCID mice. Animals were sacrificed 4 weeks later and muscle examined to determine if, as has been described for human ES cells, teratomas develop. In 5/5 animals, no teratomas were seen. eGFP positive cells were detected.
2. The inventors infused eGFP+ MASCs IV intrauterine in fetal SCID mice. Animals were evaluated immediately after birth. PCR analysis demonstrated presence of eGFP+ cells in heart, lung, liver, spleen and marrow.
3. The inventors transplanted MASCs stereotaxically in the intact brain or infarcted brain of rats, they acquire a phenotype compatible with neural cells, and persist for at least 6 weeks.

Applications of MASCs 1. osteoblasts: MASCs of the present invention that have been induced to differentiate to form bone cells can be used as cell therapy or for tissue regeneration in osteoporosis, Paget's disease, bone fracture, osteomyelitis, osteonecrosis, achondroplasia, osteogenesis imperfecta, hereditary multiple exostosis, multiple epiphyseal dysplasia, Marfan's syndrome, mucopolysaccharidosis, neurofibromatosis or scoliosis, reconstructive surgery for localized malformations, spina bifida, hemivertebrae or fused vertebrae, limb anomalies, reconstruction of tumor-damaged tissue, and reconstruction after infection, such as middle ear infection.
2. chondrocytes: MASCs of the present invention can be induced to differentiate to form cartilage cells for cell therapy or tissue regeneration in age-related diseases or injuries, in sports-related injuries, or in specific diseases such as rheumatoid arthritis, psoriasis arthritis, Reiter's arthritis, ulcerative colitis, Crohns' disease, ankylosing spondylitis, osteoarthritis, reconstructive surgery of the outer ear, reconstructive surgery of the nose, and reconstructive surgery of the cricoid cartilage.
3. adipocytes: Adipocytes derived from the MASCs can be used in resculpting during reconstructive or cosmetic surgery, as well as for the treatment of Type II diabetes. In reconstructive surgery, adipocytes differentiated as described by the method of the present invention can be used for breast reconstruction after mastectomy, for example, or for reshaping tissue lost as a result of other surgery, such as tumor removal from the face or hand. In cosmetic surgery, adipocytes produced from the cells of the present invention by the method of the present invention can be used in a variety of techniques, such as breast augmentation, or for reduction of wrinkles in aging skin. Adipocytes thus derived can also provide an effective in vitro model system for the study of fat regulation.
4. fibroblasts: Fibroblasts derived from the MASCs can be used for cell therapy or tissue repair to promote wound healing or to provide connective tissue support, such as scaffolding for cosmetic surgery.
5. Skeletal muscle: MASCs can be induced to differentiate to form skeletal muscle cells for cell therapy or tissue repair in the treatment of Duchene muscular dystrophy, Becker muscular dystrophy, myotonic dystrophy, skeletal myopathy, and reconstructive surgery to repair skeletal muscle damage.
6. Smooth muscle: MASCs can be induced to differentiate to form smooth muscle cells for cell therapy or tissue repair in the treatment of developmental abnormalities of the gastrointestinal system, such as oesophageal atresia, intestinal atresia, and intussusception, as well as for replacement of tissues after surgery for bowel infarction or colocolostomy.

Smooth muscle cells formed from the MASCs of the present invention can also be used for bladder or uterine reconstruction, for neovascularization, for repair of vessels damaged by, for example, atherosclerosis or aneurysm. Smooth muscle precursor cells (mesangial cells) can be used as an in vitro model for glomerular diseases or for cell therapy or tissue regeneration in diabetic neuropathy. Smooth muscle precursors can also be used to repair macula densa of the distal convoluted tubule or juxtaglomerular tissues, which play a role in blood pressure regulation.

7. cardiomyocytes: Cardiomyocytes derived from the MASCs can be useful for cell therapy or tissue repair for treating heart tissue damaged following myocardial infarction, in conjunction with congestive heart failure, during valve replacement, by congenital heart anomalies, or resulting from cardiomyopathies or endocarditis. Cells can be delivered locally, especially by injection, for increased effectiveness. Microglial cells differentiated from MASCs can be used to treat spinal cord injuries and neurodegenerative disorders, such as Huntingtons disease, Parkinsons disease, Multiple Sclerosis, and Alzheimers disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, as well as for regeneration after spinal cord injury.
8. stromal cells: Stromal cells derived from the MASCs of the present invention can be used as transplant cells for post-chemotherapy bone marrow replacement, as well as for bone marrow transplantation. In breast cancer, for example, a bone marrow aspirate is obtained from a patient prior to an aggressive chemotherapy regimen. Such chemotherapy is damaging to tissues, particularly to bone marrow. MASCs isolated from the patient's bone marrow can be expanded in culture to provide enough autologous cells for re-population of the bone marrow cells. Because these cells can differentiate to multiple tissues types, cells introduced either locally or systemically provide an added advantage by migrating to other damaged tissues, where cellular factors in the tissue environment induce the cells to differentiate and multiply.
9. endothelial cells: MASCs can be differentiated by the methods described to produce endothelial cells, which can be used in the treatment of Factor VIII deficiency, as well as to produce angiogenesis for neovascularization. Endothelial cells can also provide an in vitro model for tumor suppression using angiogenic inhibitors, as well as an in vitro model for vasculitis, hypersensitivity and coagulation disorders. Using these cultured endothelial cells and rapid screening methods known to those of skill in the art, thousands of potentially useful therapeutic compounds can be screened in a more timely and cost-effective manner.
10. hematopoietic cells: MASCs can differentiate into hematopoietic cells. Cells of the present invention can therefore be used to repopulate the bone marrow after high dose chemotherapy. Prior to chemotherapy, a bone marrow aspirate is obtained from the patient. Stem cells are isolated by the method of the present invention, and are grown in culture and induced to differentiate. A mixture of differentiated and undifferentiated cells is then reintroduced into the patient's bone marrow space. Clinical trials are currently underway using hematopoietic stem cells for this purpose. The stem cells of the present invention, however, provide the additional benefit of further differentiation to form cells that can replace those damaged by chemotherapy in other tissues as well as in bone marrow. Hematopoietic cells derived from the MASCs can be further differentiated to form blood cells to be stored in blood banks, alleviating the problem of a limited supply of blood for transfusions.

11. Neuroectodermal cells: Microglial cells differentiated from MASCs can be used to treat spinal cord injuries and neurodegenerative disorders, such as Huntingtons disease, Parkinsons disease, Multiple Sclerosis, and Alzheimers disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, as well as for regeneration after spinal cord injury. MASCs induced to form oligodendrocytes and astrocytes, for example, can be used for transplant into demyelinated tissues, especially spinal cord, where they function to myelinate the surrounding nervous tissues. This technique has been demonstrated effective in mice, using embryonic stem cells as the source of oligodendrocyte and astrocyte precursors (Brustle, O., et al., *Science* (1999) 285: 754-756). The MASCs of the present invention exhibit the broad range of differentiation characteristic of embryonic cells, but provide the added advantage of contributing autologous cells for transplant.

The cells of the present invention can be used in cell replacement therapy and/or gene therapy to treat congenital neurodegenerative disorders or storage disorders such as, for instance, mucopolysaccharidosis, leukodystrophies (globoid-cell leukodystrophy, Canavan disease), fucosidosis, GM2 gangliosidosis, Niemann-Pick, Sanfilippo syndrome, Wolman disease, and Tay Sacks. They can also be used for traumatic disorders such as stroke, CNS bleeding, and CNS trauma; for peripheral nervous system disorders such as spinal cord injury or syringomyelia; for retinal disorders such as retinal detachment, macular degeneration and other degenerative retinal disorders, and diabetic retinopathy.

12. Ectodermal epithelial cells: Moreover, the epithelial cells of the present invention can also be used in cell replacement therapy and/or gene therapy to treat or alleviate symptoms of skin disorders such as alopecia, skin defects such as burn wounds, and albinism.

13. Endodermal epithelial cells: Epithelial cells derived from the MASC of the present invention can be used in cell replacement therapy and/or gene therapy to treat or alleviate symptoms of several organ diseases. The cells could be used to treat or alleviate congenital liver disorders, for example, storage disorders such as mucopolysaccharidosis, leukodystrophies, GM2 gangliosidosis; increased bilirubin disorders, for instance Crigler-Najjar syndrome; ammonia disorders such as inborn errors of the urea-cycle, for instance Ornithine decarboxylase deficiency, citrullinemia, and argininosuccinic aciduria; inborn errors of amino acids and organic acids such as phenylketoinuria, hereditary tyrosinemia, and Alpha1-antitrypsin deficiency; and coagulation disorders such as factor VIII and IX deficiency. The cells can also be used to treat acquired liver disorders due to viral infections. The cells of the present invention can also be used in ex vivo applications such as to generate an artificial liver (akin to kidney dialysis), to produce coagulation factors and to produce proteins or enzymes generated by liver epithelium.

These epithelial cells of the present invention can also be used in cell replacement therapy and/or gene therapy to treat or alleviate symptoms of biliary disorders such as biliary cirthosis and biliary atresia.

The epithelial cells of the present invention can also be used in cell replacement therapy and/or gene therapy to treat or alleviate symptoms of pancreas disorders such as pancreatic atresia, pancreas inflammation, and Alpha1-antitrypsin deficiency. Further, as pancreas epithelium can be made from the cells of the present invention, and as neural cells can be made, beta-cells can be generated. These cells can be used for the therapy of diabetes (subcutaneous implantation or intra-pancreas or intra-liver implantation. Further, the epithelial cells of the present invention can also be used in cell replacement therapy and/or gene therapy to treat or alleviate symptoms of gut epithelium disorders such as gut atresia, inflammatory bowel disorders, bowel infarcts, and bowel resection.

14. Modification of MASC to ensure absence of senescence under less than optimal culture conditions: Although MASC have long telomeres (12 kb) and the telomere length is not different in cells from donors of different ages. Upon ex vivo culture of the MASC, telomeres do not shorten for an extended period of time, i.e., for over 4 months in ex vivo culture (or >35 cell doublings). This may persist longer. Telomerase is present in MASC derived from people of all ages. When MASC cells are cultured under confluent conditions, senescence occurs and telomers begin to shorten. As extensive expansion in relative high dense cultures may be preferable for production, commercial or other purposes, MASC can be transduced/transfected with a telomerase-containing construct, which will prevent senescence of cells. As these cells could then be used for in vivo transplantation, it would be preferable that telomerase be removed from the cell prior to transplantation. This can be accomplished by engineering the telomerase construct such that it is located between two LoxP sites. The Cre recombinase will be able to then excize telomerase. Cre can be transfected/transduced into the target cell using a second vector/plasmid or as part of the telomerase-containing construct. Cre can be introduced in a constitutively active form, or as an inducible enzyme, for instance by flanking the protein with one or more mutated ligand binding domains of the human estrogen receptor (ER) that can be induced by 4-hydroxy-tamoxifen (OHT), but not natural ER ligands, or by using a tetracyclin or rapamacine inducible, or other drug inducible system.

15. Approaches for transplantation to prevent immune rejection:

a. universal donor cells: MASC can be manipulated to serve as universal donor cells for cell and gene therapy to remedy genetic or other diseases and to replace enzymes. Although undifferentiated MASC express no HLA-type I, HLA-type II antigens or beta-2 microglobulin, some differentiated progeny express at least type I HLA-antigens. MACS can be modified to serve as universal donor cells by eliminating HLA-type I and HLA-type II antigens, and potentially introducing the HLA-antigens from the prospective recipient to avoid that the cells become easy targets for NK-mediated killing, or become susceptible to unlimited viral replication and/or malignant transformation. Elimination of HLA-antigens can be accomplished by homologous recombination or via introduction of point-mutations in the promoter region or by introduction of a pointmutation in the initial exon of the antigen to introduce a stop-codon, such as with chimeroplasts. Transfer of the host HLA-antigen can be achieved by retroviral, lentiviral, adeno associated virus or other viral transduction or by transfection of the target cells with the HLA-antigen cDNA's. MASC can be used to establish and set amount or a given range or level of a protein in the body or blood.

b. Intrauterine transplant to circumvent immune recognition: MASC can be used in intrauterine transplantation setting to correct genetic abnormalities, or to introduce cells that will be tolerated by the host prior to immune system development. This can be a way to make human cells in large quantities such as blood, in animals or it could be used as a way to correct human embryo genetic defects by transplanting cells that make the correct protein or enzyme.

16. Gene therapy: Until now, human cells used for gene therapy have been essentially limited to bone marrow and skin cells, because other types of cells could not be extracted from the body, grown in culture, genetically altered, then successfully reimplanted into the patient from whom the tissue was taken. (Anderson, W. F., *Nature* (1998) 392: 30; Anderson, W. F., *Scientific American* (1995) 273: 1-5; Anderson, W. F. *Science* (1992) 256: 808-813) MASCs of the present invention can be extracted and isolated from the body, grown in culture in the undifferentiated state or induced to differentiate in culture, and genetically altered using a variety of techniques, especially viral transduction. Uptake and expression of genetic material is demonstrable, and expression of foreign DNA is stable throughout development. Retroviral and other vectors for inserting foreign DNA into stem cells are known to those of skill in the art. (Mochizuki, H., et al., *J. Virol* (1998) 72(11): 8873-8883; Robbins, P., et al., *J. Virol.* (1997) 71(12): 9466-9474; Bierhuizen, M., et al., *Blood* (1997) 90(9): 3304-3315; Douglas, J., et al., *Hum. Gene Ther.* (1999) 10(6): 935-945; Zhang, G., et al., *Biochem. Biophys. Res. Commun.* (1996) 227(3): 707-711). Once transduced using a retroviral vector, enhanced green fluorescent protein (eGFP) expression persists in terminally differentiated muscle cells, endothelium, and c-Kit positive cells derived from the isolated MASCs, demonstrating that expression of retroviral vectors introduced into MASC persists throughout differentiation. Terminal differentiation was induced from cultures initiated with 10 eGFP$^+$ cells previously transduced by retroviral vector and sorted a few weeks into the initial MASC culture period.

Hematopoietic stem cells, although limited in differentiation potential, demonstrate utility for gene therapy (see Kohn, D. B., *Curr. Opin. Pediatr.* (1995) 7: 56-63). The cells of the present invention provide a wider range of differentiated cell types which can retain transduced or transfected DNA when terminally differentiated, as demonstrated by the fact that terminally differentiated muscle cells, endothelium, and c-Kit positive cells retained enhanced green fluorescent protein expression although the retroviral vector had been introduced into the undifferentiated stem cell.

MASCs of the present invention provide other advantages over hematopoietic stem cells for gene therapy, as well. Stem cells of the present invention are relatively easy to isolate from bone marrow aspirates obtained under local anesthesia, easy to expand in culture, and easy to transfect with exogenous genes. Adequate numbers of hematopoietic stem cells for the same purpose must be isolated from at least one liter of marrow and the cells are difficult to expand in culture (see Prockop, D. J., *Science* (1997) 276: 71-74).

Candidate genes for gene therapy include, for example, genes encoding Apolipoprotein E (which has been correlated with risk for Alzheimer's disease and cardiovascular disease), MTHFR (variants of which have been associated with increased homocysteine levels and risk of stroke), Factor V (which has been correlated with risk of thrombosis), ACE (variants of which have been correlated with risk of heart disease), CKR-5 (which has been associated with resistance to HIV), HPRT (hypoxanthine-guanine phosphoribosyl transferase, the absence of which results in Lesch-Nyhan disease), PNP (purine nucleoside phosphorylase, the absence of which results in severe immunodeficiency disease), ADA (adenosine deaminase, the absence of which results in severe combined immunodeficiency disease), p21 (which has been proposed as a candidate gene for treatment for ataxia telangiectasia), p47 (the absence of which is correlated with lack of oxidase activity in neutrophils of patients with chronic granulomatous disease, GenBank accession number M55067 and M38755), Rb (the retinoblastoma susceptibility gene associated with tumor formation, GenBank accession number M15400), KVLQT1 (a potassium channel protein, with aberrant forms associated with cardiac arrhythmias, GenBank accession number U40990), the dystrophin gene (associated with Duchenne muscular dystrophy, GenBank accession numbers M18533, M17154, and M18026), CFTR (the transmembrane conductance regulator associated with cystic fibrosis, GenBank accession number M28668), phosphatidylinositol 3-kinase (associated with ataxia telangiectasia, GenBank accession number U26455), and VHL (loss or mutation of the protein is associated with Von-Hippel Lindau disease: Latif, F., et al., Science (1993) 260: 1317-1320). Other diseases which can be treated effectively using these genetically-altered cells include, Factor IX deficiency, adenosine deaminase deficiency (associated with severe combined immunodeficiency disease, or SCIDS), and diabetes, and deficiencies in glucocerebrosidase, α-iduronidase.

These novel genes can be driven by an inducible promoter so that levels of enzyme can be regulated. These inducible promoter systems may include a mutated ligand binding domain of the human estrogen receptor (ER) attached to the protein to be produced. This would require that the individual ingests tamoxifen to allow expression of the protein. Alternatives are tetracyclin on or off systems, RU486, and a rapamycin inducible system. An additional method to obtain relative selective expression is to use tissue specific promoters. For instance in the brain, one can introduce a transgene driven by the neuron-specific enolase promoter (Ad-NSE) or the glial fibrillary acidic protein promoter (GFAP) promoter, which will allow almost exclusive expression in brain tissue. Likewise, endothelial expression only may be obtained by using the Tec promoter or the VE-cadherin promoter.

Genetically altered MASCs can be introduced locally or infused systemically. Human stem cells with more limited differentiation potential, when transfected with a gene for factor IX, secrete the protein for at least 8 weeks after systemic infusion into SCID mice. (Keating, A., et al., *Blood* (1996) 88: 3921.) MASCs of the present invention, having a broader differentiation potential than any non-embryonic stem cell described thus far, provide an added advantage for systemic or local administration, because they can migrate to a variety of tissues, where cytokines, growth factors, and other factors induce differentiation of the cell. The differentiated cell, now a part of the surrounding tissue, retains its ability to produce the protein product of the introduced gene.

In Parkinson's disease, for example, clinical trials have shown that mesencephalic dopamine neurons obtained from human embryo cadavers can survive and function in the brains of patients with Parkinson's disease. PET scans have indicated that [$^{18}$F]fluorodopa uptake in the area around the cell graft is increased after transplantation, and remains so for at least six years in some patients. (See Dunnett, S. and A. Bjorklund, Nature (1999) 399 (Suppl.) A32-A-39; Lindvall, O., Nature Biotech. (1999) 17: 635-636; Wagner, J., et al., Nature Biotech. (1999) 17: 653-659.) Unlike the embryonic cells, isolated MASCs as described by the present invention provide a ready supply of cells for transplant, yet maintain the differentiation potential that makes embryonic cell transplant therapy an attractive alternative for disease treatment.

For AIDS therapy, MASCs of the present invention can be genetically engineered to produce Rev M10, a transdominant negative mutant of Rev that blocks the function of a wild-type Rev produced in HIV-infected cells. (Bevec, D. et al., Proc. Natl. Acad. Sci. USA (1992) 89: 9870-9874; Ranga, U., et al., Proc. Natl. Acad. Sci. USA (1998) 95(3): 1201-1206.) Once induced to differentiate into hematopoietic lineage cells and introduced into the patient, MASCs repopulate the HIV-infected patient's depleted T cell supply. Since the genetically altered cells possess the mutant Rev M10, they will be resistant to the lethal effects of infection by most strains of HIV.

Genetically altered MASCs can also be encapsulated in an inert carrier to allow the cells to be protected from the host immune system while producing the secreted protein. Techniques for microencapsulation of cells are known to those of skill in the art (see, for example, Chang, P., et al., Trends in Biotech. (1999) 17(2): 78-83). Materials for microencapsulation of cells include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. U.S. Pat. No. 5,639,275 (Baetge, E., et al.), for example, describes improved devices and methods for long-term, stable expression of a biologically active molecule using a biocompatible capsule containing genetically engineered cells. Such biocompatible immunoisolatory capsules, in combination with the MASCs of the present invention, provide a method for treating a number of physiologic disorders, including, for example, diabetes and Parkinson's disease.

In the diabetic patient, for example, heterologous stem cells which have been genetically altered to produce insulin at physiologically therapeutic levels can be encapsulated for delivery within the patient's tissues. Alternately, autologous stem cells can be derived from the patient's own bone marrow aspirate for transduction with a retroviral vector as previously described. Once genetically altered to produce physiologically therapeutic levels of insulin, these cells can be encapsulated as described by Chang or Baetge and introduced into the patient's tissues where they remain to produce insulin for extended periods of time.

Another advantage of microencapsulation of cells of the present invention is the opportunity to incorporate into the microcapsule a variety of cells, each producing a biologically therapeutic molecule. MASCs of the present invention can be induced to differentiate into multiple distinct lineages, each of which can be genetically altered to produce therapeutically effective levels of biologically active molecules. MASCs carrying different genetic elements can be encapsulated together to produce a variety of biologically active molecules.

MASCs of the present invention can be genetically altered ex vivo, eliminating one of the most significant barriers for gene therapy. For example, a subject's bone marrow aspirate is obtained, and from the aspirate MASCs are isolated. The MASCs are then genetically altered to express one or more desired gene products. The MASCs can then be screened or selected ex vivo to identify those cells which have been successfully altered, and these cells can be reintroduced into the subject, either locally or systemically. Alternately, MASCs can be genetically altered and cultured to induce differentiation to form a specific cell lineage for transplant. In either case, the transplanted MASCs provide a stably-transfected source of cells that can express a desired gene product. Especially where the patient's own bone marrow aspirate is the source of the MASCs, this method provides an immunologically safe method for producing transplant cells. The method can be used for treatment of diabetes, cardiac myopathy, neurodegenerative disease, and adenosine deaminase deficiency, to name only a few of a multitude of examples. In diabetes, for example, MASCs can be isolated, genetically altered to produce insulin, then transplanted into the patient suffering from the disease. Where the disease is associated with autoimmunity, MASCs can be genetically altered to express either an altered MHC or no MHC in order to avoid immune surveillance. Suppression of MHC expression in transplanted pancreatic islet cells has been successfully performed using an adenoviral vector expressing the E3 region of the viral genome. Cells of the present invention can be stably transfected or transduced, as the inventors have demonstrated, and can therefore provide a more permanent source of insulin for transplant into a diabetic patient.

Donor MASCs, particularly if genetically altered to alter MHC expression, and autologous MASCs, if genetically altered to express the desired hemoglobin gene products, can be especially effective in cell therapy for the treatment of sickle cell anemia and thalassemia.

Methods for Genetically Altering MASCs

Cells isolated by the method described herein can be genetically modified by introducing DNA or RNA into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, or direct "naked" DNA transfer. MASCs can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) expression in specific cell compartments (including but not limited to the cell membrane).

Homologous Recombination

Calcium phosphate transfection, which relies on precipitates of plasmid DNA/calcium ions, can be used to introduce plasmid DNA containing a target gene or polynucleotide into isolated or cultured MASCs. Briefly, plasmid DNA is mixed into a solution of calcium chloride, then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., ProFection® from Promega Corp., Madison, Wis.).

DEAE-dextran transfection, which is also known to those of skill in the art, may be preferred over calcium phosphate transfection where transient transfection is desired, as it is often more efficient.

Since the cells of the present invention are isolated cells, microinjection can be particularly effective for transferring genetic material into the cells. Briefly, cells are placed onto the stage of a light microscope. With the aid of the magnification provided by the microscope, a glass micropipette is guided into the nucleus to inject DNA or RNA. This method is advantageous because it provides delivery of the desired genetic material directly to the nucleus, avoiding both cytoplasmic and lysosomal degradation of the injected polynucleotide. This technique has been used effectively to accomplish germline modification in transgenic animals.

Cells of the present invention can also be genetically modified using electroporation. The target DNA or RNA is added to a suspension of cultured cells. The DNA/RNA-cell suspension is placed between two electrodes and subjected to an electrical pulse, causing a transient permeability in the cell's outer membrane that is manifested by the appearance of pores across the membrane. The target polynucleotide enters the cell through the open pores in the membrane, and when the electric field is discontinued, the pores close in approximately one to 30 minutes.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPC) can be added. A recommended reagent for liposomal transfer is Lipofectin® (Life Technologies, Inc.), which is commercially available. Lipofectin®, for example, is a mixture of the cationic lipid N-[1-(2,3-dioleyloyx)propyl]-N-N-N-trimethyl ammonia chloride and DOPE. Delivery of linear DNA, plasmid DNA, or RNA can be accomplished either in vitro or in vivo using liposomal delivery, which may be a preferred method due to the fact that liposomes can carry larger pieces of DNA, can generally protect the polynucleotide from degradation, and can be targeted to specific cells or tissues. A number of other delivery systems relying on liposomal technologies are also commercially available, including Effectene™ (Qiagen), DOTAP (Roche Molecular Biochemicals), FuGene 6™ (Roche Molecular Biochemicals), and Transfectam® (Promega). Cationic lipid-mediated gene transfer efficiency can be enhanced by incorporating purified viral or cellular envelope components, such as the purified G glycoprotein of the vesicular stomatitis virus envelope (VSV-G), in the method of Abe, A., et al. (*J. Virol.* (1998) 72: 6159-6163).

Gene transfer techniques which have been shown effective for delivery of DNA into primary and established mammalian cell lines using lipopolyamine-coated DNA can be used to introduce target DNA into MASCs. This technique is generally described by Loeffler, J. and Behr, J., *Methods in Enzymology* (1993) 217: 599-618.

Naked plasmid DNA can be injected directly into a tissue mass formed of differentiated cells from the isolated MASCs. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA.

Microprojectile gene transfer can also be used to transfer genes into MASCs either in vitro or in vivo. The basic procedure for microprojectile gene transfer was described by J. Wolff in *Gene Therapeutics* (1994) at page 195. Briefly, plasmid DNA encoding a target gene is coated onto microbeads, usually 1-3 micron sized gold or tungsten particles. The coated particles are placed onto a carrier sheet inserted above a discharge chamber. Once discharged, the carrier sheet is accelerated toward a retaining screen. The retaining screen forms a barrier which stops further movement of the carrier sheet while allowing the polynucleotide-coated particles to be propelled, usually by a helium stream, toward a target surface, such as a tissue mass formed of differentiated MASCs. Microparticle injection techniques have been described previously, and methods are known to those of skill in the art (see Johnston, S. A., et al., *Genet. Eng.* (*NY*) (1993) 15: 225-236; Williams, R. S., et al., *Proc. Natl. Acad. Sci. USA* (1991) 88: 2726-2730; Yang, N. S., et al., *Proc. Natl. Acad. Sci. USA* (1990) 87: 9568-9572).

Signal peptides can be attached to plasmid DNA, as described by Sebestyen, et al. (*Nature Biotech.* (1998) 16: 80-85), to direct the DNA to the nucleus for more efficient expression.

Viral vectors are used to genetically alter MASCs of the present invention and their progeny. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors which can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Retroviral vectors are effective for transducing rapidly-dividing cells, although a number of retroviral vectors have been developed to effectively transfer DNA into non-dividing cells as well (Mochizuki, H., et al., *J. Virol.* (1998) 72: 8873-8883). Packaging cell lines for retroviral vectors are known to those of skill in the art. Packaging cell lines provide the viral proteins needed for capsid production and virion maturation of the viral vector. Generally, these include the gag, pol, and env retroviral genes. An appropriate packaging cell line is chosen from among the known cell lines to produce a retroviral vector which is ecotropic, xenotropic, or amphotropic, providing a degree of specificity for retroviral vector systems.

A retroviral DNA vector is generally used with the packaging cell line to produce the desired target sequence/vector combination within the cells. Briefly, a retroviral DNA vector is a plasmid DNA which contains two retroviral LTRs positioned about a multicloning site and SV40 promoter so that a first LTR is located 5 to the SV40 promoter, which is operationally linked to the target gene sequence cloned into the multicloning site, followed by a 3 second LTR. Once formed, the retroviral DNA vector can be transferred into the packaging cell line using calcium phosphate-mediated transfection, as previously described. Following approximately 48 hours of virus production, the viral vector, now containing the target gene sequence, is harvested.

Targeting of retroviral vectors to specific cell types was demonstrated by Martin, F., et al., (*J. Virol.* (1999) 73: 6923-6929), who used single-chain variable fragment antibody directed against the surface glycoprotein high-molecular-weight melanoma-associated antigen fused to the amphotropic murine leukemia virus envelope to target the vector to delivery the target gene to melanoma cells. Where targeted delivery is desired, as, for example, when differentiated cells are the desired objects for genetic alteration, retroviral vectors fused to antibody fragments directed to the specific markers expressed by each cell lineage differentiated from the MASCs of the present invention can be used to target delivery to those cells.

Lentiviral vectors are also used to genetically alter cells of the invention. Many such vectors have been described in the literature and are known to those of skill in the art. Salmons, B. and Gunzburg, W. H., "Targeting of Retroviral Vectors for Gene Therapy," *Hum. Gene Therapy* (1993) 4: 129-141. These vectors have been effective for genetically altering human hematopoietic stem cells (Sutton, R., et al., *J. Virol.* (1998) 72: 5781-5788). Packaging cell lines have been described for lentivirus vectors (see Kafri, T., et al., *J. Virol.* (1999) 73: 576-584; Dull, T., et al., *J. Virol.* (1998) 72: 8463-8471).

Recombinant herpes viruses, such as herpes simplex virus type I (HSV-1) have been used successfully to target DNA delivery to cells expressing the erythropoietin receptor (Laquerre, S., et al., *J. Virol.* (1998) 72: 9683-9697). These vectors can also be used to genetically alter the cells of the present invention, which the inventors have demonstrated to be stably transduced by a viral vector.

Adenoviral vectors have high transduction efficiency, can incorporate DNA inserts up to 8 Kb, and can infect both replicating and differentiated cells. A number of adenoviral vectors have been described in the literature and are known to those of skill in the art (see, for example, Davidson, B. L., et al., *Nature Genetics* (1993) 3: 219-223; Wagner, E., et al., *Proc. Natl. Acad. Sci. USA* (1992)89: 6099-6103). Methods for inserting target DNA into an adenovirus vector are known to those of skill in the art of gene therapy, as are methods for using recombinant adenoviral vectors to introduce target DNA into specific cell types (see Wold, W., *Adenovirus Methods and Protocols*, Humana Methods in Molecular Medicine (1998), Blackwell Science, Ltd.). Binding affinity for certain cell types has been demonstrated by modification of the viral vector fiber sequence. Adenovirus vector systems have been described which permit regulated protein expression in gene transfer (Molin, M., et al., *J. Virol.* (1998) 72: 8358-8361). A system has also been described for propagating adenoviral vectors with genetically modified receptor specificities to provide transductional targeting to specific cell types (Douglas, J., et al., *Nature Biotech.* (1999) 17: 470-475). Recently described ovine adenovirus vectors even address the potential for interference with successful gene transfer by preexisting humoral immunity (Hofmann, C., et al., *J. Virol.* (1999) 73: 6930-6936).

Adenovirus vectors are also available which provide targeted gene transfer and stable gene expression using molecular conjugate vectors, constructed by condensing plasmid DNA containing the target gene with polylysine, with the polylysine linked to a replication-incompetent adenovirus. (Schwarzenberger, P., et al., *J. Virol.* (1997) 71: 8563-8571.)

Alphavirus vectors, particularly the Sindbis virus vectors, are also available for transducing the cells of the present invention. These vectors are commercially available (Invitrogen, Carlsbad, Calif.) and have been described in, for example, U.S. Pat. No. 5,843,723, as well as by Xiong, C., et al., *Science* (1989) 243: 1188-1191; Bredenbeek, P. J., et al., *J. Virol.* (1993) 67: 6439-6446; and Frolov, I., et al., *Proc. Natl. Acad. Sci. USA* (1996) 93: 11371-11377.

The inventors have shown that MASC possess good transduction potential using the eGFP-MND lentiviral vector described by Robbins, et al. (*J. Virol.* (1997) 71(12): 9466-9474) and eGFP-MGF vector. Using this method, 30-50% of MASC can be transduced after a short exposure of 4.6 hours to an enhanced green fluorescent protein (eGFP) vector containing supernatants made in PA3-17 packaging cells (an amphotropic packaging cell line derived from NIH 3T3 fibroblasts and described by Miller, A. D., and C. Buttimore in *Mol. Cell. Biol.* (1986) 6: 2895-2902), combined with protamine (8 mg/ml). Expression of eGFP persists throughout the culture of undifferentiated MASC. In addition, transfection using lipofectamine has been successfully used to introduce transgenes in MAPCs.

Successful transfection or transduction of target cells can be demonstrated using genetic markers, in a technique that is known to those of skill in the art. The green fluorescent protein of *Aequorea victoria*, for example, has been shown to be an effective marker for identifying and tracking genetically modified hematopoietic cells (Persons, D., et al., *Nature Medicine* (1998) 4: 1201-1205). Alternative selectable markers include the β-Gal gene, the truncated nerve growth factor receptor, drug selectable markers (including but not limited to NEO, MTX, hygromycin)

17. MASCs Are Useful For Tissue Repair: The stem cells of the present invention can also be used for tissue repair. The inventors have demonstrated that MASCs of the present invention differentiate to form a number of cell types, including fibroblasts, osteoblasts, chondrocytes, adipocytes, skeletal muscle, endothelium, stromal cells, smooth muscle, cardiac muscle, and hemopoietic cells. For example, MASCs induced to differentiate into osteoblasts, by the method previously described herein, can be implanted into bone to enhance the repair process, to reinforce weakened bone, or to resurface joints. MASCs induced to differentiate into chondrocytes, by the method previously described, can be injected into joints to resurface joint cartilage. Caplan, et al. (U.S. Pat. No. 5,855,619) describe a biomatrix implant including a contracted gel matrix into which mesenchymal stem cells have been incorporated. The implant is designed for repair of a tissue defect, especially for injury to tendon, ligament, meniscus, or muscle. Cartilage, for example, can be formed by the addition of chondrocytes in the immediate area around a porous, 3-dimensional scaffold made, for example, of collagen, synthetic polyglycolic acid fibers, or synthetic polylactic fibers. The inventors have shown that MASCs of the present invention differentiate to form chondrocytes, for example, which can be deposited in and around a collagen, synthetic polyglycolic, or synthetic polylactic or other scaffold material to provide an implant to facilitate tissue repair.

Matrices are also used to deliver cells of the present invention to specific anatomic sites, where particular growth factors incorporated into the matrix, or encoded on plasmids incorporated into the matrix for uptake by the cells, can be used to direct the growth of the initial cell population. DNA can be incorporated within pores of the matrix, for example, during the foaming process used in the formation of certain polymer matrices. As the polymer used in the foaming process expands, it entraps the DNA within the pores, allowing controlled and sustained release of plasmid DNA. Such a method of matrix preparation is described by Shea, et al., in *Nature Biotechnology* (1999) 17: 551-554.

Plasmid DNA encoding cytokines, growth factors, or hormones can be trapped within a polymer gene-activated matrix carrier, as described by Bonadio, J., et al., *Nature Medicine* (1999) 5: 753-759. The biodegradable polymer is then implanted near a broken bone, for example, where MASCs are implanted and take up the DNA, which causes the MASCs to produce a high local concentration of the cytokine, growth factor, or hormone, accelerating healing of the damaged tissue.

Cells provided by the present invention, or MASCs isolated by the method of the present invention, can be used to produce tissues or organs for transplantation. Oberpenning, et al. (*Nature Biotechnology* (1999) 17: 149-155) reported the formation of a working bladder by culturing muscle cells from the exterior canine bladder and lining cells from the interior of the canine bladder, preparing sheets of tissue from these cultures, and coating a small polymer sphere with muscle cells on the outside and lining cells on the inside. The sphere was then inserted into a dog's urinary system, where it began to function as a bladder. Nicklason, et al., *Science* (1999) 284: 489-493, reported the production of lengths of vascular graft material from cultured smooth muscle and endothelial cells. Other methods for forming tissue layers from cultured cells are known to those of skill in the art (see, for example, Vacanti, et al., U.S. Pat. No. 5,855,610). These methods can be especially effective when used in combination with cells of the present invention, which have a broader range of differentiation than any previously-described non-embryonic stem cells.

MASCs of the present invention can be used to repopulate heart muscle cells by either direct injection into the area of tissue damage or by systemic injection, allowing the cells to home to the cardiac tissues. This method can be particularly effective if combined with angiogenesis. Both the methods of injection and methods for promoting angiogenesis are known to those of skill in the art. The MASCs of the present invention provide a broader differentiation range to provide a more varied source of cells for cardiac or other tissue repair utilizing these techniques.

MASCs of the present invention are also useful, for example, for the purpose of repopulating the bone marrow after high dose chemotherapy. Prior to chemotherapy, a bone marrow aspirate is obtained from the patient. Stem cells are isolated by the method of the present invention, and are grown in culture and induced to differentiate. A mixture of differentiated and undifferentiated cells is then reintroduced into the patient's bone marrow space. Clinical trials are currently underway using hematopoietic stem cells for this purpose. The MASCs of the present invention, however, provide the additional benefit of further differentiation to form cells that can replace those damaged by chemotherapy in other tissues as well as in bone marrow.

Alternately, the method described by Lawman, et al. (WO 98/42838) can be used to change the histocompatibility antigen of stem cells from an allogeneic donor or donors. Using this method, panels of available bone marrow transplants can be generated for preparation of frozen stocks, storage, and administration to patients who are unable, as in leukemia patients, for example, to provide their own bone marrow for reconstitution.

Re-population of a patient's immune system cells or blood cells can be accomplished, for example, by isolating autologous stem cells from the patient, culturing those cells to expand the population, then reintroducing the cells into the patient. This method can be particularly effective where the immune system or bone marrow cells must be depleted by radiation and/or chemotherapy for therapeutic purposes, such as in the case, for example, of patients diagnosed with multiple myeloma, non-Hodgkins lymphoma, autoimmune disease, or solid tumor cancers.

For the treatment of leukemias, autoimmune disease, or genetic diseases such as sickle cell anemia or thalassemia, re-population of the patient's blood or immune system cells with allogeneic cells of the present invention, or isolated by the method of the present invention, can be performed, particularly when the histocompatibility antigen has been altered in the manner described by Lawman, et al. (WO 98/42838).

For the purposes described herein, either autologous or allogeneic MASCs of the present invention can be administered to a patient, either in differentiated or undifferentiated form, genetically altered or unaltered, by direct injection to a tissue site, systemically, on or around the surface of an acceptable matrix, or in combination with a pharmaceutically acceptable carrier.

19. MASCs Provide a Model System for Studying Differentiation Pathways: Cells of the present invention are useful for further research into developmental processes, as well. Ruley, et al. (WO 98/40468), for example, have described vectors and methods for inhibiting expression of specific genes, as well as obtaining the DNA sequences of those inhibited genes. Cells of the present invention can be treated with the vectors such as those described by Ruley, which inhibit the expression of genes that can be identified by DNA sequence analysis. The cells can then be induced to differentiate and the effects of the altered genotype/phenotype can be characterized.

Hahn, et al. (Nature (1999) 400: 464-468) demonstrated, for example, that normal human epithelial fibroblast cells can be induced to undergo tumorigenic conversion when a combination of genes, previously correlated with cancer, were introduced into the cells.

Control of gene expression using vectors containing inducible expression elements provides a method for studying the effects of certain gene products upon cell differentiation. Inducible expression systems are known to those of skill in the art. One such system is the ecdysone-inducible system described by No, D., et al. *Proc. Natl. Acad. Sci. USA* (1996) 93: 3346-3351.

MASCs can be used to study the effects of specific genetic alterations, toxic substances, chemotherapeutic agents, or other agents on the developmental pathways. Tissue culture techniques known to those of skill in the art allow mass culture of hundreds of thousands of cell samples from different individuals, providing an opportunity to perform rapid screening of compounds suspected to be, for example, teratogenic or mutagenic.

For studying developmental pathways, MASCs can be treated with specific growth factors, cytokines, or other agents, including suspected teratogenic chemicals. MASCs can also be genetically modified using methods and vectors previously described. Furthermore, MASCs can be altered using antisense technology or treatment with proteins introduced into the cell to alter expression of native gene sequences. Signal peptide sequences, for example, can be used to introduce desired peptides or polypeptides into the cells. A particularly effective technique for introducing polypeptides and proteins into the cell has been described by Rojas, et al., in *Nature Biotechnology* (1998) 16: 370-375. This method produces a polypeptide or protein product that can be introduced into the culture media and translocated across the cell membrane to the interior of the cell. Any number of proteins can be used in this manner to determine the effect of the target protein upon the differentiation of the cell. Alternately, the technique described by Phelan et al. (*Nature Biotech*. (1998) 16: 440-443) can be used to link the herpes virus protein VP22 to a functional protein for import into the cell.

Cells of the present invention can also be genetically engineered, by the introduction of foreign DNA or by silencing or excising genomic DNA, to produce differentiated cells with a defective phenotype in order to test the effectiveness of potential chemotherapeutic agents or gene therapy vectors.

20. MASCs Provide a Variety of Differentiated and Undifferentiated Cultured Cell Types for High-Throughput Screening: MASCs of the present invention can be cultured in, for example, 96-well or other multi-well culture plates to provide a system for high-throughput screening of, for example, target cytokines, chemokines, growth factors, or pharmaceutical compositions in pharmacogenomics or pharmacogenetics. The MASCs of the present invention provide a unique system in which cells can be differentiated to form specific cell lineages from the same individual. Unlike most primary cultures, these cells can be maintained in culture and can be studied over time. Multiple cultures of cells from the same individual and from different individuals can be treated with the factor of interest to determine whether differences exist in the effect of the cellular factor on certain types of differentiated cells with the same genetic makeup or on similar types of cells from genetically different individuals. Cytokines, chemokines, pharmaceutical compositions and growth factors, for example, can therefore be screened in a timely and cost-effective manner to more clearly elucidate their effects. Cells isolated from a large population of individuals and characterized in terms of presence or absence of genetic polymorphisms, particularly single nucleotide polymorphisms, can be stored in cell culture banks for use in a variety of screening techniques. For example, multipotent adult stem cells from a statistically significant population of individuals, which can be determined according to methods known to those of skill in the art, provide an ideal system for high-throughput screening to identify polymorphisms associated with increased positive or negative response to a range of substances such as, for example, pharmaceutical compositions, vaccine preparations, cytotoxic chemicals, mutagens, cytokines, chemokines, growth factors, hormones, inhibitory compounds, chemotherapeutic agents, and a host of other compounds or factors. Information obtained from such studies has broad implication for the treatment of infectious disease, cancer, and a number of metabolic diseases.

In the method of using MASCs to characterize cellular responses to biologic or pharmacologic agents, or combinatorial libraries of such agents, MASCs are isolated from a statistically significant population of individuals, culture expanded, and contacted with one or more biologic or pharmacologic agents. MASCs can be induced to differentiate, where differentiated cells are the desired target for a certain biologic or pharmacologic agent, either prior to or after culture expansion. By comparing the one or more cellular responses of the MASC cultures from individuals in the statistically significant population, the effects of the biologic or pharmacologic agent can be determined. Alternately, genetically identical MASCs, or cells differentiated therefrom, can be used to screen separate compounds, such as compounds of a combinatorial library. Gene expression systems for use in combination with cell-based high-throughput screening have been described (see Jayawickreme, C. and Kost, T., *Curr. Opin. Biotechnol.* (1997) 8: 629-634). A high volume screening technique used to identify inhibitors of endothelial cell activation has been described by Rice, et al., which utilizes a cell culture system for primary human umbilical vein endothelial cells. (Rice, et al., *Anal. Biochem.* (1996) 241: 254-259.) The cells of the present invention provide a variety of cell types, both terminally differentiated and undifferentiated, for high-throughput screening techniques used to identify a multitude of target biologic or pharmacologic agents. Most important, the cells of the present invention provide a source of cultured cells from a variety of genetically diverse individuals who may respond differently to biologic and pharmacologic agents.

MASCs can be provided as frozen stocks, alone or in combination with prepackaged medium and supplements for their culture, and can be additionally provided in combination with separately packaged effective concentrations of appropriate factors to induce differentiation to specific cell types. Alternately, MASCs can be provided as frozen stocks, prepared by methods known to those of skill in the art, containing cells induced to differentiate by the methods described hereinabove.

21. MASCs and Genetic Profiling: Genetic variation can have indirect and direct effects on disease susceptibility. In a direct case, even a single nucleotide change, resulting in a single nucleotide polymorphism (SNP), can alter the amino acid sequence of a protein and directly contribute to disease or disease susceptibility. Functional alteration in the resulting protein can often be detected in vitro. For example, certain APO-lipoprotein E genotypes have been associated with onset and progression of Alzheimer's disease in some individuals.

DNA sequence anomalies can be detected by dynamic-allele specific hybridization, DNA chip technologies, and other techniques known to those of skill in the art. Protein coding regions have been estimated to represent only about 3% of the human genome, and it has been estimated that there are perhaps 200,000 to 400,000 common SNPs located in coding regions.

Previous investigational designs using SNP-associated genetic analysis have involved obtaining samples for genetic analysis from a large number of individuals for whom phenotypic characterization can be performed. Unfortunately, genetic correlations obtained in this manner are limited to identification of specific polymorphisms associated with readily identifiable phenotypes, and do not provide further information into the underlying cause of the disease.

MASCs of the present invention provide the necessary element to bridge the gap between identification of a genetic element associated with a disease and the ultimate phenotypic expression noted in a person suffering from the disease. Briefly, MASCs are isolated from a statistically significant population of individuals from whom phenotypic data can be obtained (see Collins, et al., *Genome Research* (1998) 8: 1229-1231). These MASC samples are then cultured expanded and subcultures of the cells are stored as frozen stocks, which can be used to provide cultures for subsequent developmental studies. From the expanded population of cells, multiple genetic analyses can be performed to identify genetic polymorphisms. For example, single nucleotide polymorphisms can be identified in a large sample population in a relatively short period of time using current techniques, such as DNA chip technology, known to those of skill in the art (Wang, D., et al., *Science* (1998) 280: 1077-1082; Chee, M., et al., *Science* (1996) 274: 610-614; Cargill, M., et al., *Nature Genetics* (1999) 22: 231-238; Gilles, P., et al., *Nature Biotechnology* (1999) 17: 365-370; Zhao, L. P., et al., *Am. J. Human Genet.* (1998) 63: 225-240). Techniques for SNP analysis have also been described by Syvänen (Syvänen, A., *Hum. Mut.* (1999) 13: 1-10), Xiong (Xiong, M. and L. Jin, *Am. J. Hum. Genet.* (1999) 64: 629-640), Gu (Gu, Z., et al., Human Mutation (1998) 12: 221-225), Collins (Collins, F., et al., *Science* (1997) 278: 1580-1581), Howell (Howell, W., et al., *Nature Biotechnology* (1999) 17: 87-88), Buetow (Buetow, K., et al., *Nature Genetics* (1999) 21: 323-325), and Hoogendoorn (Hoogendoorn, B., et al., *Hum. Genet.* (1999) 104: 89-93).

When certain polymorphisms are associated with a particular disease phenotype, cells from individuals identified as carriers of the polymorphism can be studied for developmental anomalies, using cells from non-carriers as a control. MASCs of the present invention provide an experimental system for studying developmental anomalies associated with particular genetic disease presentations, particularly, since they can be induced to differentiate, using certain methods described herein and certain other methods known to those of skill in the art, to form particular cell types. For example, where a specific SNP is associated with a neurodegenerative disorder, both undifferentiated MASCs and MASCs differentiated to form neuronal precursors, glial cells, or other cells of neural origin, can be used to characterize the cellular effects of the polymorphism. Cells exhibiting certain polymorphisms can be followed during the differentiation process to identify genetic elements which affect drug sensitivity, chemokine and cytokine response, response to growth factors, hormones, and inhibitors, as well as responses to changes in receptor expression and/or function. This information can be invaluable in designing treatment methodologies for diseases of genetic origin or for which there is a genetic predisposition.

In the present method of using MASCs to identify genetic polymorphisms associated with physiologic abnormalities, MASCs are isolated from a statistically significant population of individuals from whom phenotypic data can be obtained (a statistically significant population being defined by those of skill in the art as a population size sufficient to include members with at least one genetic polymorphism) and culture expanded to establish MASC cultures. DNA from the cultured cells is then used to identify genetic polymorphisms in the cultured MASCs from the population, and the cells are induced to differentiate. Aberrant metabolic processes associated with particular genetic polymorphisms are identified and characterized by comparing the differentiation patterns exhibited by MASCs having a normal genotype with differentiation patterns exhibited by MASCs having an identified genetic polymorphism or response to putative drugs.

22. MASCs Provide Safer Vaccine Delivery: MASCs cells of the present invention can also be used as antigen-presenting cells when genetically altered to produce an antigenic protein. Using multiple altered autologous or allogeneic progenitor cells, for example, and providing the progenitor cells of the present invention in combination with plasmids embedded in a biodegradable matrix for extended release to transfect the accompanying cells, an immune response can be elicited to one or multiple antigens, potentially improving the ultimate effect of the immune response by sequential release of antigen-presenting cells. It is known in the art that multiple administrations of some antigens over an extended period of time produce a heightened immune response upon ultimate antigenic challenge. Alternately, MASCs can be used as antigen-presenting cells, in the method of Zhang, et al. (*Nature Biotechnology* (1998) 1: 1045-1049), to induce T-cell tolerance to specific antigen.

Many current vaccine preparations incorporate added chemicals and other substances, such as antibiotics (to prevent the growth of bacteria in vaccine cultures), aluminum (adjuvant), formaldehyde (to inactivate bacterial products for toxoid vaccines), monosodium glutamate (stabilizer), egg protein (component of vaccines prepared using embryonated chicken eggs), sulfites (stabilizer), and thimerosol (a preservative). Partly due to these added components, there is currently a broad-based public concern over the safety of vaccine preparations. Thimerosol, for example, contains mercury and is made from a combination of ethyl mercuric chloride, thiosalicylic acid, sodium hydroxide and ethanol. Furthermore, some studies, although inconclusive, have suggested a possible link between some vaccine components and potential complications such as those diseases commonly associated with autoimmunity. Thus, more effective vaccine therapies are needed and public cooperation with vaccine initiatives will be easier to promote if there is a greater degree of comfort with the method of vaccination.

MASCs of the present invention can be differentiated to form dendritic cells, which present antigen to T cells and thereby activate them to respond against foreign organisms. These dendritic cells can be genetically altered to express foreign antigens, using techniques previously described. A particular advantage of this method of vaccine delivery lies in the fact that more than one antigen can be presented by a single genetically altered cell.

Differentiated or undifferentiated MASC vaccine vectors of heterologous origin provide the added advantage of stimulating the immune system through foreign cell-surface markers. Vaccine design experiments have shown that stimulation of the immune response using multiple antigens can elicit a heightened immune response to certain individual antigens within the vaccine preparation.

Immunologically effective antigens have been identified for hepatitis A, hepatitis B, varicella (chickenpox), polio, diphtheria, pertussis, tetanus, Lyme disease, measles, mumps, rubella, Haemophilus influenzae type B (Hib), BCG, Japanese encephalitis, yellow fever, and rotavirus, for example.

The method for inducing an immune response to an infectious agent in a human subject using MASCs of the present invention can be performed by expanding a clonal population of multipotent adult stem cells in culture, genetically altering the expanded cells to express one or more pre-selected antigenic molecules to elicit a protective immune response against an infectious agent, and introducing into the subject an amount of genetically altered cells effective to induce the immune response. Methods for administering genetically altered cells are known to those of skill in the art. An amount of genetically altered cells effective to induce an immune response is an amount of cells which produces sufficient expression of the desired antigen to produce a measurable antibody response, as determined by methods known to those of skill in the art. Preferably, the antibody response is a protective antibody response that can be detected by resistance to disease upon challenge with the appropriate infectious agent.

23. MASCs and Cancer Therapy: MASCs of the present invention provide a novel vehicle for cancer therapies. For example, MASCs can be induced to differentiate to form endothelial cells or precursors which will home to endothelial tissues when delivered either locally or systemically. The cells participate in formation of blood vessels to supply newly-formed tumors (angiogenesis), and divide and proliferate in the endothelial tissue accordingly. By genetically engineering these cells to undergo apoptosis upon stimulation with an externally-delivered element, the newly-formed blood vessels can be disrupted and blood flow to the tumor can be eliminated. An example of an externally-delivered element would be the antibiotic tetracycline, where the cells have been transfected or transduced with a gene which promotes apoptosis, such as Caspase or BAD, under the control of a tetracycline response element. Tetracycline responsive elements have been described in the literature (Gossen, M. & Bujard, H., Proc. Natl. Acad. Sci. USA (1992) 89: 5547-5551), provide in vivo transgene expression control in endothelial cells (Sarao, R. & Dumont, D., Transgenic Res. (1998) 7: 421-427), and are commercially available (CLONETECH Laboratories, Palo Alto, Calif.).

Alternately, undifferentiated MASCs or MASCs differentiated to form tissue-specific cell lineages can be genetically altered to produce a product, for export into the extracellular environment, which is toxic to tumor cells or which disrupts angiogenesis (such as pigment epithelium-derived factor (PEDF), described by Dawson, et al., *Science* (1999) 285: 245-248). For example, Koivunen, et al., describe cyclic peptides containing an amino acid sequence which selectively inhibits MMP-2 and MMP-9 (matrix metalloproteinases associated with tumorigenesis), preventing tumor growth and invasion in animal models and specifically targeting angiogenic blood vessels in vivo (Koivunen, E., Nat. Biotech. (1999) 17: 768-774). Where it is desired that cells be delivered to the tumor site, produce a tumor-inhibitory product, and then be destroyed, cells can be further genetically altered to incorporate an apoptosis-promoting protein under the control of an inducible promoter.

MASCs also provide a vector for delivery of cancer vaccines, since they can be isolated from the patient, cultured ex vivo, genetically altered ex vivo to express the appropriate antigens, particularly in combination with receptors associated with increased immune response to antigen, and reintroduced into the subject to invoke an immune response to the protein expressed on tumor cells.

24. Kits Containing MASCs or MASC Isolation and Culture Components: MASCs of the present invention can be provided in kits, with appropriate packaging material. For example, MASCs can be provided as frozen stocks, accompanied by separately packaged appropriate factors and media, as previously described herein, for culture in the undifferentiated state. Additionally, separately packaged factors for induction of differentiation, as previously described, can also be provided.

Kits containing effective amounts of appropriate factors for isolation and culture of a patient's stem cells are also provided by the present invention. Upon obtaining a bone marrow aspirate from the patient, the clinical technician only need select the stem cells, using the method described herein, with the anti-CD45 and anti-glycophorin A provided in the kit, then culture the cells as described by the method of the present invention, using culture medium supplied as a kit component. The composition of the basic culture medium has been previously described herein.

One aspect of the invention is the preparation of a kit for isolation of MASCs from a human subject in a clinical setting. Using kit components packaged together, MASCs can be isolated from a simple bone marrow aspirate. Using additional kit components including differentiation factors, culture media, and instructions for inducing differentiation of MASCs in culture, a clinical technician can produce a population of antigen-presenting cells (APCs) from the patient's own bone marrow sample. Additional materials in the kit can provide vectors for delivery of polynucleotides encoding appropriate antigens for expression and presentation by the differentiated APCs. Plasmids, for example, can be supplied which contain the genetic sequence of, for example, the hepatitis B surface antigen or the protective antigens of hepatitis A, adenovirus, *Plasmodium falciparum*, or other infectious organisms. These plasmids can be introduced into the cultured APCs using, for example, calcium phosphate transfection materials, and directions for use, supplied with the kit. Additional materials can be supplied for injection of genetically-altered APCs back into the patient, providing an autologous vaccine delivery system.

The invention will be further described by reference to the following detailed examples.

EXAMPLES

Example 1

Isolation of MASCs from Bone Marrow Mononuclear Cells

Bone marrow mononuclear cells were obtained from bone marrow aspirates from the posterior iliac crest of >80 healthy human volunteers. Ten to 100 cubic centimeters of bone marrow was obtained from each subject, as shown in Table 2, which indicates the approximate number of mononuclear cells isolated from each subject. Mononuclear cells (MNC) were obtained from bone marrow by centrifugation over a Ficoll-Paque density gradient (Sigma Chemical Co, St Louis, Mo.). Bone marrow MNC were incubated with CD45 and Glycophorin A microbeads (Miltenyi Biotec, Sunnyvale, Calif.) for 15 minutes and CD45$^+$/Gly-A$^+$ cells removed by placing the sample in front of a SuperMACS magnet. The eluted cells are 99.5% CD45$^-$/GlyA$^-$.

As shown in Table 2, depletion of CD45$^+$GlyA$^+$ cells resulted in recovery of CD45– GlyA– cells which constituted approximately 0.05 to 0.10% of the total bone marrow mononuclear cells.

TABLE 2

| Volume of Bone Marrow (cc) | Number of mononuclear BM cells post ficolled | Number of 45-/GlyA-cell post-MACS | Number of MASCs (estimated by limiting dilution assay, LDA) |
|---|---|---|---|
| 50 | 100 millions | 100,000 | 50 |
| 25 | 80 | 60,000 | 35 |
| 25 | 50 | 14,000 | 10 |
| 50 | 100 | 50,000 | 30 |
| 10 | 150 | 75,000 | 30 |
| 30 | 100 | 100,000 | 25 |

TABLE 2-continued

| Volume of Bone Marrow (cc) | Number of mononuclear BM cells post ficolled | Number of 45-/GlyA-cell post-MACS | Number of MASCs (estimated by limiting dilution assay, LDA) |
|---|---|---|---|
| 25 | 80 | 75,000 | 35 |
| 100 | 190 | 78,000 | 25 |
| 100 | 150 | 60,000 | 15 |
| 100 | 160 | 160,000 | 85 |
| 100 | 317 | 400,000 | 50 |
| 100 | 200 | 150,000 | 70 |
| 50 | 160 | 160,000 | 85 |
| 50 | 115 | 150,000 | 70 |
| 25 | 60 | 60,000 | 30 |
| 100 | 307 | 315,000 | 100 |
| 100 | 216 | 140,000 | 80 |
| 50 | 130 | 150,000 | 40 |
| 100 | 362 | 190,000 | 60 |
| 50 | 190 | 150,000 | 40 |
| 100 | 200 | 185,000 | 100 |
| 100 | 387 | 300,000 | 170 |
| 50 | 100 | 130,000 | 20 |
| 150 | 588 | 735,000 | 300 |

We selected cells that do not express the common leukocyte antigen, CD45, or the erythroid precursor marker, glycophorin-A (GlyA). CD45⁻GlyA⁻ cells constitute $1/10^3$ marrow mononuclear cells. CD45⁻GlyA⁻ cells were plated in wells coated with fibronectin in with 2% FCS, and EGF, PDGF-BB, dexamethasone, insulin, linoleic acid, and ascorbic acid. After 7-21 days, small clusters of adherent cells developed. Using limiting dilution assays, we determined that the frequency of cells giving rise to these adherent clusters is $1/5 \times 10^3$ CD45⁻ GlyA⁻ cells.

When colonies appeared (about $10^3$ cells) cells were recovered by trypsinization and re-plated every 3-5 days at a 1:4 dilution under the same culture conditions. Cell densities were maintained between $2\text{-}8 \times 10^3$ cells/cm². Cell doubling time was 48-60 h. Immunophenotypic analysis by FACS of cells obtained after 10-12 cell doubling showed that cells did not express CD31, CD34, CD36, CD38, CD45, CD50, CD62E and CD62-P, Muc18, cKit, Tie/Tek, and CD44. Cells expressed no HLA-DR or HLA-class-I and expressed low levels of β2-microglobulin. Cells stained highly positive with antibodies against CD10, CD13, CD49b, CD49e, CDw90, Flk1. The MASC phenotype remained unchanged for >30 cell doublings (n=15). MASC cultures with cells capable of proliferating beyond 30 cell doublings and differentiating to all mesodermal cell-types (see below) have been established from >85% of donors, age 2-50 years. In 10 donors, we have expanded MASC for >50 cell doublings. When cells were cultured in serum-free medium, also supplemented with 10 ng/mL IGF, cell doubling was slower (>60 h), but >40 cell doublings could be obtained. As was seen for cells cultured with 2% FCS without IGF, cells cultured in serum-free medium were HLA-class-I and CD44 negative, and could differentiate into all mesodermal phenotypes, as described below.

When cells were plated on collagen-type-I or laminin in stead of fibronectin, they expressed CD44 and HLA-DR, and could not be expanded beyond 30 cell doublings. When EGF or PDGF were omitted cells did not proliferate and died, while increased concentrations of these cytokines allowed initial growth of MASC but caused loss of proliferation beyond 20-30 cell doublings. Addition of higher concentrations of dexamethasone also caused loss of proliferation beyond 30 cell doubling. When cells were cultured with >2% FCS in the culture medium they expressed CD44, HLA-DR and HLA-class-I. Likewise, culture at high density ($>8 \times 10^3$ cells/cm²) was associated with the acquisition of CD44, HLA-DR and HLA-class-I and Muc-18, which is similar to the phenotype described for MASC. Culture at high density or with higher concentrations of FCS was also associated with loss of expansion capacity, and cells did not proliferate beyond 25-30 cell doublings.

We attempted to clone MASC by replating MASC at 1 cell/well once cultures had been established. From 3 donors, we plated >2000 cells singly in FN coated 96 well plates with the same culture medium. In no well did we detect cell growth. Of note, when cells were deposited at 10 cells/well, we found cell growth in approximately 4% of wells. Progeny of 5% of these wells could be expanded to >$10^7$ cells.

Telomere length of MASC from 5 donors (age 2-50 years) cultured for 15 cell doublings was between 11-16 kB. In 3 donors, this was 3 kB longer than telomere length of blood lymphocytes obtained from the same donors. Telomere length of cells from 1 donor evaluated after 15 cell doublings, 30 cells doublings and 45 cell doublings remained unchanged. Cytogenetic analysis of MASC recovered after 30 cell doublings showed a normal karyotype.

Example 2

Differentiation of MASCs

To induce osteoblast differentiation, serum-free medium was supplemented with $10^{-7}$ M of dexamethasone, 10 mM ascorbic acid, and 10 mM-glycerophosphate. Osteoblast differentiation was confirmed by detection of calcium mineralization, alkaline phosphatase expression, and production of bone sialoprotein, osteopontin, osteocalcin and osteonectin, which are relatively specific for bone development (see FIG. 7).

To induce differentiation into cartilage, serum-free medium, as previously described, was supplemented with 100 ng/ml TGF-1 (R&D Systems, Minneapolis, Minn.). Cells were induced to differentiate while adherent to fibronectin, or in suspension culture, with both methods producing differentiated cartilage cells. Differentiation to form cartilage cells was confirmed by detection of collagen type II, as well as the glycosaminoglycan aggrecan (see FIG. 7).

To induce adipocyte differentiation, $10^{-7}$ M dexamethasone and 100 μg/ml insulin were added to the culture medium. Adipocyte differentiation was also induced by replacing serum-free medium with medium containing 20% horse serum. Adipocyte differentiation was detected by detection of LPL and aP2.

To induce skeletal myocyte differentiation, >80% confluent MASCs were treated with either 3 μM 5-azacytidine for 24 h and then maintained in MASC medium with EGF and PDGF-BB, expression of muscle specific proteins was seen as early as 5 days after changing culture conditions. Two days after induction, we detected the Myf5, Myo-D and Myf6 transcription factors. After 14-18 days, Myo-D was expressed at significantly lower levels, whereas Myf5 and Myf6 persisted. We detected desmin and sarcomeric actin as early as 4 days after induction, and fast-twitch and slow-twitch myosin at 14 days (FIG. 7). By immunohistochemistry, 70-80% of cells expressed mature muscle proteins after 14 days. When we added 20% horse serum we demonstrated fusion of myoblasts into myotubes that were multinucleated (FIG. 7). Of note, treatment with 5-azacytidine also induced expression of Gata4 and Gata6 during the first week of culture, and cardiac troponin-T after 14 days. In addition, smooth muscle actin was detected at 2 days after induction and persisted till 14 days.

Smooth muscle cell differentiation was when we added 100 ng/mL PDGF as the sole cytokine to confluent MASC maintained in serum-free MASC medium for 14 days. Cells expressed markers of smooth muscle (FIG. x). We found presence of myogenin from day 4 on and desmin after 6 days. Smooth muscle actin was detected from day 2 on and smooth muscle myosin after 14 days. After 14 days, approximately 70% of cells stained positive with anti-smooth muscle actin and myosin antibodies. We could also detect Myf5 and Myf6 proteins, but not Myo-D after 2-4 days, which persisted till day 15. (FIG. 7).

Cardiac muscle differentiation was induced by adding 100 ng/ml basic fibroblast growth factor (bFGF) to the standard serum-free culture media previously described herein. Cells were confluent at onset of bFGF treatment. To induce further development of cardiac tissues, 100 ng/ml 5-azacytidine, 100 ng/ml bFGF, and 25 ng/ml bone morphogenetic proteins 2 and 4 (BMP-2 and BMP-4) were added to the culture medium. Cells were >80% confluent at onset of treatment to induce cardiac tissue differentiation. Gata4 and Gata6 were expressed as early as day 2 and persisted till day 15. Expression of Myf6 and desmin was seen after day 2 and myogenin after day 6. Cardiac troponin-T was expressed after day 4 and cardiac troponin-I and ANP after day 11. These mature cardiac proteins were detected in >70% of cells by immunohistochemistry on day 15. When the cultures were maintained for >3 weeks, cells formed syncithia and we saw infrequent spontaneous contractions occurring in the cultures, which were propagated over several mm distance. (FIG. 7) Again, we also detected Myf5 and myf6 and smooth muscle actin after day 6.

Vascular endothelial growth factor (VEGF), at a concentration of 20 ng/ml, was added to serum-free medium minus other growth factors to induce endothelial cell differentiation by day 15-20 ex vivo. Endothelial cell differentiation was confirmed by immunofluorescence staining to detect cellular proteins and receptors associated with endothelial cell differentiation. Results are shown in FIG. 7.

Hematopoietic differentiation was induced by culturing MASCs in collagen type IV coated wells with in PDGF-BB- and EGF-containing MASC medium with 5% FCS and 100 ng/mL SCF that was conditioned by the AFT024 feeder, a fetal liver derived mesenchymal line that supports murine and human repopulating stem cells ex vivo. Cells recovered from these cultures expressed cKit, cMyb, Gata2 and G-CSF-R but not CD34 (RT-PCR). Because hemopoiesis is induced by factors that are released by embryonal visceral endoderm, we co-cultured human MASCs with βGal+ murine EBs in the presence of human SCF, Flt3-L, Tpo and Epo. In 2 separate studies, we detected a small population of βGal− cells that expressed human CD45

We induced "stromal" differentiation by incubating MASC with IL-1α, FCS, and horse serum. To demonstrate that these cells can support hemopoiesis, feeders were irradiated at 2Gy and CD34+ cord blood cells plated in contact with the feeder. After 2 weeks, progeny was replated in methylcellulose assay to determine the number of colony forming cells (CFC). A 3-5-fold expansion of CFC was seen.

Confluent MASC cultures were treated with hepatocyte growth factor (HFG) and KGF. After 14 days, cells expressed MET (the HGF receptor), associated with hepatic epithelial cell development, cytokeratin 18 and 19.

Example 4

Transduction of MASCs from Adult Marrow

Once MASC cultures have been established after about 3-10 subcultures, MASCs were retrovirally transduced with an enhanced green fluorescence protein (eGFP) containing vector on two consecutive days. Retroviral vectors that were used were the MFG-eGFP or MND-eGFP-SN constructs, kindly provided by Donald Kohn, M.D., LA Childrens Hospital, Los Angeles, Calif. Both vectors were packaged in the amphotropic cell line PA317 or the Gibon-ape leukemia packaging cell line PG13. Retroviral supernatant was produced by incubating the producer feeder with MASCs expansion medium for 48 hours. Supernatant was filtered and frozen at −80° C. until use. Semiconfluent MASCs were subcultured in MASCs expansion culture medium. After 24 hours media was replaced with retrovirus containing supernatants and 8 g/mL protamine (Sigma) for 5 hours. This was repeated 24 hours later. Two to three days after the last transduction, eGFP+ cells were selected on a FACS Star Plus Flow cytometer with a Consort computer (all from Becton Dickinson Inc) at 10 cells/well of 96 well plates coated with 5 ng/mL FN, and 40-85% of adherent cells expressed the eGFP gene. Using the automatic cell deposition unit (ACDU) on the fluorescence activated cell sorter, 10 eGFP+ cells per well of 96 well plates coated with fibronectin were sorted. Cells were maintained in MASCs expansion medium for 1-7 months. After 3-4 weeks, adherent cells had reached confluence in 3-4% of the wells. The cells were again culture expanded. Progeny of <1 well per plate could be expanded to generate >$10^7$ cells (an additional 48 cell doublings). Thus, $1/10^7$-$1/10^8$ bone marrow cells has extensive proliferative potential.

The clonal expanded cell populations were then divided in 5-10 populations. Some cells were cryopreserved undifferentiated, whereas other cells were induced to differentiate into osteoblasts, chondrocytes, stromal cells, skeletal and smooth muscle myoblasts and endothelial cells. To demonstrate differentiation along a given pathway, and to confirm tissue identity, cells were either examined by immunohistochemistry and/or Western blot for proteins known to be present in the differentiated cell types.

Single cell sorting or ring cloning has been used to show single cell origin of a cell population. However, because MASC are adherent cells it is possible that two rather than a single cell are selected by FACS or by ring cloning. The fact that integration of retroviruses is random was used to prove clonal origin of all differentiated cells. Because of the random viral integration, the host cell DNA that flanks the retroviral LTR is cell specific. Upon cell division, all daughter cells can be identified based on presence of the retrovirus in the identical location in the host cell genome.

Inverse polymerase chain reaction (PCR) was used to amplify the host cell DNA flanking the 3 and the 5 LTR of the retroviral insert. Inverse PCR was done using a protocol kindly provided to us by Jan Nolta, Ph.D., LA Children Hospital, Los Angeles, Calif. Briefly, DNA was extracted from undifferentiated MASC as well as from differentiated progeny, cut with Taq1 (Invitrogen) the fragments ligated and inverse PCR performed to obtain the sequence of the 5' flanking host cell DNA. This inverse PCR technique or Southern blot analysis have extensively been used in hematopoietic stem cell biology to demonstrate that every differentiated lineage is derived from a single cell. Once the flanking DNA had been amplified, 200-300 bases were sequenced and primers were designed that specifically recognize the flanking DNA. Undifferentiated and differentiated cells were then subjected to PCR using one primer specific for the flanking DNA and one primer that recognizes the 5' long terminal repeat (LTR) to amplify DNA from the differentiated progeny. For each of the 3 samples that were examined a single cell specific DNA sequence flanking the 5' LTR, which was identical for undifferentiated and differentiated cells was identified. This proves single cell origin of all cells of "mesodermal" origin.

Using this technique, the present studies confirm that osteoprogenitor cells exist in marrow and these cells can differentiate into osteoblasts, chondrocytes, adipocytes, fibroblasts, and marrow stromal cells. The present inventors also demonstrate that a single marrow derived cell can give rise to cells from both splanchnic and visceral mesoderm. Further, the karyotype of cells that have been cultured for more than nine months is normal indicating that their massive expansion capacity is due to their stem cell nature or not because of tumor genesis or immortalization.

Example 5

Generation of Glial and Neuronal Cells from Adult Bone Marrow Mesenchymal Stem Cells Differentiated neurons are post-mitotic and little or no neuronal regeneration is observed in vivo. Therapies for neurodegenerative and traumatic disorders of the brain may be significantly furthered if new, proliferating neural stem cells (NSC) could be introduced in the defective areas of the brain which would resume the function of the defective tissue. It has now been discovered that MASCs selected from post-natal bone marrow that differentiate to all mesodermal cell types can also differentiate to neurons, oligodendrocytes, and astrocytes.

MASC cultures were established as described in example 1. Neural development was induced as follows. Generation of neurons, astrocytes and oligodendrocytes was done in medium consisting of neural differentiation medium. This medium comprised the following: 10-95% DMEM-LG (preferably about 60%), 5-90% MCDB-201 (preferably about 40%), 1× ITS, 1× LA-BSA, $10^{-7}$ to $10^{-9}$ M Dexamethasone (preferably about $10^{-8}$ M), $10^{-3}$ to $10^{-5}$ M ascorbic acid 2-phosphate (preferably about $10^{-4}$ M) and 0.5-100 ng/mL EGF (preferably about 10 ng/mL). The medium may also contain one or more of the following cytokines in order to induce differentiation into certain cell types:
- 5-50 ng/mL bFGF (preferably about 100 ng/mL)—astrocyte, oligodendrocyte, neuron (type unknown));
- 5-50 ng/mL FGF-9 (preferably about 10 ng/mL)—astrocyte, oligodendrocyte, GABAergic and dopaminergic neurons
- 5-50 ng/mL FGF-8 (preferably about 10 ng/mL)—dopaminergic, serotoninergic and GABAergic neurons, no glial cells
- 5-50 ng/mL FGF-10 (preferably about 10 ng/mL)—astrocytes, oligodendrocytes, not neurons
- 5-50 ng/mL FGF-4 (preferably about 10 ng/mL)—astrocytes, oligodendrocytes but not neurons
- 5-50 ng/mL BDNF (preferably about 10 ng/mL)—Dopaminergic neurons only)
- 5-50 ng/mL GDNF (preferably about 10 ng/mL)—GABAergic and dopaminergic neurons
- 5-50 ng/mL CNTF (preferably about 10 ng/mL)—GABAergic neurons only The choice of growth factors to induce differentiation of MASCs into neural cells was based on what is known in embryonic development of the nervous system or from studies that evaluated in vitro NSC differentiation. All culture medium was serum-free and supplemented with EGF, which is a strong ectodermal inducer. FGFs play a key role in neuronal development. When human post-natal marrow derived MASCs were cultured with both 100 ng/mL bFGF and 10 ng/mL EGF, differentiation to astrocytes, oligodendrocytes and neurons was seen. Astrocytes were identified as glial-fibrilar-acidic-protein (GFAP) positive cells, oligodendrocytes were identified as glucocerebroside positive (GalC) and neurons were identified as cells that express in a sequential fashion NeuroD, Tubulin-IIIB (Tuji), synaptophysin and neurofilament 68, 160 and 200. Cells did not express markers of GAGAergic, dopaminergic or serotoninergic neurons.

FGF-9, first isolated from a glioblastoma cell line, induces proliferation of glial cells in culture. FGF-9 is found in vivo in neurons of the cerebral cortex, hippocampus, substantia nigra, motor nuclei of the brainstem and Purkinje cell layer. When cultured for 3 weeks with 10 ng/mL FGF-9 and EGF MASCs generated astrocytes, oligodendrocytes and GABAergic and dopaminergic. During CNS development, FGF-8, expressed at the mid/hindbrain boundary and by the rostral forebrain, in combination with Sonic hedgehog, induces differentiation of dopaminergic neurons in midbrain and forebrain. It was found that when MASCs were cultured with 10 ng/mL FGF-8 and EGF for 3 weeks both dopaminergic and GABAergic neurons were produced. FGF-10 is found in the brain in very low amounts and its expression is restricted to the hippocampus, thalamus, midbrain and brainstem where it is preferentially expressed in neurons but not in glial cells. Culture of MASCs in 10 ng/mL FGF-10 and EGF for three weeks generated astrocytes and oligodendrocytes, but not neurons. FGF-4 is expressed by the notochord and is required for the regionalisation of the midbrain. When treated with 10 ng/mL FGF-4 and EGF for 3 weeks MASCs differentiated into astrocytes and oligodendrocytes but not neurons.

Other growth factors that are specifically expressed in the brain and that affect neural development in-vivo and in-vitro include brain derived neurotrophic factor (BDNF), glial derived neurotrophic factor (GDNF) and ciliary neurotrophic factor (CNTF). BDNF is a member of the nerve growth factor family that promotes in vitro differentiation of NSC, human subependymal cells, and neuronal precursors to neurons and promotes neurite outgrowth of hippocamal stem cells in vivo. Consistent with the known function of BDNF to support survival of dopaminergic neurons of the substantia nigra, when MASCs were treated with 10 ng/mL BDNF and EGF exclusive differentiation into tyrosine hydroxylase positive neurons was seen. GDNF is a member of the TGF– superfamily. In early neurogenesis, GDNF is expressed in the anterior neuroectoderm suggesting that it may play a key role in neuronal development. GDNF promotes survival of motor neurons in peripheral nerve and muscle and has neurotrophic and differentiation abilities. It was found that GDNF induced MASCs to differentiate into GABAergic and dopaminergic neurons. CNTF, first isolated from ciliary ganglion, is a member of the gp130 family of cytokines. CNTF promotes neuronal survival early in development. In embryonic rat hippocampal cultures CNTF increased the numbers of GABAergic and cholinergic neurons. In addition, it prevented cell death of GABAergic neurons and promoted GABA uptake. CNTF exerted the same GABAergic induction on MASCs as they differentiated exclusively into GABAergic neurons after three weeks of exposure to CNTF.

Some hematopoietic cytokines have been shown to be trophic factors of NSC, such as IL-11 and LIF, as mentioned above. In addition, in vitro studies on neuronal precursor cells have shown that SCF, Flt3L, EPO, TPO, G-CSF, and CSF-1 act early in the differentiation of neural cells whereas IL5, IL7, IL9, and IL11 act later in neuronal maturation. MASCs induced with a combination of early acting cytokines (10 ng/mL Thrombopoietin (kind gift from Amgen Inc., Thousand Oaks, Calif.), 10 ng/mL granulocyte colony stimulating factor (Amgen), 3 U erythropoietin (Amgen) and 10 ng/mL interleukin-3 (R&D Systems), followed by culture for 1 month in a medium conditioned by the murine fetal liver feeder layer, AFT024 (a kind gift from Dr. Ihor Lemishka, Princeton University, NJ) supplemented with 14 ng/mL fetal liver tyrosine kinase-3 ligand (a kind gift from Immunex Inc, Seattle, Wash.) and 15 ng/mL SCF (a kind gift from Amgen) differentiated into astrocytes, oligodendrocytes and neurons. Neurons generated under these conditions were immature as they expressed neurofilament 68 but not 200.

In some cultures, MASCs had been retrovirally transduced with an eGFP containing vector (described in Example 4 above). Differentiated glial and neuronal cells continued to express eGFP. This indicates that these cells can be genetically modified without interfering with their differentiation. Thus, undifferentiated MASCs can generate a neural stem cell that then gives rise to astrocytes, oligodendrocytes and neurons.

The ease with which MASCs can be isolated from post-natal marrow, ex vivo expanded and induced to differentiate in vitro to glial cells or specific neuronal cell types circumvents one of the key problems in NSC transplantation, namely the availability of suitable donor tissue.

The cells of the present invention can be used in cell replacement therapy and/or gene therapy to treat or alleviate symptoms of congenital neurodegenerative disorders or storage disorders such as, for instance, mucopolysaccharidosis, leukodystrophies (globoid-cell leukodystrophy, Canavan disease), fucosidosis, GM2 gangliosidosis, Niemann-Pick, Sanfilippo syndrome, Wolman disease, and Tay Sacks. They can also be used to treat or alleviate symptoms of acquired neurodegenerative disorders such as Huntingtons, Parkinsons, Multiple Sclerosis, and Alzheimers. They can also be used for traumatic disorders such as stroke, CNS bleeding, and CNS trauma; for peripheral nervous system disorders such as spinal cord injury or syringomyelia; for retinal disorders such as retinal detachment, macular degeneration and other degenerative retinal disorders, and diabetic retinopathy.

Example 6

Hematopoietic Development

Hematopoietic Stem Cells (HSC) are mesodermal in origin. It was long thought that HSC originate from yolk sac mesoderm. There is ample evidence that primitive erythroid cells originate in the yolk sac. It is less clear whether definitive hemopoiesis also originates from cells in the yolk sac. A series of recent studies in chick embryos, murine and human embryos have suggested that definitive hemopoiesis may be derived from mesodermal cells present in the embryo proper, namely in the AGM region. In humans, between day 22 and 35, a small population of Flk1$^+$ cells develops in the dorsal aorta that differentiates into CD34$^+$ endothelial or hemopoietic cells. It is believed that these are the cells that colonize the fetal liver. Although cells with hemopoietic potential originate in the dorsal aorta, their differentiation and commitment to mature hemopoietic cells requires that they migrate to the liver where the endodermal environment is conducive for hemopoietic development. In contrast, cells that remain in the AGM region will not develop into hemopoietic cells.

Some of the clones in the present MASC cultures have hemopoietic potential. MASC differentiate into endothelial cells and form what resembles embryoid bodies. These same cell aggregates differentiate into hemopoietic cells. The small, suspended aggregates were trypsinized, and replated on FN, collagen type IV or ECM. Medium consisted either of 0.5-1000 ng/mL PDGF-BB (preferably about 10 ng/mL) and 0.5-1000 ng/mL EGF (preferably about 10 ng/mL) containing MASC medium supplemented with 5-1000 ng/mL SCF (preferably about 20 ng/mL) or a combination of IL3, G-CSF, Flt3-L and SCF (2-1000 ng/mL, preferably about 10-20 ng/mL). Alternatively 0.5-1000 ng/mL PDGF-BB (preferably about 10 ng/mL) and 0.5-1000 ng/mL EGF (preferably about 10 ng/mL) containing MASC medium was used with 5% FCS and 1-1000 ng/mL SCF (preferably about 100 ng/mL) that was conditioned by AFT024 cells. Cells recovered from either of these cultures expressed cKit, cMyb, Gata2 and G-CSF-R (RT-PCR/immunohistochemistry) indicating that hemopoietic differentiation is achievable.

Example 7

Epithelial Development

Applicants have also been able to demonstrate epithelial development. Briefly, a vessel was coated with 1-100 ng/mL fibronectin along with other ECM products such as 1-100 ng/mL laminin, collagens or IV and matrigel. The medium used comprised the following: 10-95% DMEM-LG, 5-90% MCDB-201, 1× ITS, 1× LA-BSA, $10^{-7}$-$10^{-9}$ M Dexamethasone (preferably $10^{-8}$), $10^{-3}$ to $10^{-5}$ M ascorbic acid 2-phosphate (preferably $10^{-4}$). The medium may also contain one or more of the following cytokines 0.5-100 ng/mL EGF (preferably about 10 ng/mL)
    0.5-1000 ng/mL PDGF-BB (preferably about 10 ng/mL)
    0.5-1000 ng/mL HGF (hepatocyte growth factor) (preferably about 10 ng/mL)
    0.5-1000 ng/nL KGF (keratinocyte growth factor) (preferably about 10 ng/mL)

Some of the cells were pancytokeratin positive, and cytokeratin 18 and 19 positive, which would suggest that these cells are endodermal in origin (i.e., hepatic epithelium, biliary epithelium, pancreatic acinary cells, or gut epithelium). Some of the cells demonstrated the presence of H-Met, or the hepatocyte growth factor receptor, which are specific for hepatic epithelium and renal epithelium. Other cells demonstrated the presence of keratin, which is compatible with skin epithelium.

The cells of the present invention can be used in cell replacement therapy and/or gene therapy to treat or alleviate symptoms of several organ diseases. The cells could be used to treat or alleviate congenital liver disorders, for example, storage disorders such as mucopolysaccharidosis, leukodystrophies, GM2 gangliosidosis; increased bilirubin disorders, for instance Crigler-Najjar syndrome; ammonia disorders such as inborn errors of the urea-cycle, for instance Ornithine decarboxylase deficiency, citrullinemia, and argininosuccinic aciduria; inborn errors of amino acids and organic acids such as phenylketoinuria, hereditary tyrosinemia, and Alpha1-antitrypsin deficiency; and coagulation disorders such as factor VIII and IX deficiency. The cells can also be used to treat acquired liver disorders due to viral infections. The cells of the present invention can also be used in ex vivo applications such as to generate an artificial liver (akin to kidney dialysis), to produce coagulation factors and to produce proteins or enzymes generated by liver epithelium.

The cells of the present invention can also be used to in cell replacement therapy and/or gene therapy to treat or alleviate symptoms of biliary disorders such as biliary cirthosis and biliary atresia.

The cells of the present invention can also be used to in cell replacement therapy and/or gene therapy to treat or alleviate symptoms of pancreas disorders such as pancreatic atresia, pancreas inflammation, and Alpha1-antitrypsin deficiency. Further, as pancreas epithelium can be made from the cells of the present invention, and as neural cells can be made, beta-cells can be generated. These cells can be used for the therapy of diabetes (subcutaneous implantation or intra-pancreas or intra-liver implantation.

Further, the cells of the present invention can also be used to in cell replacement therapy and/or gene therapy to treat or alleviate symptoms of gut epithelium disorders such as gut atresia, inflammatory bowel disorders, bowel infarcts, and bowel resection.

Moreover, the cells of the present invention can also be used to in cell replacement therapy and/or gene therapy to treat or alleviate symptoms of skin disorders such as alopecia, skin defects such as burn wounds, and albinism.

Example 8

Expressed Gene Profile of MASCS, Cartilage and Bone

Using Clontech and Invitrogen cDNA arrays the inventors evaluated the expressed gene profile of human MASCs cultured at seeding densities of $2 \times 10^3/cm^2$ for 22 and 26 cell doublings. In addition the inventors evaluated changes in gene expression when MASCs were induced to differentiate to cartilage and bone for 2 days.

MASCs do not express CD31, CD36, CD62E, CD62P, CD44-H, cKit, Tie, receptors for IL1, IL3, IL6, IL11, G-CSF, GM-CSF, Epo, Flt3-L, or CNTF, and low levels of HLA-class-I, CD44-E and Muc-18 mRNA.

MASCs express mRNA for the cytokines BMP1, BMP5, VEGF, HGF, KGF, MCP1; the cytokine receptors Flk1, EGF-R, PDGF-R1α, gp130, LIF-R, activin-R1 and -R2, TGFR-2, BMP-R1A; the adhesion receptors CD49c, CD49d, CD29; and CD10.

MASCs express mRNA for hTRT, oct-4, sox-2, sox-11, sox-9, hoxa4, -5, -9, Dlx4, MSX1, PDX1

Both cartilage and bone lost/had decreased expression oct-4, sox-2, Hoxa4, 5, 9; Dlx4, PDX1, hTRT, TRF1, cyclins, cdk's, syndecan-4; dystroglycan integrin α2, α3, β1, FLK1, LIF-R, RAR-α, RARγ, EGF-R, PDGF-R1a and -B, TGF-R1 and -2, BMP-R1A, BMP1 and 4, HGF, KGF, MCP1

Osteoblast differentiation was associated with acquisition of/increase in expression of Hox7, hox11, sox22, cdki's, syndecan-4, decorin, lumican, fibronectin, bone sialoprotein, TIMP-1, CD44, β8, β5 integrin, PTHr-P, Leptin-R, VitD3-R, FGF-R3, FGF-R2, Estrogen-R, wnt-7a, VEGF-C, BMP2

Cartilage differentiation was associated with acquisition of Sox-9, FREAC, hox-11, hox7, CART1, Notch3, cdki's, collagen-II, fibronectin, decorin, cartilage glycoprotein, cartilage oligomeric matrix protein, MMPs and TIMPs, N-cadherin, CD44, α1 and α6 integrin, VitD3-R, BMP2, BMP7

Example 9

Characterization of Differentially Expressed Genes in MASCs vs. Osteoblasts by Subtractive Hybridization The present inventors used a subtraction approach to identify genetic differences between undifferentiated MASCs and committed progeny. Poly-A mRNA was extracted from undifferentiated MASCs and cells induced to differentiate to the osteoblast lineage for 2 days. Subtraction and amplification of the differentially expressed cDNAs was done using the PCR-Select kit from Clonetech, as per manufacturer's recommendation without modification. Gene sequences expressed in day 2 osteoblast cultures were analyzed, but not those in undifferentiated MASCs.

Eighty-six differentially expressed cDNA-sequences were sequenced. It was confirmed by Northern that the mRNAs were indeed specifically expressed in day 2 osteoblast progenitors and not MASCs. The sequences were compared (using the BLAST algorithm) to the following databases: SwissProt, GenBank protein and nucleotide collections, ESTs, murine and human EST contigs.

Sequences were categorized by homology: 8 are transcription factors, 20 are involved in cell metabolism; 5 in chromatin repair; 4 in the apoptosis pathway; 8 in mitochondrial function; 14 are adhesion receptors/ECM components; 19 are published EST sequences with unknown function and 8 are novel.

For 2 of the novel sequences, Q-RT-PCR was performed on MASCs induced to differentiate to bone for 12 h, 24 h, 2 d, 4 d, 7 d and 14 d from 3 individual donors. Genes are expressed during the initial 2 and 4 days of differentiation respectively, and down regulated afterwards.

Genes present in undifferentiated MASCs, but not day 2 osteoblasts, were also analyzed. Thirty differentially expressed genes have been sequenced and 5 of them are EST sequences or unknown sequences. Presence of these genes in MASCs but not day 2 osteoblasts is confirmed by Northern blot.

Example 10

MASC Engraftment

Studies were initiated to examine if MASCs engraft and persist in vivo.

eGFP+ MASCS were injected intramuscularly into NOD-SCID mice. Animals were sacrificed 4 weeks later and muscle examined to determine if, as has been described for human ES cells, teratomas develop. In 5/5 animals, no teratomas were seen. eGFP positive cells were detected. Also, eGFP+ MASCS IV were infused intrauterine in fetal SCID mice. Animals were evaluated immediately after birth. PCR analysis demonstrated presence of eGFP+ cells in heart, lung, liver, spleen and marrow.

When MASCs are transplanted stereotaxically in the intact brain or infarcted brain of rats, they acquire a phenotype compatible with neural cells, and persist for at least 6 weeks. These studies show that human MASCs can engraft in vivo and differentiate in an organ specific fashion without developing into teratomas.

The studies also show that MASCs are distinctly different than embryonic stem cells or germ cells. MASCs represent a new class of multipotent stem cells that can be derived from multiple organs of adults and children.

Example 11

Demonstration of the Ability to Select, Expand and Characterize MASCs from Murine Origin MASCs can be generated from mouse marrow and can be present in organs other than marrow.
1. Identification of MASCs in Mouse Marrow The investigators selected MASCs from mouse marrow. Marrow from C57/BL6 mice was obtained and mononuclear cells or cells depleted of CD45 and GlyA positive cells (n=6) plated under the same culture conditions used for human MASCs (10 ng/mL human PDGF-BB and EGF). When marrow mononuclear cells were plated, we depleted CD45$^+$ cells 14 days after initiation of culture to remove hemopoietic cells. As for human MASCs, cultures were re-seeded at 2,000 cells/cm$^2$ every 2 cell doublings.

In contrast to what we saw with human cells, when fresh murine marrow mononuclear cells depleted on day 0 of CD45$^+$ cells were plated in MASCs culture, no growth was seen. When murine marrow mononuclear cells were plated, and cultured cells 14 days later depleted of CD45$^+$ cells, cells with the morphology and phenotype similar to that of human MASCs appeared. This suggests that factors secreted by hemopoietic cells may be needed to support initial growth of murine MASCs. When cultured with PDGF-BB and EFG alone, cell doubling was slow (>6 days) and cultures could not be maintained beyond 10 cell doublings. Addition of 10 ng/mL LIF improved cell growth and >70 cell doublings have been obtained. When cultured on laminin, collagen type IV or matrigel, cell growth was seen, but cells were CD44+ and HLA-class-I positive. As for human cells, C57/BL6 MASCs cultured with LIF on fibronectin coated dishes are CD44 and HLA-class-I negative, stain positive with SSEA-4, and express transcripts for oct-4, LIF-R and sox-2.

MASCS derived from mouse marrow can be induced to differentiate into cardiac muscle cells, endothelium and neuroectodermal cells using methods also used to induce differentiation of human MASCs. Therefore, C57B16 mouse marrow derived MASCs are equivalent to those obtained from human marrow.
2. MASCs are Present in Tissues Other than Marrow The inventors examined if MASCs are present in other organs such as liver and brain. Marrow, brain or liver mononuclear cells from 5-day old FVB/N mice, dissociated with collagenase and trypsin were plated in MASC cultures with EGF, PDGF-BB and LIF on fibronectin. 14 days later, CD45$^+$ cells were removed and cells maintained in MASCs culture conditions as described above. Cells with morphology similar to that of human MASC and murine MASC derived from marrow of C57/B16 mice grew in cultures initiated with marrow, brain or liver cells. Cells expressed oct-4 mRNA.

The inventors also examined mice transgenic for an oct-4 promoter-eGFP gene. In these animals, eGFP expression is seen in primordial germ cells as well as in germ cells after birth. As MASCs express oct-4, we tested whether eGFP positive cells could be found in marrow, brain, and liver of these animals after birth. We sorted eGFP$^+$ cells (1% brightest population) from marrow, brain and liver from 5 day-old mice. When evaluated by fluorescence microscopy, <1% of sorted cells from brain and marrow were eGFP$^+$. oct-4 mRNA could be detected by Q-RT-PCR in the sorted population. Sorted cells have been plated under conditions that support murine MASCs (fibronectin coated wells with EGF, PDGF, LIF). Cells survived but did not expand. When transferred to murine embryonic fibroblasts, cell growth was seen. When subsequently transferred to MASC cultures, cells with morphology and phenotype similar to that of MASC derived using classical MASC selection and culture methods from human marrow or marrow of C57/B16 or FVB/N mice were obtained.

The invention is described with reference to various specific and preferred embodiments and techniques. However, it should be understood that many variations and modifications may be made while remaining within its scope. All referenced publications, patents and patent documents are intended to be incorporated by reference, as though individually incorporated by reference.

REFERENCES

1. Thomson J, Kalishman J, Golos T, Durning M, Harris C, Becker R, Hearn J: Isolation of a primate embryonic stem cell line. Proc Natl Acad Sci USA 92:7844-8, 1995
2. Thomson J A, Itskovitz-Eldor J, Shapiro S S, Waknitz M A, Swiergiel J J, Marshall V S, Jones J M: Embryonic stem cell lines derived from human blastocysts. Science 282:114-114, 1998
3. Shamblott M, Axelman J, Wang S, Bugg E, Littlefield J, Donovan P, Blumenthal P, Huggins G, Gearhart J: Derivation of pluripotent stem cells from cultured human primordial germ cells. Proc Natl Acad Sci USA 95:13726-31, 1998
4. Williams R L, Hilton D J, Pease S, Willson T A, Stewart C L, Gearing D P, Wagner E F, Metcalf D, Nicola N A, Gough N M: Myeloid leukaemia inhibitory factor maintains the developmental potential of embryonic stem cells. Nature 336:684-7, 1988
5. Orkin S: Embryonic stem cells and transgenic mice in the study of hematopoiesis. Int J Dev Biol 42:927-34, 1998
6. Weissman I L: Translating stem and progenitor cell biology to the clinic: barriers and opportunities. Science 287:1442-6, 2000
7. Gage F H: Mammalian Neural Stem Cells. Science 287:1433-1438, 2000
8. Svendsen C N, Caldwell M A, Ostenfeld T: Human neural stem cells: Isolation, expansion and transplantation. Brain Path 9:499-513, 1999
9. Okabe S, Forsberg-Nilsson K, Spiro A C, Segal M, McKay R D: Development of neuronal precursor cells and functional postmitotic neurons from embryonic stem cells in vitro. Mech Dev 59:89-102, 1996
10. Potten C: Stem cells in gastrointestinal epithelium: numbers, characteristics and death. Philos Trans R Soc Lond B Biol Sci 353:821-30, 1998
11. Watt F: Epidermal stem cells: markers patterning and the control of stem cell fate. Philos Trans R Soc Lond B Biol Sci 353:831, 1997
12. Alison M, Sarraf C: Hepatic stem cells. J Hepatol 29:678-83, 1998
13. Haynesworth S E, Barber M A, Caplan I A: Cell surface antigens on human marrow-derived mesenchymal cells are detected by monoclonal antibodies. Bone 13:69-80, 1992

14. Pittenger M F, Mackay A M, Beck S C, Jaiswal R K, Douglas R, Mosca J D, Moorman M A, Simonetti D W, Craig S, Marshak D R: Multilineage potential of adult human mesenchymal stem cells. Science 284:143-147, 1999
15. Gronthos S, Zannettino A C, Graves S, Ohta S, Hay S J, Simmon P J: Differential cell surface expression of the STRO-1 and alkaline phosphatase antigens on discrete developmental stages in primary cultures of human bone cells. J Bone Miner Res 14:47-56, 1999
16. Prockop D: Marrow stromal cells as stem cells for nonhematopoietic tissues. Science 276:71-4, 1997
17. Jackson K, Mi T, Goodell M A: Hematopoietic potential of stem cells isolated from murine skeletal muscle. Proc Natl Acad Sci USA 96:14482-6, 1999
18. Ferrari G, Cusella-De Angelis G, Coletta M, Paolucci E, Stornaiuolo A, Cossu G, Mavilio F: Muscle regeneration by bone marrow-derived myogenic progenitors. Science 279:528-30, 1998
19. Gussoni E, Soneoka Y, Strickland C, Buzney E, Khan M, Flint A, Kunkel L, Mulligan R: Dystrophin expression in the mdx mouse restored by stem cell transplantation. Nature 401:390-4, 1999
20. Asahara T, Masuda H, Takahashi T, Kalka C, Pastore C, Silver M, Kearne M, Magner M, Isner J M: Bone marrow origin of endothelial progenitor cells responsible for postnatal vasculogenesis in physiological and pathological neovascularization. Circ Res 85:221-8, 1999
21. Lin Y, Weisdorf D J, Solovey A, Hebbel R P: Origins of circulating endothelial cells and endothelial outgrowth from blood. J Clin Invest 105:71-7, 2000
22. Petersen B E, Bowen W C, Patrene K D, Mars W M, Sullivan A K, Murase N, Boggs S S, Greenberger J S, Goff J P: Bone marrow as a potential source of hepatic oval cells. Science 284:1168-1170, 1999
23. Theise N D, Badve S, Saxena R, Henegariu O, Sell S, Crawford J M, Krause D S: Derivation of hepatocytes from bone marrow cells in mice after radiation-induced myeloablation. Hepatology 31:235-40, 2000
24. Theise N D, Nimmakayalu M, Gardner R, Illei P B, Morgan G, Teperman L, Henegariu O, Krause D S: Liver from bone marrow in humans. Hepatology 32:11-6, 2000
25. Frankel M S: In Search of Stem Cell Policy. Science 298:1397, 2000
26. Greider C: Telomeres and senescence: the history, the experiment, the future. Curr Biol 8:178-81, 1998
27. Reubinoff B E, Pera M F, Fong C Y, Trounson A, Bongso A: Embryonic stem cell lines from human blastocysts: somatic differentiation in vitro. Nat Biotech 18:399-404, 2000
28. Nichols J, Zevnik B, Anastassiadis K, Niwa H, Klewe-Nebenius D, Chambers I, Scholer H, Smith A: Formation of pluripotent stem cells in the mammalian embryo depends on the POU transcription factor Oct4. Cell 95:379-91, 1998
29. Rosfjord E, Rizzino A: The octamer motif present in the Rex-1 promoter binds Oct-1 and Oct-3 expressed by EC cells and ES cells. Biochem Biophys Res Commun 203:1795-802, 1997
30. Ben-Shushan E, Thompson J R, Gudas L J, Bergman Y: Rex-1, a gene encoding a transcription factor expressed in the early embryo, is regulated via Oct-3/4 and Oct-6 binding to an octamer site and a novel protein, Rox-1, binding to an adjacent site. Mol Cell Biol 18:1866-78, 1998
31. Uwanogho D, Rex M, Cartwright E J, Pearl G, Healy C, Scotting P J, Sharpe P T: Embryonic expression of the chicken Sox2, Sox3 and Sox11 genes suggests an interactive role in neuronal development. Mech Dev 49:23-36, 1995
32. Baum C, Weissman I, Tsukamoto A, Buckle A, Peault B: Isolation of a candidate human hematopoietic stem cell population. Proc Natl Acad Sci USA 89:2804, 1992
33. Jordan C, McKearn J, Lemischka I: Cellular and developmental properties of fetal hematopoietic stem cells. Cell 61:953-963, 1990
34. Bhatia M, Wang J, Knapp U, Bonnet D, Dick J: Purification of primitive human hematopoietic cells capable of repopulating immune-deficient mice. Proc Natl Acad Sci USA 94:5320, 1997
35. Goodell M, Rosenzweig M, Kim H, Marks D, DeMaria M, Paradis G, Grupp S, Sieff C, Mulligan R, Johnson R: Dye efflux studies suggest that hematopoietic stem cells expressing low or undetectable levels of 34 antigen exist in multiple species. Nature Medicine 3:1337-1345, 1997
36. Zijlmans J M, Visser J W, Kleiverda K, Kluin P M, Willemze R, Fibbe W E: Modification of rhodamine staining allows identification of hematopoietic stem cells with preferential short-term or long-term bone marrow-repopulating ability. Proc Natl Acad Sci USA 92:8901-8905, 1995
37. Phillips R L, Ernst R E, Brunk B, Ivanova N, Mahan M A, Deanehan J K, Moore K A, Overton G C, Lemischka I R: The genetic program of hematopoietic stem cells. Science 288:1635-40, 2000
38. Martin G R: Isolation of a pluripotent cell line from early mouse embryos cultured in medium conditioned by teratocarcinoma stem cells. Proc Natl Acad Sci USA 78:7634-8, 1981
39. Wobus A M, Holzhausen H, Jakel P, Schoneich J: Characterization of a pluripotent stem cell line derived from a mouse embryo. Exp Cell Res 52:212-9, 1984
40. Kannagi R, Cochran N A, Ishigami F, Hakomori S, Andrews P W, Knowles B B, Solter D: Stage-specific embryonic antigens (SSEA-3 and -4) are epitopes of a unique globo-series ganglioside isolated from human teratocarcinoma cells. EMBO J 2:2355-61, 1983
41. Scholer H R, Hatzopoulos A K, Balling R, Suzuki N, Gruss P: A family of octamer-specific proteins present during mouse embryogenesis: evidence for germline-specific expression of an Oct factor. EMBO J 8:2543-50, 1989
42. Yuan H, Corbi N, Basilico C, Dailey L: Developmental-specific activity of the FGF-4 enhancer requires the synergistic action of Sox2 and Oct-3. Genes Dev 9:2635-45, 1995
43. Rosner M H, Vigano M A, Ozato K, Timmons P M, Poirier F, Rigby P W, Staudt L M: A POU-domain transcription factor in early stem cells and germ cells of the mammalian embryo. Nature 345:686-92, 1990
44. Pikarsky E, Sharir H, Ben-Shushan E, Bergman Y: Retinoic acid represses Oct-3/4 gene expression through several retinoic acid-responsive elements located in the promoter-enhancer region. Mol Cell Biol 14:1026-38, 1994
45. Niwa H, Miyazaki J, Smith A G: Quantitative expression of Oct-3/4 defines differentiation, dedifferentiation or self-renewal of ES cells. Nat Genet 24:372-6, 2000
46. Cooke J E, Godin I, Ffrench-Constant C, Heasman J, Wylie C C: Culture and manipulation of primordial germ cells. Methods Enzymol 255:37-58, 1993

47. Hodes R J: Telomere length, aging, and somatic cell turnover. J Exper Med 190:153-156, 1999
48. Choi K, Kennedy M, Kazarov A, Papadimitriou J C, Keller G: A common precursor for hematopoietic and endothelial cells. Development 125:725-732, 1998
49. Medvinsky A, Dzierzak E: Definitive hematopoiesis is autonomously initiated by the AGM region. Cell 86:897, 1996
50. Yoder M, Hiatt K, Mukherjee P: In vivo repopulating hematopoietic stem cells are present in the murine yolk sac at day 9.0 postcoitus. Proc. Natl. Acad. Sci. USA 94:6776, 1997
51. Spangrude G, Heimfeld S, Weissman I: Purification and characterization of mouse hematopoietic stem cells. Science 241:58, 1988
52. Tricot G, Gazitt Y, Leemhuis T, Jagannath S, Desikan K R, Siegel D, Fassas A, Tindle S, Nelson J, Juttner C, Tsukamoto A, Hallagan J, Atkinson K, Reading C, Hoffman R, Barlogie B: Collection, tumor contamination, and engraftment kinetics of highly purified hematopoietic progenitor cells to support high dose therapy in multiple myeloma. Blood 91:4489-95, 1998
53. Gothot A, Pyatt R, McMahel J, Rice S, Srour E F: Functional heterogeneity of human CD34(+) cells isolated in subcompartments of the G0/G1 phase of the cell cycle. Blood 90:4384-4393, 1997
54. Goodell M, Brose K, Paradis G, Conner A, Mulligan R: Isolation and functional properties of murine hematopoietic stem cells that are replicating in vivo. J Exp Med 183:1797-1806, 1996
55. McCune J M, Namikawa R, Kaneshima H, Shultz L D, Lieberman M, Weissman I L: The SCID-hu mouse: murine model for the analysis of human hematolymphoid differentiation and function. Science 24:1632-1639, 1988
56. Moore K A, Hideo E, Lemischka I R: In vitro maintenance of highly purified transplantable hematopoietic stem cells. Blood 89:4337-437, 1997
57. Fraser C, Szilvassy S, Eaves C, Humphries R: Proliferation of totipotent hematopoietic stem cells culture at limiting dilution on supportive marrow stroma. Proc Natl Acad Sci USA 89:1968-1972, 1992
58. McKay R: Stem cells in the central nervous system. Science 276:66-71, 1997
59. Huard J M, Youngentob S L, Goldstein B J, Luskin M B, Schwob J E: Adult olfactory epithelium contains multipotent progenitors that give rise to neurons and non-neuronal cells. J Comp Neurol 400:469-486, 1998
60. Palmer T D, Takahashi J, Gage F H: The adult rat hippocampus contains primordial neural stem cells. Mol Cell Neurosci 8:389-404, 1997
61. Lois C, Alvarez-Buylla A: Proliferating subventricular zone cells in the adult mammalian forebrain can differentiate into neurons and glia. Proc Natl Acad Sci USA 90:2074-7, 1993
62. Roy N S, Wang S, Jiang L, Kang J, Benraiss A, Harrison-Restelli C, Fraser R A, Couldwell W T, Kawaguchi A, Okano H, Nedergaard M, Goldman S A: In vitro neurogenesis by progenitor cells isolated from the adult human hippocampus. Nat Med 5:271-7, 2000
63. Johansson C B, Momma S, Clarke D L, Risling M, Lendahl U, Frisen J: Identification of a neural stem cell in the adult mammalian central nervous system. 1998 96:25-34, 1999
64. Fridenshtein A: Stromal bone marrow cells and the hematopoietic microenvironment. Arkh Patol 44:3-11, 1982
65. Wakitani S, Saito T, Caplan A: Myogenic cells derived from rat bone marrow mesenchymal stem cells exposed to 5-azacytidine. Muscle Nerve 1417-26:18, 1995
66. Gronthos S, Graves S, Ohta S, Simmons P: The STRO-1+ fraction of adult human bone marrow contains the osteogenic precursors. Blood 84:4164-73, 1994
67. Colter D C, Class R, DiGirolamo C M, Prockop D J: Rapid expansion of recycling stem cells in cultures of plastic-adherent cells from human bone marrow. roc Natl Acad Sci USA 97:3213-8, 2000
68. Yui J, Chiu C, Lansdorp P: Telomerase activity in candidate stem cells from fetal liver and adult bone marrow. Blood 91:91(9):3255-62, 1998
69. Bjornson C, Rietze R, Reynolds B, Magli M, Vescovi A: Turning brain into blood: a hematopoietic fate adopted by adult neural stem cells in vivo. science 283:354-7, 1999
70. Almeida Porada G, Crapnell H, Porada C, Benoit H, Quesenberry P, Zanjani E D: In vivo hematopoietic potential of human neuronal stem cells. Exp Hematol 28, Supplement 1:61 (abstract), 2000
71. Clarke D L, Johansson C B, Wilbertz J, Veress B, Nilsson E, Karlstrom H, Lendahl U, Frisen J: Generalized potential of adult neural stem cells. Science 288:1660-3, 2000
72. Rideout W M, 3rd, Wakayama T, Wutz A, Eggan K, Jackson-Grusby L, Dausman J, Yanagimachi R, Jaenisch R: Generation of mice from wild-type and targeted ES cells by nuclear cloning. Nat Genet 24:109-10, 2000
73. Wilmut I, Schnieke A E, McWhir J, Kind A J, Campbell K H: Viable offspring derived from fetal and adult mammalian cells. Nature 385:810-3, 1997
74. Tsonis P A: Regeneration in vertebrates. Dev Biol 221:273-84, 2000
75. Lemischka I: The power of stem cells reconsidered? Proc Natl Acad Sci USA 96:1493-5, 1999
76. Anderson R, Fassler R, Georges-Labouesse E, Hynes R O, Bader B L, Kreidberg J A, Schaible K, Heasman J, Wylie C: Mouse primordial germ cells lacking beta1 integrins enter the germline but fail to migrate normally to the gonads. Development 126:1655-64, 1999
77. Keller G, Snodgrass H R: Human embryonic stem cells: the future is now. Nat Med 5:151-152, 1999
78. Lefebvre V, de Crombrugghe B: Toward understanding SOX9 function in chondrocyte differentiation. Matrix Biol 16:529-40, 1998
79. Yoshida K, Chambers I, Nichols J, Smith A, Saito M, Yasukawa K, Shoyab M, Taga T, Kishimoto T: Maintenance of the pluripotential phenotype of embryonic stem cells through direct activation of gp130 signalling pathways. Mech Dev 45:163-71, 1994
80. Ma Y G, Rosfjord E, Huebert C, Wilder P, Tiesman J, Kelly D, Rizzino A: Transcriptional regulation of the murine k-FGF gene in embryonic cell lines. Dev Biol 154:45-54, 1992
81. Anderson R, Copeland T K, Scholer H, Heasman J, Wylie C: The onset of germ cell migration in the mouse embryo. Mech Dev 91:61-8, 2000
82. Gerstenfeld L C, Shapiro F D: Expression of bone-specific genes by hypertrophic chondrocytes: implication of the complex functions of the hypertrophic chondrocyte during endochondral bone development. J Cell Biohem 62:1-9, 1996
83. Binette F, McQuaid D P, Haudenschild D R, Yaeger P C, McPherson J M, Tubo R: Expression of a stable 83. articular cartilage phenotype without evidence of hypertrophy by adult human articular chondrocytes in vitro. J Orthop Res 16:207-16, 1998
84. Cai R L: Human CART1, a paired-class homeodomain protein, activates transcription through palindromic binding sites. Biochem Biophys Res Commun 250:305-11, 1998
85. Dietz U H, Sandell L J: Cloning of a retinoic acid-sensitive mRNA expressed in cartilage and during chondrogenesis. J Biol Chem 271:3311-6, 1996
86. Konieczny S F, Emerson C P Jr: Differentiation, not determination, regulates muscle gene activation: transfection of troponin I genes into multipotential and muscle lineages of 10T1/2 cells. Mol Cell Biol 5:2423-32, 1985
87. Dinsmore J, Ratliff J, Deacon T, Pakzaban P, Jacoby D, Galpern W, Isacson O: Embryonic stem cells differentiated in vitro as a novel source of cells for transplantation. Cell Transplant 5:131-143, 1996
88. Chen J, Goldhamer D: Transcriptional mechanisms regulating MyoD expression in the mouse. Cell Tissue Res 296:213-9, 1999
89. Wasserman S: F H proteins as cytoskeletal organizers. Cell Biology 8:111-115, 1998
90. Mesnard L, Samson F, Espinasse I, Durand J, Neveux J Y, Mercadier J J: Molecular cloning and developmental expression of human cardiac troponin T. FEBS Lett 328:139-44, 1993
91. Doumit M E, Merkel R A: Conditions for isolation and culture of porcine myogenic satellite cells. Tissue Cell 24:253-62, 1992
92. Hirschi K K, Rohovsky S A, D'Amore P A: PDGF, TGF-beta, and heterotypic cell-cell interactions mediate endothelial cell-induced recruitment of 10T1/2 cells and their differentiation to a smooth muscle fate. J Cell Biol 141:805-14, 1998
93. Miano J, Cserjesi P, Ligon K, Periasamy M, Olson E: Smooth muscle myosin heavy chain exclusively marks the smooth muscle lineage during mouse embryogenesis. Circ Res 75:803-12, 1994
94. Wobus A M, Kaomei G, Shan J, Wellner M C, Rohwedel J, Ji G, Fleischmann B, Katus H A, Hescheler J, Franz W M: Retinoic acid accelerates embryonic stem cell-derived cardiac differentiation and enhances development of ventricular cardiomyocytes. J Mol Cell Cardiol 29:1525-39, 1998
95. Laverriere A C, MacNeill C, Mueller C, Poelmann R E, Burch J B, Evans T: GATA-4/5/6, a subfamily of three transcription factors transcribed in developing heart and gut. J Biol Chem 269:23177-84, 1994
96. Bhavsar P K, Dhoot G K, Cumming D V, Butler-Browne G S, Yacoub M H, Barton P J: Developmental expression of troponin I isoforms in fetal human heart. FEBS Lett 292:5-8, 1991
97. Forssmann W, Richter R, Meyer M: The endocrine heart and natriuretic peptides: histochemistry, cell biology, and functional aspects of the renal urodilatin system. Histochem Cell Biol 110:335-57, 1998
98. Punzel M, Wissink S, Miller J, Moore K, Lemischka I, Verfaillie C: The myeloid-lymphoid initiating cell (ML-IC) assay assesses the fate of multipotent human progenitors in vitro. blood 93:3750-6, 1999
99. Thiemann F T, Moore K A, Smogorzewska E M, Lemischka I R, Crooks G M: The murine stromal cell line AFT024 acts specifically on human CD34+CD38− progenitors to maintain primitive function and immunophenotype in vitro. Exp Hematol 26:612-619, 1998
100. Rosenberg J B, Foster P A, Kaufman R J, Vokac E A, Moussalli M, Kroner P A, Montgomery R R: Intracellular trafficking of factor VIII to von Willebrand factor storage granules. J Clin Invest 101:613-24, 1998
101. Baumhueter S, Dybdal N, Kyle C, Lasky L: Global vascular expression of murine CD34 a sialomucin-like endothelial ligand for L-selectin. Blood 84:2554, 1994
102. Hamagushi I, Huang X L, Takakura N, Tada J, Yamagushi Y, Kodama H, Suda T: In vitro hematopoietic and endothelial cell development from cells expressing TEK receptor in murine aorta-gonad-mesonephros region. Blood 93:1549-1556, 1999
103. Shalaby F, Ho J, Stanford W, Fischer K, Schuh A, Schwartz L, Bernstein A, Rossant J: A requirement for Flk1 in primitive and definitive hematopoiesis and vasculogenesis. Cell 89:981-90, 1997
104. Newman P: The biology of PECAM-1. J Clin Invest 99:3, 1997
105. Tedder T, Steeber D, Chen A, Engel P: The selectins: vascular adhesion molecules. FASEB J 9:866, 1995
106. Nishikawa S, Nishikawa S, Hirashima M, Matsuyoshi N, Kodama H: Progressive lineage analysis by cell sorting and culture identifies FLK1+VE-cadherin+ cells at a diverging point of endothelial and hemopoietic lineages. Development 125:1747-57, 1998
107. Belaoussoff M, Farrington S M, Baron M H: Hematopoietic induction and respecification of A-P identity by visceral endoderm signaling in the mouse embryo. Development 125:5009-18, 1988
108. Weiss S, Dunne C, Hewson J, Wohl C, Wheatley M, Peterson A C, Reynolds B A: Multipotent CNS stem cells are present in the adult mammalian spinal cord and ventricular neuroaxis. J Neurosci 16:7599-609, 1996
109. Shihabuddin L S, Ray J, Gage F H: FGF-2 is sufficient to isolate progenitors found in the adult mammalian spinal cord. Exp Neurol 148:577-86, 1997
110. Ciccolini F, Svendsen C N: Fibroblast growth factor 2 (FGF-2) promotes acquisition of epidermal growth factor (EGF) responsiveness in mouse striatal precursor cells: Identification of neural precursors responding to both EGF and FGF-2. J Neuroscience 18(19):7869-7880, 1998
111. Julien J, Mushynski W: Neurofilaments in health and disease. Prog Nucleic Acid Res Mol Biol 61:1-23, 1998
112. Schaafsma H, Ramaekers F: Cytokeratin subtyping in normal and neoplastic epithelium: basic principles and diagnostic applications. Pathol Annu 29:21-62, 1994
113. Lazaro C A, Rhim J A, Yamada Y, Fausto N: Generation of hepatocytes from oval cell precursors in culture. Cancer Res 58:5514-22, 1998
114. Kiem H, Heyward P, Winkler A, Potter J, Allen J, Miller A, Andrew R: Gene transfer into marrow repopulating cells: comparison between amphotropic and gibbon ape leukemia virus pseudotyped retroviral vectors in a competitive repopulation assay in baboons. Blood 90:4638-45, 1997
115. Nolta J, Dao M, Wells S, Smogorzewska E, Kohn D: Transduction of pluripotent human hematopoietic stem cells demonstrated by clonal analysis after engraftment in immune-deficient mice. Proc Natl Acad Sci USA 93:2414-9, 1996
116. Huibregtse B A, Johnstone B, Goldberg V M, Caplan A I: Effect of age and sampling site on the chondro-osteogenic potential of rabbit marrow-derived mesenchymal progenitor cells. Orthop Res 18:18-24, 2000

117. Bandyopadhyay P, Ma X, Linehan-Stieers C, Kren B, Steer C: Nucleotide exchange in genomic DNA of rat hepatocytes using RNA/DNA oligonucleotides. Targeted delivery of liposomes and polyethyleneimine to the asialoglycoprotein receptor. J Biol Chem: 10163-72, 1999

118. Sielaff T D, Nyberg S L, Rollins M D, Hu M Y, Amiot B, Lee A, Wu F J, Hu W S, Cerra F B: Characterization of the three-compartment gel-entrapment porcine hepatocyte bioartificial liver. Cell Biol Toxicol 13:357-64, 1997

119. Peshwa M V, Wu F J, Sharp H L, Cerra F B, Hu W S: Mechanistics of formation and ultrastructural evaluation of hepatocyte spheroids. 32:197-203, 1996

120. Rogler L E: Selective bipotential differentiation of mouse embryonic hepatoblasts in vitro. Am J Pathol 150:591-602, 1997

121. Block G D, Locker J, Bowen W C, Petersen B E, Katyal S, Strom S C, Riley T, Howard T A, Michalopoulos G K: Population expansion, clonal growth, and specific differentiation patterns in primary cultures of hepatocytes induced by HGF/SF, EGF and TGF alpha in a chemically defined (HGM) medium. J Cell Biol 132:1133-49, 1996

122. Hao Q L, Thiemann F T, Petersen D, Smogorzewska E M, Crooks G M: Extended long-term culture reveals a highly quiescent and primitive human hematopoietic progenitor population. Blood 88:3306-3313, 1996

123. Visser J W, Bol S J, van den Engh G: Characterization and enrichment of murine hemopoietic stem cells by fluorescence activated cell sorting. Exp Hematol 9:644-55, 1981

124. Gothot A, van der Loo J C, Clapp D W, Srour E F: Cell cycle-related changes in repopulating capacity of human mobilized peripheral blood CD34(+) cells in non-obese diabetic/severe combined immune-deficient mice. Blood 92:2641-9, 1998

125. Klug M G, Soonpaa M H, Koh G Y, Field L J: Genetically selected cardiomyocytes from differentiating embryonic stem cells form stable intracardiac grafts. J Clin Invest 98:216-24, 1996

126. Kipriyanov S M, Little M: Generation of recombinant antibodies. Mol Biotechnol 12:173-201, 1999

127. Shinohara N, Demura T, Fukuda H: Isolation of a vascular cell wall-specific monoclonal antibody recognizing a cell polarity by using a phage display subtraction method. Proc Natl Acad Sci USA 97:2585-90, 2000

128. Iyer V R, Eisen M B, Ross D T, Schuler G, Moore T, Lee J C F, Trent J M, Staudt L M, Hudson J J, Boguski M S, Lashkari D, Shalon D, Botstein D, Brown P O: The transcriptional program in the response of human fibroblasts to serum. Science 283: 83-7, 1999

129. Scherf U, Ross D T, Waltham M, Smith L H, Lee J K, Tanabe L, Kohn K W, Reinhold W C, Myers T G, Andrews D T, Scudiero D A, Eisen M B, Sausville E A, Pommier Y, Botstein D, Brown P O, Weinstein J N: A gene expression database for the molecular pharmacology of cancer. Nat Biotech 24:236-44, 2000

130. Alizadeh A A, Eisen M B, Davis R E, Ma C, Lossos I S, Rosenwald A, Boldrick J C, Sabet H, Tran T, Yu X, Powell J I, Yang L, Marti G E, Moore T, Hudson J J, Lu L, Lewis D B, Tibshirani R, Sherlock G, Chan W C, Greiner T C, Weisenburger D D, Armitage J O, Warnke R, Staudt L M: Distinct types of diffuse large B-cell lymphoma identified by gene expression profiling. Nature 403:503-11, 2000

131. Diehn M, Eisen M B, Botstein D, Brown P O: Large-scale identification of secreted and membrane-associated gene products using DNA microarrays. Nat Biotech 25:58-62, 2000

132. Wang E, Miller L D, Ohnmacht G A, Liu E T, Marincola F M: High-fidelity mRNA amplification for gene profiling. Nat Biotechnol 18:457-9, 2000

133. Somia N V, Schmitt M J, Vetter D E, Van Antwerp D, Heinemann S F, Verma I M: LFG: an anti-apoptotic gene that provides protection from Fas-mediated cell death. Proc Natl Acad Sci USA 96:12667-72, 1999

134. Elefanty A G, Begley C G, Metcalf D, Barnett L, Kontgen F, Robb L: Characterization of hematopoietic progenitor cells that express the transcription factor SCL, using a lacZ "knock-in" strategy. Proc Natl Acad Sci USA 95:11897-902, 1998

135. Asahara T, Takahashi T, Masuda H, Kalka C, Chen D, Iwaguro H, Inai Y, Silver M, Isner J: VEGF contributes to postnatal neovascularization by mobilizing bone marrow-derived endothelial progenitor cells. EMBO J 18:3964-72, 1999

136. Robbins P, Skelton D, Yu X, Halene S, Leonard E, Kohn D: Consistent, persistent expression from modified retroviral vectors in murine hematopoietic stem cells. Proc Natl Acad Sci (USA) 95:10182-87, 1998

137. Case S, Price M, Jordan C, Yu X, Wang L, Bauer G, Haas D, Xu D, Stripecke R, Naldini L, Kohn D, Crooks G: Stable transduction of quiescent CD34(+)CD38(−) human hematopoietic cells by HIV-1-based lentiviral vectors. Proc Natl Acad Sci USA 96:2988-93, 1999

138. Uchida N, Sutton R, Friera A, He D, Reitsma M, Chang W, Veres G, Scollay R, IL. W: HIV, but not murine leukemia virus, vectors mediate high efficiency gene transfer into freshly isolated G0/G1 human hematopoietic stem cells. Proc Natl Acad Sci USA 95:11939-44, 1998

139. Takahashi T, Kalka C, Masuda H, Chen D, Silver M, Kearney M, Magner M, Isner J M, Asahara T: Ischemia- and cytokine-induced mobilization of bone marrow-derived endothelial progenitor cells for neovascularization. Nat Med 5:434-8, 1999

140. Phinney D G, Kopen G, Isaacson R L, Prockop D J: Plastic adherent stromal cells from the bone marrow of commonly used strains of inbred mice: variations in yield, growth, and differentiation. J Cell Biochem 72:570-85, 1999

141. Svendsen C N, Skepper J, Rosser A E, ter Borg M G, Tyres P, Ryken T: Restricted growth potential of rat neural precursors as compared to mouse. Brain Res Dev Brain Res 99:253-8, 1997

142. Cheshier S H, Morrison S J, Liao X, Weissman I L: In vivo proliferation and cell cycle kinetics of long-term self-renewing hematopoietic stem. Proc Natl Acad Sci USA 96:3120-5, 1999

143. Horner P J, Power A E, Kempermann G, Kuhn H G, Palmer T D, Winkler J, Thal L J, Gage F H: Proliferation and differentiation of progenitor cells throughout the intact adult rat spinal cord. J Neurosci 20:2218-28, 2000

144. Randall T D, Weissman I L: Phenotypic and functional changes induced at the clonal level in hematopoietic stem cells after 5-fluorouracil treatment. Blood 89:3596-606, 1997

What is claimed is:

1. A cell culture comprising isolated expanded human multipotent non-embryonic, non-germ cells that can differentiate into at least one cell type of at least two of the endodermal, ectodermal, and mesodermal embryonic lineages, said cells having undergone at least 10-40 cell doublings in culture.

2. The cell culture of claim 1 wherein the non-embryonic, non-germ cells express one or more of oct4, telomerase, rex-1, rox-1, or sox-2.

3. The cell culture of claim 1 wherein the non-embryonic, non-germ cells can differentiate into at least one cell type of each of the endodermal, ectodermal, and mesodermal embryonic lineages.

4. The cell culture of claim 3 wherein the non-embryonic, non-germ cells express one or more of oct4, telomerase, rex-1, rox-1, or sox-2.

5. A method for making a cell culture composition, said method comprising introducing the isolated expanded human non-embryonic, non-germ cells of claim 1 into cell culture medium.

6. A method for making the cell culture of claim 1, the method comprising:

a. obtaining the non-embryonic, non-germ cells from non-embryonic, non-germ tissue containing the cells, and b. culturing the non-embryonic, non-germ cells to produce a cell culture in which the non-embryonic, non-germ cells have undergone 10-40 cell doublings.

7. A method for producing a differentiated progeny cell, said method comprising culturing the cells from the cell culture of claim 1 under conditions that are suitable to induce differentiation, thereby producing a differentiated progeny cell.

8. The cell culture as in any of claims 1-4, in which the isolated expanded human multipotent non-embryonic, non-germ cells are derived from bone marrow.

9. The method of claim 5 wherein the isolated expanded human multipotent non-embryonic, non-germ cells are derived from bone marrow.

10. The method of claim 6 wherein the isolated expanded human multipotent non-embryonic, non-germ cells are derived from bone marrow.

* * * * *

UNITED STATES PATENT AND TRADEMARK OFFICE
CERTIFICATE OF CORRECTION

PATENT NO. : 10,006,004 B2  
APPLICATION NO. : 12/416715  
DATED : June 26, 2018  
INVENTOR(S) : Leo T. Furcht et al.

Page 1 of 1

It is certified that error appears in the above-identified patent and that said Letters Patent is hereby corrected as shown below:

In the Specification

Column 1, Lines 4-9:
Please DELETE the entire first paragraph, beginning with "Portions of the" to and ending "in the invention."

Signed and Sealed this
Third Day of March, 2020

Andrei Iancu
*Director of the United States Patent and Trademark Office*